United States Patent
Evarts et al.

(10) Patent No.: US 9,018,221 B2
(45) Date of Patent: Apr. 28, 2015

(54) PHOSPHATIDYLINOSITOL 3-KINASE INHIBITORS

(71) Applicant: Gilead Calistoga LLC, Foster City, CA (US)

(72) Inventors: Jerry Evarts, Redmond, WA (US); Leena Patel, Mercer Island, WA (US); Jennifer A. Treiberg, Redmond, WA (US); Stephane Perreault, Brier, WA (US); Arthur Yeung, Redmond, WA (US); Lafe J. Purvis, II, Seattle, WA (US); Musong Kim, Bothell, WA (US)

(73) Assignee: Gilead Calistoga, LLC, Foster City, CA (US)

( * ) Notice: Subject to any disclaimer, the term of this patent is extended or adjusted under 35 U.S.C. 154(b) by 0 days.

(21) Appl. No.: 14/137,978

(22) Filed: Dec. 20, 2013

(65) Prior Publication Data

US 2014/0179673 A1    Jun. 26, 2014

Related U.S. Application Data

(60) Provisional application No. 61/745,429, filed on Dec. 21, 2012.

(51) Int. Cl.
| | | |
|---|---|---|
| C07D 403/12 | (2006.01) | |
| C07D 401/14 | (2006.01) | |
| A01N 43/54 | (2006.01) | |
| A61K 31/517 | (2006.01) | |
| C07D 403/14 | (2006.01) | |
| C07D 417/14 | (2006.01) | |
| C07D 471/08 | (2006.01) | |

(52) U.S. Cl.
CPC ............ *C07D 403/12* (2013.01); *C07D 401/14* (2013.01); *C07D 403/14* (2013.01); *C07D 417/14* (2013.01); *C07D 471/08* (2013.01)

(58) Field of Classification Search
USPC ...................................... 514/266.21; 544/284
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,902,514 A | 2/1990 | Barclay et al. |
| 4,943,593 A | 7/1990 | Palfreyman et al. |
| 4,965,288 A | 10/1990 | Palfreyman et al. |
| 4,992,445 A | 2/1991 | Lawter et al. |
| 4,997,854 A | 3/1991 | Kagan et al. |
| 5,001,139 A | 3/1991 | Lawter et al. |
| 5,021,456 A | 6/1991 | Palfreyman et al. |
| 5,023,252 A | 6/1991 | Hseih |
| 5,059,714 A | 10/1991 | Palfreyman et al. |
| 5,120,764 A | 6/1992 | McCarthy et al. |
| 5,182,297 A | 1/1993 | Palfreyman et al. |
| 5,252,608 A | 10/1993 | Palfreyman et al. |
| 5,616,345 A | 4/1997 | Geoghegan et al. |
| 5,858,753 A | 1/1999 | Chantry et al. |
| 5,882,910 A | 3/1999 | Chantry et al. |
| 5,985,589 A | 11/1999 | Chantry et al. |
| 6,518,277 B1 | 2/2003 | Sadhu et al. |
| 6,667,300 B2 | 12/2003 | Sadhu et al. |
| 6,800,620 B2 | 10/2004 | Sadhu et al. |
| 6,949,535 B2 | 9/2005 | Sadhu et al. |

(Continued)

FOREIGN PATENT DOCUMENTS

| | | |
|---|---|---|
| EP | 0 884 310 B1 | 9/2005 |
| WO | WO-97/46688 A1 | 12/1997 |
| WO | WO-01/19800 A2 | 3/2001 |
| WO | WO 01/30768 A1 | 5/2001 |
| WO | WO-01/81346 A2 | 11/2001 |
| WO | WO-01/98278 A1 | 12/2001 |
| WO | WO-2012/097000 A1 | 7/2002 |
| WO | WO-03/076418 A1 | 9/2003 |
| WO | WO-2004/037176 A2 | 5/2004 |
| WO | WO-2004/037176 A3 | 5/2004 |

(Continued)

OTHER PUBLICATIONS

Pinedo et al (2000).*
McMahon et al (2000).*
Ameriks, M.K. et al. (May 1, 2009). "Small Molecule Inhibitors of Phosphoinositide 3-Kinase (PI3K) σ and γ," *Current Topics in Medicinal Chemistry* 9(8):738-753.

(Continued)

*Primary Examiner* — Paul V. Ward
(74) *Attorney, Agent, or Firm* — YuMing Dammann

(57) ABSTRACT

The present disclosure provides phosphatidylinositol 3-kinase (PI3K) inhibitors of formula (I),

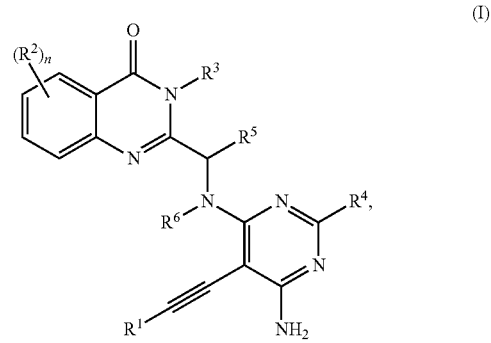

or pharmaceutically acceptable salts thereof, in which $R^1$, $R^2$, n, $R^3$, $R^4$, $R^5$ and $R^6$ are as defined herein. These compounds are useful for treatment of conditions mediated by one or more PI3K isoforms, such as PI3Kδ. The present disclosure further provides pharmaceutical compositions that include a compound of formula (I), or pharmaceutically acceptable salts thereof, and methods of using these compounds and compositions to treat conditions mediated by one or more PI3K isoforms, such as PI3Kδ.

13 Claims, No Drawings

(56) References Cited

U.S. PATENT DOCUMENTS

| | | |
|---|---|---|
| 7,932,260 B2 | 4/2011 | Fowler et al. |
| 8,138,195 B2 | 3/2012 | Sadhu et al. |
| 8,193,182 B2 | 6/2012 | Ren et al. |
| 8,207,153 B2 | 6/2012 | Fowler et al. |
| 8,492,389 B2 | 7/2013 | Sadhu et al. |
| 8,569,323 B2 | 10/2013 | Ren et al. |
| RE44,599 E | 11/2013 | Fowler et al. |
| 8,586,597 B2 | 11/2013 | Fowler et al. |
| RE44,638 E | 12/2013 | Fowler et al. |
| 8,623,881 B2 | 1/2014 | Sadhu et al. |
| 8,637,533 B2 | 1/2014 | Sadhu et al. |
| 8,653,077 B2 | 2/2014 | Sadhu et al. |
| 8,779,131 B2 | 7/2014 | Kesicki et al. |
| 2002/0161014 A1 | 10/2002 | Sadhu et al. |
| 2004/0248871 A1 | 12/2004 | Farjanel et al. |
| 2008/0234299 A1 | 9/2008 | Buchstaller et al. |
| 2010/0256167 A1 | 10/2010 | Fowler et al. |
| 2011/0046165 A1 | 2/2011 | Ren et al. |
| 2011/0152296 A1 | 6/2011 | Cushing et al. |
| 2011/0217300 A1 | 9/2011 | Liu et al. |
| 2011/0245257 A1 | 10/2011 | Cushing et al. |
| 2011/0269779 A1 | 11/2011 | Wilson et al. |
| 2011/0275653 A1 | 11/2011 | Chen et al. |
| 2011/0281866 A1 | 11/2011 | Ren et al. |
| 2011/0281897 A1 | 11/2011 | Chen et al. |
| 2012/0015964 A1 | 1/2012 | Fowler et al. |
| 2012/0059000 A1 | 3/2012 | Ren et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0202785 A1 | 8/2012 | Heald et al. |
| 2012/0245169 A1 | 9/2012 | Ren et al. |
| 2014/0121223 A1 | 5/2014 | Fowler et al. |
| 2014/0121224 A1 | 5/2014 | Fowler et al. |
| 2014/0154772 A1 | 6/2014 | Sadhu et al. |
| 2014/0179718 A1 | 6/2014 | Evarts et al. |

FOREIGN PATENT DOCUMENTS

| | | |
|---|---|---|
| WO | WO-2005/051922 A1 | 6/2005 |
| WO | WO-2005/113556 A1 | 12/2005 |
| WO | WO-2005/123696 A1 | 12/2005 |
| WO | WO-2006/004915 A1 | 1/2006 |
| WO | WO-2008/118455 A1 | 10/2008 |
| WO | WO-2009/088986 A1 | 7/2009 |
| WO | WO-2009/088990 A1 | 7/2009 |
| WO | WO-2010/059593 A1 | 5/2010 |
| WO | WO-2010/092340 A1 | 8/2010 |
| WO | WO-2010/151735 A3 | 11/2010 |
| WO | WO-2010/151735 A2 | 12/2010 |
| WO | WO-2010/151740 A2 | 12/2010 |
| WO | WO-2010/151740 A3 | 12/2010 |
| WO | WO-2011/008302 A1 | 1/2011 |
| WO | WO-01/19800 A3 | 3/2011 |
| WO | WO-01/19800 A9 | 3/2011 |
| WO | WO-2011/031896 A2 | 3/2011 |
| WO | WO-2011/031896 A3 | 3/2011 |
| WO | WO-2011/058113 A1 | 5/2011 |
| WO | WO-2011/075628 A1 | 6/2011 |
| WO | WO-2011/075699 A2 | 6/2011 |
| WO | WO-2011/075699 A3 | 6/2011 |
| WO | WO 2011/123751 A2 | 10/2011 |
| WO | WO 2011/123751 A3 | 10/2011 |
| WO | WO-01/81346 A3 | 11/2011 |
| WO | WO-2011/146882 A1 | 11/2011 |
| WO | WO-2011/150156 A2 | 12/2011 |
| WO | WO-2011/150156 A3 | 12/2011 |
| WO | WO-2012/003271 A1 | 1/2012 |
| WO | WO-2012/003274 A1 | 1/2012 |
| WO | WO-2012/037204 A1 | 3/2012 |
| WO | WO-2012/061696 A1 | 5/2012 |
| WO | WO-2012/068343 A1 | 5/2012 |
| WO | WO-2012/087784 A1 | 6/2012 |
| WO | WO-2012/125629 A1 | 9/2012 |
| WO | WO-2012/135009 A1 | 10/2012 |
| WO | WO-2012/146666 A1 | 11/2012 |
| WO | WO-2012/146667 A1 | 11/2012 |
| WO | WO-2013/032591 A1 | 3/2013 |
| WO | WO-2014/100765 A1 | 6/2014 |
| WO | WO-2014/100767 A1 | 6/2014 |

OTHER PUBLICATIONS

Chantry, D. et al. (1997). "p110δ, a Novel Phosphatidylinositol 3-Kinase Catalytic Subunit That Associates with p85 and Is Expressed Predominantly in Leukocytes," *J. Biol. Chem.* 272(31):19236-19241.

Cheson, B.D. et al. (Aug. 7, 2008). "Monoclonal Antibody Therapy for B-Cell Non-Hodgkin's Lymphoma," *The New England Journal of Medicine* 359(6):613-626.

Ferrara N. et al. (Dec. 1999). "Clinical Application of Angiogenic Growth Factors and Their Inhibitors," *Nature Medicine* 5(12):1359-1364.

Foster, A.B. (Dec. 1984). "Deuterium Isotope Effects in Studies of Drug Metabolism," *Trends Pharmacol. Sci.* 5(12):524-527.

Hiles, I.D. et al. (Aug. 7, 1992). "Phosphatidylinositol 3-Kinase: Structure and Expression of the 110 kd Catalytic Subunit," *Cell* 70(3):419-429.

International Search Report mailed on Feb. 19, 2014, for PCT Application No. PCT/US2013/077311, filed on Dec. 20, 2013, 3 pages.

International Search Report mailed on Feb. 19, 2014, for PCT Application No. PCT/US2013/077315, filed on Dec. 20, 2013, 5 pages.

Morton, L.M., et al. (Jan. 1, 2006, e-published Sep. 8, 2005). "Lymphoma Incidence Patterns by WHO Subtype in the United States, 1992-2001," *Blood* 107(1):265-276.

Nicolaou, K.C. et al. (Feb. 1, 1994). "Calicheamicin θ: A Rationally Designed Molecule with Extremely Potent and Selective DNA Cleaving Properties and Apoptosis Inducing Activity," *Angewandte Chemie International Edition in English* 33(2):1983-186.

Norman, P. (Nov. 2011, e-published Sep. 23, 2011). "Novel 1, 5-Naphthyridine PI3Kδ Inhibitors, an Evaluation of WO2011075628," *Expert Opinion on Therapeutic Patents* 21(11):1805-1810.

Otsu, M. et al. (Apr. 5, 1991). "Characterization of Two 85 kd Proteins That Associate with Receptor Tyrosine Kinases, Middle-T/pp60$^{c-src}$ Complexes, and PI3-Kinase Cell," 65(1):91-104.

Panayotou, G. et al. (Dec. 1992). "Phosphatidyl-Inositol 3-Kinase: a Key Enzyme in Diverse Signalling Processes," *Trends in Cell Biol.* 2(12):358-360.

Rameh, L.E. et al. (Mar. 26, 1999). "The Role of Phosphoinositide 3-Kinase Lipid Products in Cell Function," *J. Biol. Chem.* 274(13):8347-8350.

Vanhaesebroeck, B. et al. (Apr. 29, 1997). "P110δ, a Novel Phosphoinositide 3-Kinase in Leukocytes," *Proc. Natl. Acad. Sci. USA*, 94(9):4330-4335.

Verheijen, J.C. et al. (Jun. 1, 2007). "Phosphatidylinositol 3-Kinase (PI3K) Inhibitors as Anticancer Drugs," *Drugs of the Future* 32(6):537-547.

Wierda, W.G. (2006). "Current and Investigational Therapies for Patients with CLL," *Hematology Am. Soc. Hematol. Educ. Program* pp. 285-294.

Written Opinion mailed on Feb. 19, 2014, for PCT Application No. PCT/US2013/077311, filed on Dec. 20, 2013, 5 pages.

Written Opinion mailed on Feb. 19, 2014, for PCT Application No. PCT/US2013/077315, filed on Dec. 20, 2013, 9 pages.

U.S. Appl. No. 14/284,331, filed May 21, 2014, by Kesicki et al.

* cited by examiner

PHOSPHATIDYLINOSITOL 3-KINASE INHIBITORS

CROSS-REFERENCE TO RELATED APPLICATIONS

This application claims the benefit of U.S. Provisional Patent Application Ser. No. 61/745,429, filed Dec. 21, 2012, the disclosure of which is hereby incorporated by reference in its entirety.

FIELD

The present disclosure relates generally to inhibitors of phosphatidylinositol 3-kinase (PI3K) activity and, more specifically, to novel compounds that are selective inhibitors of PI3K delta activity.

BACKGROUND

Cell signaling via 3'-phosphorylated phosphoinositides has been implicated in a variety of cellular processes, e.g., malignant transformation, growth factor signaling, inflammation, and immunity. See generally Rameh et al., *J. Biol. Chem.*, 274:8347-8350 (1999). The enzyme responsible for generating these phosphorylated signaling products is phosphatidylinositol 3-kinase (PI 3-kinase; PI3K). PI3K originally was identified as an activity associated with viral onco-proteins and growth factor receptor tyrosine kinases that phosphorylate phosphatidylinositol (PI) and its phosphorylated derivatives at the 3'-hydroxyl of the inositol ring. See Panayotou et al., *Trends Cell Biol* 2:358-60 (1992).

Presently, three classes of the PI 3-kinase (PI3K) enzymes are distinguished, based on their substrate specificities. Class I PI3Ks can phosphorylate phosphatidylinositol (PI), phosphatidylinositol-4-phosphate, and phosphatidylinositol-4,5-biphosphate ($PIP_2$) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits. See Otsu et al., *Cell*, 65:91-104 (1991); Hiles et al., *Cell*, 70:419-29 (1992). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β, and p110δ, each interact with the same regulatory subunit, i.e., p85, whereas p110γ interacts with a distinct p101 regulatory subunit. As described below, the patterns of expression of each of these PI3Ks in human cells and tissues also are distinct.

Identification of the p110δ isoform of PI 3-kinase is described in Chantry et al., *J. Biol. Chem.*, 272:19236-41 (1997). It was observed that the human p110δ isoform is expressed in a tissue-restricted fashion. It is expressed at high levels in lymphocytes and lymphoid tissues, suggesting that the protein might play a role in PI 3-kinase-mediated signaling in the immune system. Details concerning the p110δ isoform also can be found in U.S. Pat. Nos. 5,858,753; 5,822,910; and 5,985,589, each of which is incorporated herein by reference. See also Vanhaesebroeck et al., *Proc. Natl. Acad. Sci. USA*, 94:4330-5 (1997); and WO 97/46688.

A need remains, however, for additional therapeutic agents useful to treat proliferative disorders or diseases that are mediated by PI3K. The present invention provides novel compounds that are inhibitors of PI3K isoforms.

SUMMARY

Compounds and pharmaceutically acceptable salts thereof useful for inhibiting PI3K isoforms, such as PI3Kδ, are described herein. Compositions, including pharmaceutical compositions, and kits that include the compounds are also provided, as are methods of using and making the compounds. The compounds provided herein may find use in treating diseases, disorders, or conditions that are mediated by PI3K isoforms, such as PI3Kδ.

In one aspect, provided is a compound of Formula (I):

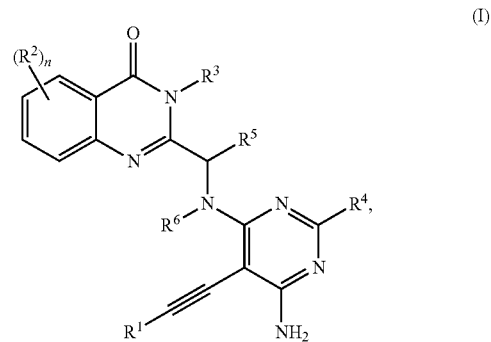

(I)

or a pharmaceutically acceptable salt, prodrug, or solvate thereof, wherein:

$R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;

n is 0, 1, 2, or 3;

each $R^2$ is independently halo or unsubstituted or substituted alkyl;

$R^3$ is unsubstituted or substituted aryl, unsubstituted or substituted heteroaryl, unsubstituted or substituted cycloalkyl, or unsubstituted or substituted heterocycloalkyl;

$R^4$ is hydrogen, alkyl, or $NH_2$;

$R^5$ is alkyl; and $R^6$ is hydrogen, or $R^5$ together with the carbon to which it is attached and $R^6$ together with the nitrogen to which it is attached are taken together to form a four-, five- or six-membered heterocycle.

In another aspect, provided herein is also a compound of formula (IA):

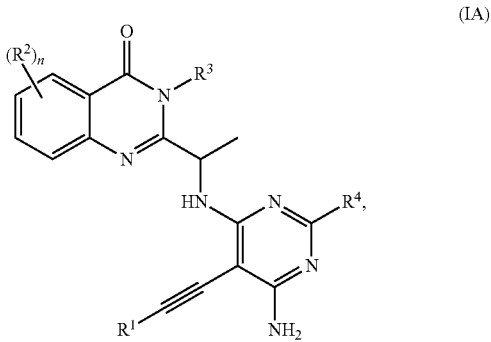

(IA)

or a pharmaceutically acceptable salt, prodrug, or solvate thereof, wherein:

$R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;

n is 0, 1, 2, or 3;
each $R^2$ is independently halo or unsubstituted or substituted alkyl;
$R^3$ is unsubstituted or substituted aryl; and
$R^4$ is hydrogen or $NH_2$.

In yet another aspect, provided herein is also a compound of formula (IB):

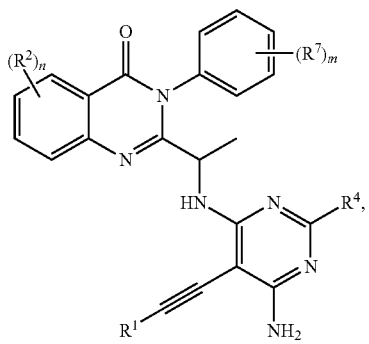

or a pharmaceutically acceptable salt, prodrug, or solvate thereof, wherein:
$R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;
n is 0, 1, 2, or 3;
each $R^2$ is independently halo or unsubstituted or substituted alkyl;
$R^4$ is hydrogen or $NH_2$;
m is 0, 1 or 2; and
each $R^7$ is independently halo, —C(O)$NR^{3a}R^{3b}$ and —S(O)$_2NR^{3a}R^{3b}$,
wherein $R^{3a}$ and $R^{3b}$ are independently hydrogen or $C_{1-6}$ alkyl.

In yet another aspect, provided herein is also a compound of formula (IC):

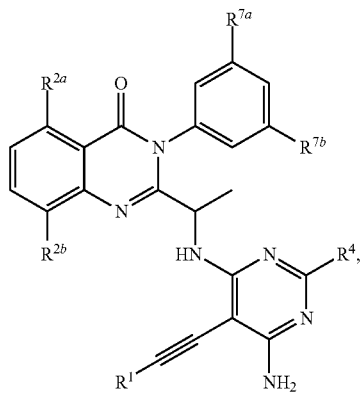

or a pharmaceutically acceptable salt, prodrug, or solvate thereof, wherein:
$R^1$ is unsubstituted or substituted aryl, unsubstituted or substituted heteroaryl, unsubstituted or substituted cycloalkyl or unsubstituted or substituted heterocycloalkyl, or unsubstituted or substituted alkyl;
$R^{2a}$ and $R^{2b}$ are independently hydrogen, halo or unsubstituted or substituted alkyl;
$R^4$ is hydrogen or $NH_2$; and
$R^{7a}$ and $R^{7b}$ are independently hydrogen, halo, —C(O)$NR^{3a}R^{3b}$ and —S(O)$_2NR^{3a}R^{3b}$,
wherein $R^{3a}$ and $R^{3b}$ are independently hydrogen or $C_{1-6}$ alkyl.

Provided is also a compound of formula (II):

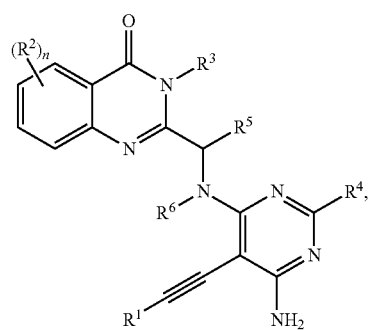

or a pharmaceutically acceptable salt, prodrug, or solvate thereof, wherein:
$R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;
n is 0, 1, 2, or 3;
each $R^2$ is independently halo, OH, CN, unsubstituted or substituted alkyl, haloalkyl, or $SO_2R^{2a}$, wherein $R^{2a}$ is alkyl;
$R^3$ is unsubstituted or substituted aryl, unsubstituted or substituted heteroaryl, unsubstituted or substituted cycloalkyl, or unsubstituted or substituted heterocycloalkyl;
$R^4$ is hydrogen, alkyl, or $NH_2$;
$R^5$ is alkyl or alkyl substituted with OH or $OR^{5a}$, wherein $R^{5a}$ is alkyl; and
$R^6$ is hydrogen, or $R^5$ together with the carbon to which it is attached and $R^6$ together with the nitrogen to which it is attached are taken together to form a four-, five- or six-membered heterocycle.

In yet another aspect, provided is a compound selected from Table 1, or a pharmaceutically acceptable salt, prodrug, or solvate thereof. In yet another aspect, provided is a compound selected from Table 1a, or a pharmaceutically acceptable salt, prodrug, or solvate thereof.

Also provided is a pharmaceutical composition that includes a compound of formula (I), (IA), (IB), (IC), or (II), or a pharmaceutically acceptable salt, prodrug, or solvate thereof, together with at least one pharmaceutically acceptable vehicle. Examples of pharmaceutically acceptable vehicle may be selected from carriers, adjuvants, and excipients.

Also provided is a method of treating a subject, who has or is suspected of having a disease or condition responsive or believed to be responsive to the inhibition of PI3Kδ activity by administering to the subject a compound of formula (I), (IA), (IB), (IC), or (II), or a pharmaceutically acceptable salt, prodrug, or solvate thereof. In some embodiments, the subject is a human.

Also provided is a kit that includes a compound of formula (I), (IA), (IB), (IC), or (II), or a pharmaceutically acceptable salt, prodrug, or solvate thereof; and a label and/or instructions for use of the compound in the treatment of a disease or condition mediated by PI3Kδ activity.

Also provided are articles of manufacture that include a compound of formula (I), (IA), (IB), (IC), or (II), or a pharmaceutically acceptable salt, prodrug, or solvate thereof; and a container. In one embodiment, the container may be a vial, jar, ampoule, preloaded syringe, or an intravenous bag.

DETAILED DESCRIPTION

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom.

Reference to "about" a value or parameter herein includes (and describes) embodiments that are directed to that value or parameter per se. For example, description referring to "about X" includes description of "X".

"Alkyl" refers to a monoradical unbranched or branched saturated hydrocarbon chain. In some embodiments, alkyl as used herein, such as in compounds of formula (I), (IA), (IB), (IC), or (II), has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl. In some embodiments, "lower alkyl" refers to alkyl groups having 1 to 6 carbons (i.e. $C_{1-6}$ alkyl).

"Cycloalkyl" refers to a cyclic alkyl group. In some embodiments, cycloalkyl as used herein, such as in compounds of formula (I), (IA), (IB), (IC), or (II), has from 3 to 20 ring carbon atoms (i.e., $C_{3-20}$ cycloalkyl), or 3 to 12 ring carbon atoms (i.e., $C_{3-12}$ cycloalkyl), or 3 to 8 ring carbon atoms (i.e., $C_{3-8}$ cycloalkyl). Examples of cycloalkyl groups include cyclopropyl, cyclobutyl, cyclopentyl, and cyclohexyl.

"Heterocycloalkyl" refers to a cyclic alkyl group, with one or more ring heteroatoms independently selected from nitrogen, oxygen and sulfur. In some embodiments, the heterocycloalkyl as used herein, such as in compounds of formula (I), (IA), (IB), (IC), or (II), has 2 to 20 ring carbon atoms (i.e., $C_{2-20}$ heterocycloalkyl), 2 to 12 ring carbon atoms (i.e., $C_{2-12}$ heterocycloalkyl), or 2 to 8 ring carbon atoms (i.e., $C_{2-8}$ heterocycloalkyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen. In one example, a heterocycloalkyl has 2 to 8 ring carbon atoms, with 1 to 3 ring heteroatoms independently selected from nitrogen, oxygen and sulfur. Examples of heterocycloalkyl groups may include pyrrolidinyl, piperidinyl, piperazinyl, oxetanyl, dioxolanyl, azetidinyl, and morpholinyl. The heterocycloalkyl may have one or more rings. For example, the heterocycloalkyl may be monocyclic or bicyclic.

"Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments, aryl as used herein, such as in compounds of formula (I), (IA), (IB), (IC), or (II), has 6 to 20 ring carbon atoms (i.e. $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein, such as in compounds of formula (I), (IA), (IB), (IC), or (II), has 3 to 20 ring carbon atoms (i.e., $C_{3-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include, but are not limited to, pyridyl, pyridazinyl, pyrimidinyl, benzothiazolyl, and pyrazolyl. In one embodiment, heteroaryl is selected from 2-pyridyl, 3-pyridyl, 3-pyridazinyl, 2-pyrazinyl, 5-pyrimidinyl, benzo[d]thiazol-6-yl, and 4-pyrazolyl. Heteroaryl does not encompass or overlap with aryl as defined above.

The term "substituted", as used herein, means that any one or more hydrogen atoms on the designated atom or group is replaced with a moiety other than hydrogen, provided that the designated atom's normal valence is not exceeded.

"Substituted alkyl" refers to an alkyl group having one or more substituents including, for example, hydroxyl, haloalkyl, alkoxy, cycloalkyl, heterocycloalkyl, aryl, heteroaryl, amino, cyano, halo, and carboxyl. In some embodiments, a substituted alkyl may have 1 to 5 substituents, 1 to 3 substituents, 1 to 2 substituents, or 1 substituent.

"Substituted cycloalkyl" refers to a cycloalkyl group having one or more substituents including, for example, alkyl, haloalkyl, heterocycloalkyl, aryl, heteroaryl, alkoxy, amino, cyano, halo, carboxyl, and hydroxyl. In some embodiments, a substituted cycloalkyl may have 1 to 5 substituents, 1 to 3 substituents, 1 to 2 substituents, or 1 substituent.

"Substituted heterocycloalkyl" refers to a heterocycloalkyl group having one or more substituents including, for example, alkyl, haloalkyl, cycloalkyl, aryl, heteroaryl, alkoxy, amino, cyano, halo, carboxyl, and hydroxyl. In some embodiments, a substituted heterocycloalkyl may have 1 to 5 substituents, 1 to 3 substituents, 1 to 2 substituents, or 1 substituent. In certain embodiments, a substituted heterocycloalkyl may contain 1, 2 or 3 heteroatoms independently selected from nitrogen, oxygen, and sulfur.

"Substituted aryl" refers to an aryl group having one or more substituents including, for example, halo, OR, —C(O)$NR_2$, —$SO_2NR_2$, alkyl, haloalkyl, heterocycloalkyl, heteroaryl, alkoxy, amino, cyano, and carboxyl, where each R is independently selected from hydrogen, alkyl, and haloalkyl. In some embodiments, a substituted aryl may have 1 to 5 substituents, 1 to 3 substituents, 1 to 2 substituents, or 1 substituent.

"Substituted heteroaryl" refers to a heteroaryl group having one or more substituents including, for example, alkyl, haloalkyl, halo, $NH_2$, OR, —C(O)OR, heterocycloalkyl, aryl, and cyano, where each R is independently selected from hydrogen, alkyl, and haloalkyl. In some embodiments, a substituted heteroaryl may have 1 to 5 substituents, 1 to 3 substituents, 1 to 2 substituents, or 1 substituent. In certain embodiments, a substituted heteroaryl may contain 1, 2 or 3 heteroatoms independently selected from nitrogen, oxygen, and sulfur.

The term "halogen" or "halo" includes fluoro, chloro, bromo, and iodo, and the term "halogen" includes fluorine, chlorine, bromine, and iodine. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. For example, dihaloaryl, dihaloalkyl, and trihaloaryl refer to aryl and alkyl substituted with two ("di") or three ("tri") halo groups, which may be, but are not necessarily, the same halogen; thus, for example, 3,5-difluorophenyl, 3-chloro-5-fluorophenyl, 4-chloro-3-fluorophenyl, and 3,5-difluoro-4-chlorophenyl is within the scope of dihaloaryl. Other examples of a haloalkyl group include difluoromethyl (—$CHF_2$) and trifluoromethyl (—$CF_3$). It should be understood that trifluoromethyl (—$CF_3$) may also be referred to as perfluoromethyl.

PI3K Inhibitor Compounds

Provided herein are compounds that function as PI3Kδ inhibitors. In one aspect, provided is a compound of formula (I):

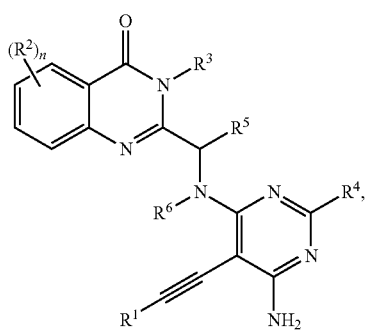

(I)

or a pharmaceutically acceptable salt, prodrug, or solvate thereof, wherein:

$R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;

n is 0, 1, 2, or 3;

each $R^2$ is independently halo or unsubstituted or substituted alkyl;

$R^3$ is unsubstituted or substituted aryl, unsubstituted or substituted heteroaryl, unsubstituted or substituted cycloalkyl, or unsubstituted or substituted heterocycloalkyl;

$R^4$ is hydrogen, alkyl, or —$NH_2$;

$R^5$ is alkyl; and $R^6$ is hydrogen, or $R^5$ together with the carbon to which it is attached and $R^6$ together with the nitrogen to which it is attached are taken together to form a four-, five- or six-membered heterocycle.

In some embodiments of formula (I), $R^1$ is:

unsubstituted aryl;

unsubstituted heteroaryl;

unsubstituted cycloalkyl;

aryl, heteroaryl, or cycloalkyl substituted with 1 or 2 substituents independently selected from the group consisting of halo, —$OR^{1a}$, —$C(O)OR^{1a}$, —$C(O)R^{1a}$, $NH_2$, alkyl, and haloalkyl, wherein $R^{1a}$ is alkyl or haloalkyl;

unsubstituted alkyl; or alkyl substituted with OH.

In certain embodiments of formula (I), $R^1$ is:

unsubstituted $C_{6-12}$ aryl;

$C_{6-12}$ aryl substituted with 1 or 2 substituents independently selected from the group consisting of halo and —$OR^{1b}$, wherein $R^{1b}$ is $C_{1-6}$ alkyl or $C_{1-6}$ haloalkyl;

unsubstituted $C_{3-12}$ heteroaryl with 1 or 2 heteroatoms independently selected from the group consisting of nitrogen and sulfur;

$C_{3-12}$ heteroaryl with 1 or 2 heteroatoms independently selected from the group consisting of nitrogen and sulfur, and substituted with 1 or 2 substituents independently selected from the group consisting of halo, —$OR^{1c}$, —$C(O)OR^{1c}$, —$C(O)R^{1c}$, $NH_2$, and $C_{1-6}$ haloalkyl, wherein $R^{1c}$ is $C_{1-6}$ alkyl or $C_{1-6}$ haloalkyl;

unsubstituted $C_{3-12}$ cycloalkyl;

unsubstituted $C_{1-6}$ alkyl; or $C_{1-6}$ alkyl substituted with OH.

In one embodiment of formula (I), $R^1$ is substituted $C_{1-6}$ alkyl. For example, the substituted $C_{1-6}$ alkyl is 1-hydroxyethyl or hydroxyisopropyl.

In certain embodiments of formula (I), $R^1$ is:

unsubstituted phenyl;

phenyl substituted with 1 or 2 substituents independently selected from the group consisting of fluoro and —$OR^{1b}$, wherein $R^{1b}$ is methyl or perfluoromethyl; unsubstituted pyridyl;

pyridyl substituted with 1 or 2 substituents independently selected from the group consisting of fluoro, —$OR^{1c}$, —$C(O)OR^{1c}$, —$C(O)R^{1c}$, $NH_2$, perfluoromethyl, wherein $R^{1c}$ is methyl or perfluoromethyl;

unsubstituted pyridazinyl;

unsubstituted pyrazinyl;

unsubstituted pyrimidinyl;

pyrimidinyl substituted with $NH_2$;

unsubstituted pyrazolyl;

unsubstituted benzothiazolyl; or benzothiazolyl substituted with $NH_2$.

In certain embodiments of formula (I), $R^1$ is:

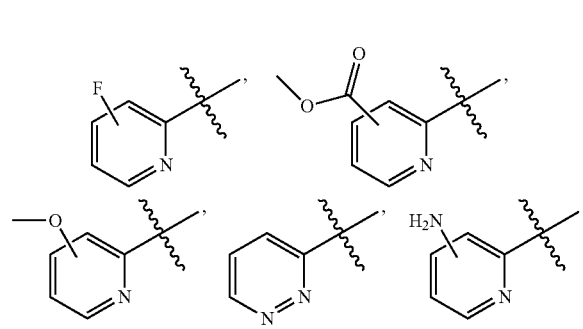

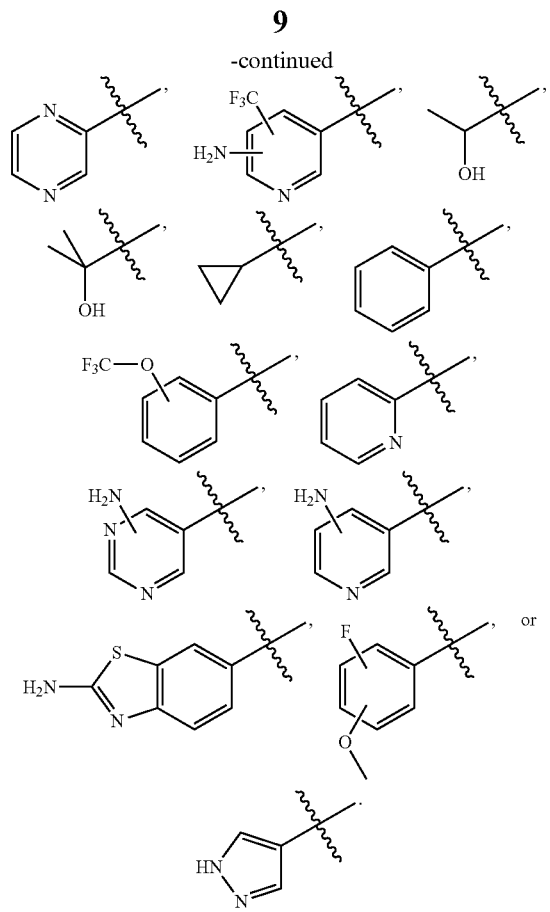

In one embodiment of formula (I), R¹ is:

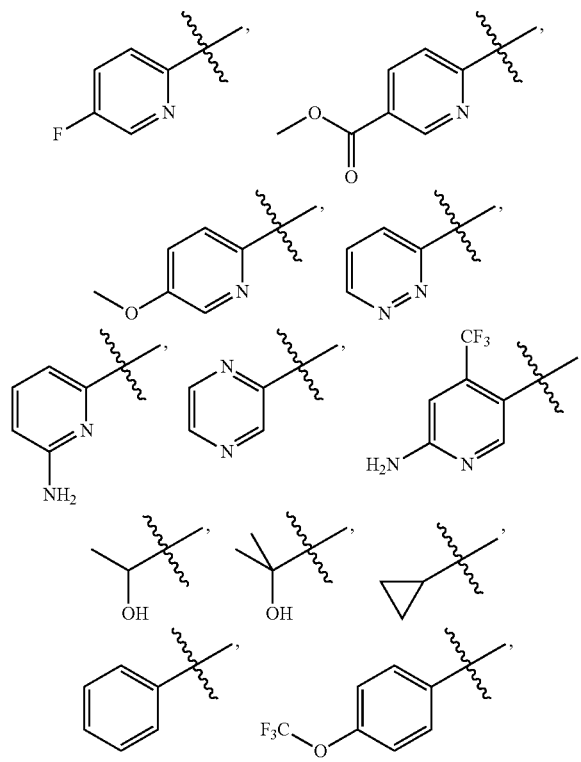

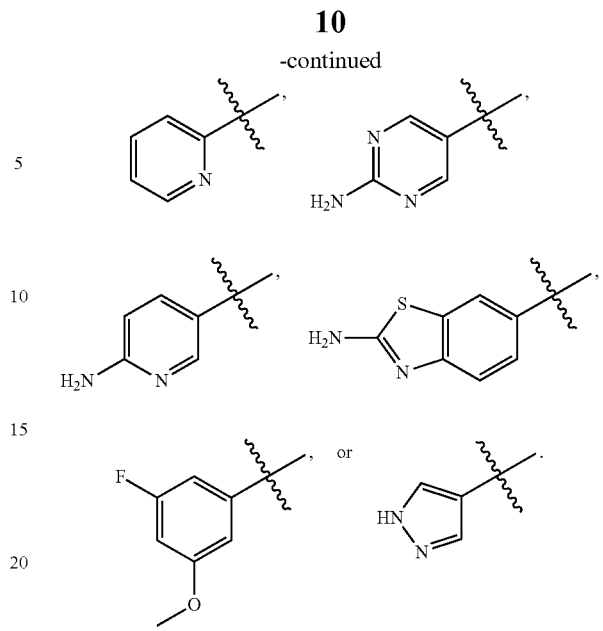

It is intended and understood that each and every variation of R¹ may be combined with each and every variation of n and R², R³, R⁴, R⁵ and R⁶ as described for formula (I), as if each and every combination is individually described.

In one embodiment of formula (I), n is 0. In other embodiments, n is 1, 2 or 3. In certain embodiments, n is 1 or 2. In one embodiment, n is 1. The R² moiety may be located on any position of the quinazolinone ring, as depicted below.

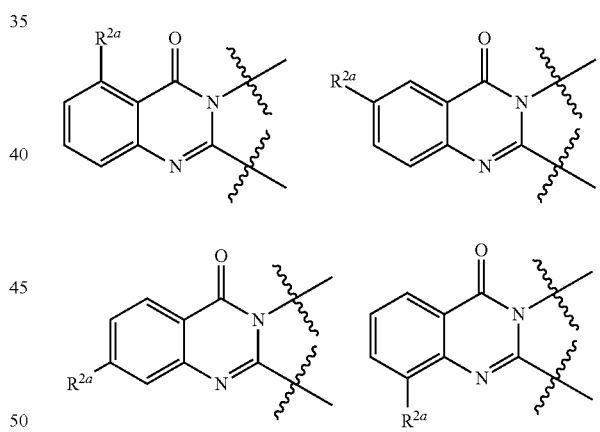

In another embodiment, n is 2. In embodiments where n is 2, both R² may be the same or different. Two R² moieties may be located of any two positions of the quinazolinone ring as depicted below. For example, two R² moieties may be in para-, meta- or ortho-positions to each other.

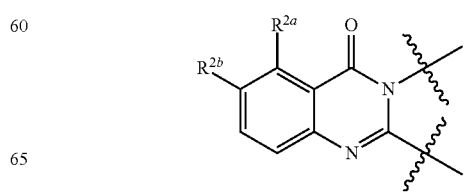

-continued

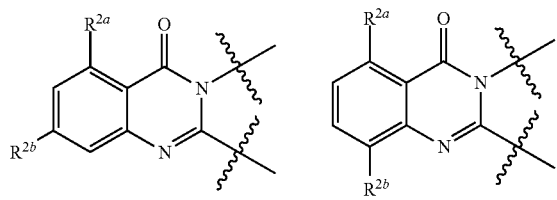

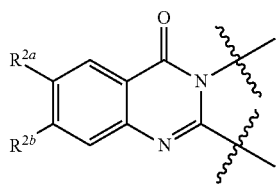

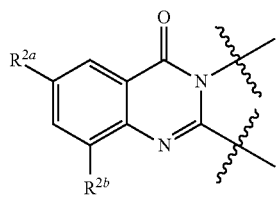

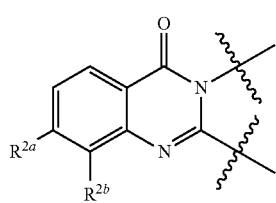

In yet another embodiment, n is 3. In embodiments where n is 3, all R² may be the same or different, or two R² may be the same and different from the third R². Three R² moieties may be located on any three positions of the quinazolinone ring as depicted below. For example, the first R² may be ortho to the second R², and the first R² may be para to the third R².

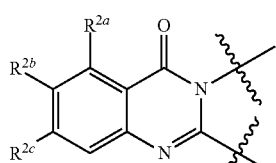

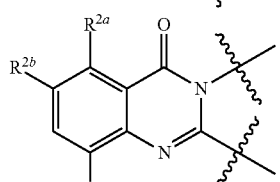

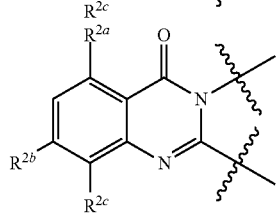

-continued

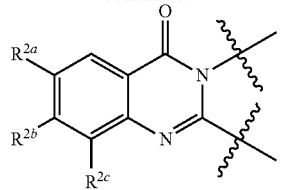

In some embodiments, each R² is independently halo or unsubstituted alkyl, alkyl substituted with cyano or haloalkyl. In certain embodiments, R² is independently fluoro, chloro, methyl, or halomethyl. In one embodiment, n is 0. In another embodiment, n is 1, wherein R² is fluoro or chloro. In yet another embodiment, n is 2, wherein each R² is independently fluoro or chloro.

It is intended and understood that each and every variation of n and R² may be combined with each and every variation of R¹, R³, R⁴, R⁵ and R⁶ as described for formula (I), as if each and every combination is individually described.

In some embodiments, R³ is:
unsubstituted $C_{6-12}$ aryl; or
$C_{6-12}$ aryl substituted with 1 or 2 substituents independently selected from the group consisting of halo, alkyl, haloalkyl, cyano, —C(O)NR$^{3a}$R$^{3b}$ and —SO$_2$NR$^{3a}$R$^3$, wherein R$^{3a}$ and R$^{3b}$ are independently hydrogen or $C_{1-6}$ alkyl.

In certain embodiments, R³ is:
unsubstituted phenyl; or
phenyl substituted with 1 or 2 substituents independently selected from the group consisting of fluoro, chloro, cyano, halomethyl, —C(O)NR$^{3a}$R$^{3b}$ and —S(O)$_2$NR$^{3a}$R$^{3b}$, wherein R$^{3a}$ and R$^{3b}$ are independently hydrogen, methyl or ethyl.

In certain embodiments, R³ is:

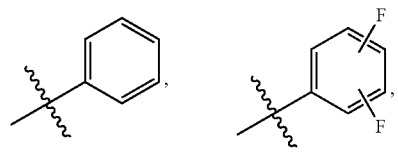

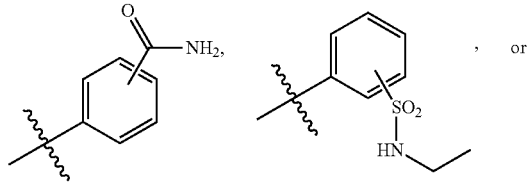

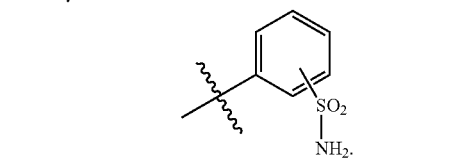

In one embodiment, R³ is:

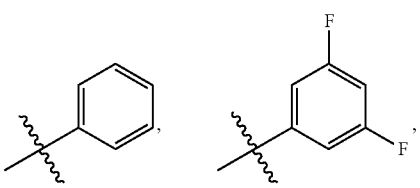

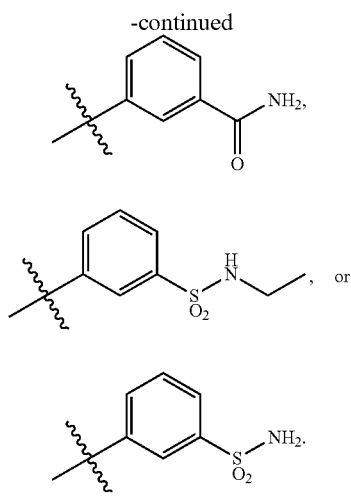

It is intended and understood that each and every variation of $R^3$ may be combined with each and every variation of $R^1$, n, $R^2$, $R^4$, $R^5$ and $R^6$ as described for formula (I), as if each and every combination is individually described.

In some embodiments, $R^4$ is hydrogen, $C_{1-6}$ alkyl, or $NH_2$. In one embodiment, $R^4$ is hydrogen. In another embodiment, $R^4$ is methyl. In yet another embodiment, $R^4$ is $NH_2$.

It is intended and understood that each and every variation of $R^4$ may be combined with each and every variation of $R^1$, n, $R^2$, $R^3$, $R^5$ and $R^6$ as described for formula (I), as if each and every combination is individually described.

In some embodiments, $R^5$ is $C_{1-6}$ alkyl. In one embodiment, $R^5$ is methyl. In one embodiment, $R^6$ is hydrogen. In other embodiments, $R^5$ together with the carbon to which it is attached and $R^6$ together with the nitrogen to which it is attached are taken together to form a five- or six-membered heterocycloalkyl.

It is intended and understood that each and every variation of $R^5$ may be combined with each and every variation of $R^1$, n, $R^2$, $R^3$, $R^4$ and $R^6$ as described for formula (I), as if each and every combination is individually described.

In some embodiments, the compound of formula (I) is the (S)-enantiomer. In other embodiments of formula (II), the compound of formula (II) is the (R)-enantiomer. In certain embodiments, the compound has the structure of formula (I'):

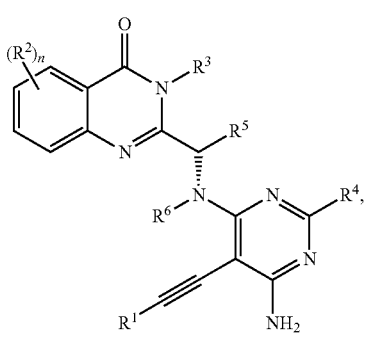

or a pharmaceutically acceptable salt, prodrug, or solvate thereof, wherein $R^1$, $R^2$, n, $R^3$, $R^4$, $R^5$ and $R^6$ are as defined above for compounds of formula (I).

In some embodiments, the compound of formula (I) is a compound of formula (IA):

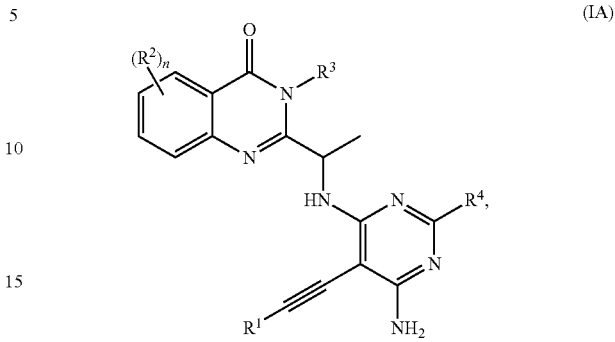

or a pharmaceutically acceptable salt, prodrug, or solvate thereof, wherein $R^1$, $R^2$, n, $R^3$, and $R^4$ are as defined above for compounds of formula (I). In some embodiments, the compound of formula (IA) is the (S)-enantiomer.

In certain embodiments of formula (IA),
$R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;
n is 0, 1, 2, or 3;
each $R^2$ is independently halo or alkyl;
$R^3$ is unsubstituted or substituted aryl; and
$R^4$ is hydrogen or $NH_2$.

In other embodiments, the compound of formula (I) is a compound of formula (IB):

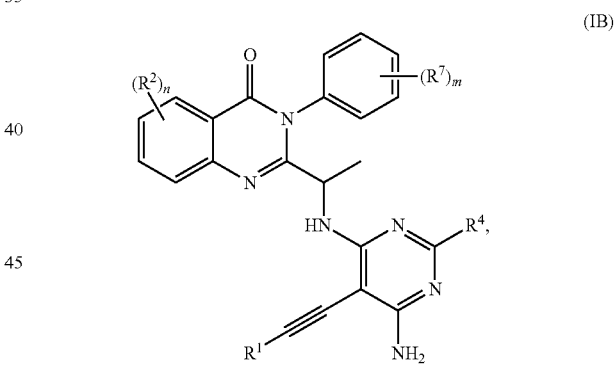

or a pharmaceutically acceptable salt, prodrug, or solvate thereof, wherein:
$R^1$, $R^2$, n, and $R^4$ are as defined above for compounds of formula (I);
m is 0, 1 or 2; and
each $R^7$ is independently halo, —C(O)$NR^{3a}R^{3b}$ and —S(O)$_2NR^{3a}R^{3b}$,
wherein $R^{3a}$ and $R^{3b}$ are independently hydrogen or $C_{1-6}$ alkyl.

In certain embodiments of formula (IB),
$R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;
n is 0, 1, 2, or 3;
each $R^2$ is independently halo or unsubstituted or substituted alkyl;

$R^4$ is hydrogen or $NH_2$;
m is 0, 1 or 2; and
each $R^7$ is independently halo, —C(O)$NR^{3a}R^{3b}$ and —S(O)$_2NR^{3a}R^{3b}$,
  wherein $R^{3a}$ and $R^{3b}$ are independently hydrogen or $C_1$—alkyl.

In some embodiments, the compound of formula (IB) is the (S)-enantiomer. In some embodiments, each $R^7$ is independently fluoro, —C(O)$NH_2$, —S(O)$_2NR^{3a}R^{3b}$, wherein $R^{3a}$ and $R^{3b}$ are independently hydrogen, methyl, or ethyl. In one embodiment, m is 0. In another embodiment, m is 1, and $R^7$ is —C(O)$NH_2$, —S(O)$_2NR^{3a}R^{3b}$, wherein $R^{3a}$ and $R^{3b}$ are independently hydrogen, methyl, or ethyl. In yet another embodiment, m is 2, and each $R^7$ is fluoro.

In yet other embodiments, the compound of formula (I) is a compound of formula (IC):

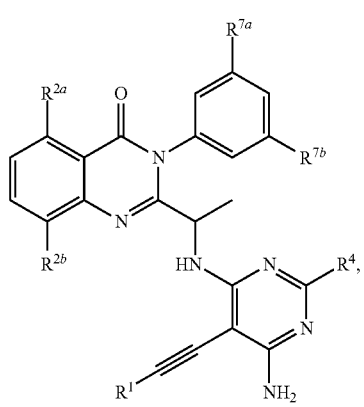

(IC)

or a pharmaceutically acceptable salt, prodrug, or solvate thereof, wherein:
  $R^1$ and $R^4$ are as defined above for compounds of formula (I);
  $R^{2a}$ and $R^{2b}$ are independently hydrogen, halo or unsubstituted or substituted alkyl; and
  $R^{7a}$ and $R^{7b}$ are independently hydrogen, halo, —C(O)$NR^{3a}R^{3b}$ and —S(O)$_2NR^{3a}R^{3b}$,
    wherein $R^{3a}$ and $R^{3b}$ are independently hydrogen or $C_{1-6}$ alkyl.

In certain embodiments of formula (IC),
  $R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;
  $R^{2a}$ and $R^{2b}$ are independently hydrogen, halo or unsubstituted or substituted alkyl;
  $R^4$ is hydrogen, alkyl, or $NH_2$; and
  $R^{7a}$ and $R^{7b}$ are independently hydrogen, halo, —C(O)$NR^{3a}R^{3b}$ and —S(O)$_2NR^{3a}R^{3b}$,
    wherein $R^{3a}$ and $R^{3b}$ are independently hydrogen or $C_{1-6}$ alkyl.

In some embodiments, the compound of formula (IC) is the (S)-enantiomer. In some embodiments, $R^{2a}$ and $R^{2b}$ are independently halo or unsubstituted alkyl, alkyl substituted with cyano or haloalkyl. In certain embodiments, $R^{2a}$ and $R^{2b}$ are independently hydrogen, fluoro, chloro, or $C_{1-6}$ alkyl. In one embodiment, $R^{2a}$ and $R^{2b}$ are both fluoro or are both chloro. In another embodiment, one of $R^{2a}$ and $R^{2b}$ is hydrogen, and the other is fluoro or chloro. In yet another embodiment, one of $R^{2a}$ and $R^{2b}$ is fluoro, and the other is chloro. In yet another embodiment, one of $R^{2a}$ and $R^{2b}$ is hydrogen, and the other is methyl.

In some embodiments, $R^{7a}$ and $R^{7b}$ are independently hydrogen, fluoro, chloro, —C(O)$NR^{3a}R^{3b}$ and —S(O)$_2NR^{3a}R^{3b}$, and $R^{3a}$ and $R^{3b}$ are independently hydrogen, methyl or ethyl. In one embodiment, $R^{7a}$ and $R^{7b}$ are both hydrogen or are both fluoro. In another embodiment, one of $R^{7a}$ and $R^{7b}$ is hydrogen, and the other is —C(O)$NH_2$, —S(O)$_2NR^{3a}R^{3b}$, wherein $R^{3a}$ and $R^{3b}$ are independently hydrogen, methyl, or ethyl.

It should be understood that the embodiments and structures as described herein with respect to formula (I) are suitable for compounds of any formulae detailed herein, including (IA), (IB), and (IC) where applicable.

In another aspect, provided is a compound having the structure of formula (II):

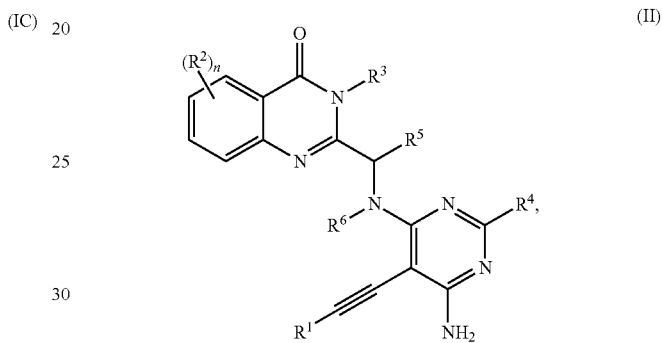

(II)

or a pharmaceutically acceptable salt, prodrug, or solvate thereof, wherein:
  $R^1$ is unsubstituted or substituted aryl, unsubstituted or substituted heteroaryl, unsubstituted or substituted cycloalkyl, unsubstituted or substituted heterocycloalkyl, or unsubstituted or substituted alkyl;
  n is 0, 1, 2, or 3;
  each $R^2$ is independently halo, OH, CN, unsubstituted or substituted alkyl, haloalkyl, or $SO_2R^{2a}$, wherein $R^{2a}$ is alkyl;
  $R^3$ is unsubstituted or substituted aryl, unsubstituted or substituted heteroaryl, unsubstituted or substituted cycloalkyl, or unsubstituted or substituted heterocycloalkyl;
  $R^4$ is hydrogen, alkyl, or $NH_2$;
  $R^5$ is alkyl or alkyl substituted with OH or $OR^{5a}$, wherein $R^{5a}$ is alkyl; and
  $R^6$ is hydrogen, or $R^5$ together with the carbon to which it is attached and $R^6$ together with the nitrogen to which it is attached are taken together to form a four-, five- or six-membered heterocycle.

In some embodiments of formula (II), $R^1$ is:
  unsubstituted aryl;
  unsubstituted heteroaryl;
  unsubstituted cycloalkyl;
  aryl, heteroaryl, or cycloalkyl substituted with 1 or 2 substituents independently selected from the group consisting of halo, —$OR^{1a}$, —C(O)$OR^{1a}$, —C(O)$R^{1a}$, $NH_2$, alkyl, haloalkyl, and $C_{1-6}$ alkyl substituted with OH or $NH_2$, wherein $R^{1a}$ is H, alkyl, haloalkyl, $NH_2$, or —O($C_{1-6}$ alkyl);
  unsubstituted alkyl; or
  alkyl substituted with OH.

In some embodiments of formula (II), $R^1$ is aryl, heteroaryl, or cycloalkyl substituted with $C_{1-6}$ alkyl substituted with OH or $NH_2$, wherein $R^{1a}$ is H, alkyl, haloalkyl, $NH_2$, or —O($C_{1-6}$ alkyl).

In other embodiments of formula (II), $R^1$ is:

unsubstituted $C_{6-12}$ aryl;

$C_{6-12}$ aryl substituted with 1 or 2 substituents independently selected from the group consisting of halo, —$OR^{1b}$, —$C(O)R^{1b}$ and $C_{1-6}$ alkyl substituted with OH, wherein $R^{1b}$ is $C_{1-6}$ alkyl or $C_{1-6}$ haloalkyl;

unsubstituted $C_{3-12}$ heteroaryl with 1 or 2 heteroatoms independently selected from the group consisting of nitrogen, oxygen and sulfur;

$C_{3-12}$ heteroaryl with 1 or 2 heteroatoms independently selected from the group consisting of nitrogen, oxygen and sulfur, and substituted with 1 or 2 substituents independently selected from the group consisting of halo, —$OR^{1c}$, —$C(O)OR^{1c}$, —$C(O)R^{1c}$, $NH_2$, $C_{1-6}$ haloalkyl, $C_{1-6}$ alkyl, and $C_{1-6}$ alkyl substituted with OH or $NH_2$, wherein $R^{1C}$ is H, $C_{1-6}$ alkyl, $C_{1-6}$ haloalkyl, $NH_2$, or —$O(C_{1-6}$ alkyl);

unsubstituted $C_{3-12}$ cycloalkyl;

unsubstituted $C_{1-6}$ alkyl; or $C_{1-6}$ alkyl substituted with OH.

In certain embodiments of formula (II), $R^1$ is:

unsubstituted cyclopentyl;

unsubstituted cyclohexyl;

unsubstituted phenyl;

phenyl substituted with 1 or 2 substituents independently selected from the group consisting of fluoro, —$OR^{1b}$, —$C(O)R^{1b}$, and $CH_2OH$, wherein $R^{1b}$ is methyl or perfluoromethyl;

unsubstituted pyridyl;

pyridyl substituted with 1 or 2 substituents independently selected from the group consisting of fluoro, —$OR^{1c}$, —$C(O)OR^{1c}$, —$C(O)R^{1c}$, $NH_2$, methyl, ethyl, perfluoromethyl, $CHF_2$, $CH_2OH$, $CH(CH_3)OH$, and $CH_2NH_2$, wherein $R^{1c}$ is H, methyl, perfluoromethyl, $NH_2$, or —$OCH(CH_3)_2$;

unsubstituted pyridazinyl;

unsubstituted pyrazinyl;

unsubstituted pyrimidinyl;

pyrimidinyl substituted with $NH_2$;

unsubstituted pyrazolyl;

unsubstituted benzothiazolyl; or benzothiazolyl substituted with $NH_2$.

In one embodiment of formula (II), $R^1$ is:

-continued

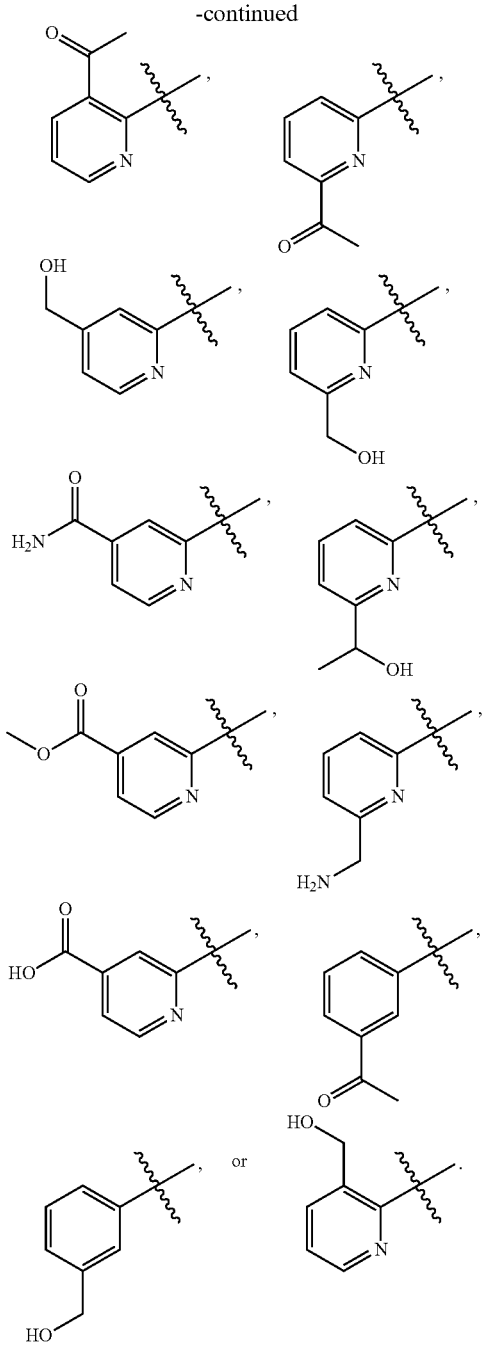

It is intended and understood that each and every variation of $R^1$ may be combined with each and every variation of n, $R^2$, $R^3$, $R^4$, $R^5$ and $R^6$ as described for formula (II), as if each and every combination is individually described.

In one embodiment of formula (II), n is 0. In other embodiments, n is 1, 2 or 3. In certain embodiments, n is 1 or 2. In one embodiment, n is 1. The $R^2$ moiety in formula (II) may be located on any position of the quinazolinone ring, as depicted above for formula (I).

In some embodiments of formula (II), each $R^2$ is independently selected from the group consisting of halo, OH, CN, unsubstituted alkyl, alkyl substituted with cyano or haloalkyl, haloalkyl, and $SO_2R^{2a}$, wherein $R^{2a}$ is alkyl. In certain embodiments, each $R^2$ is independently fluoro, chloro, OH, CN, methyl, $CF_3$, $CHF_2$, or $SO_2CH_3$. In one embodiment, each $R^2$ is independently OH, CN, haloalkyl, or $SO_2R^{2a}$, wherein $R^{2a}$ is alkyl.

It is intended and understood that each and every variation of $R^2$ may be combined with each and every variation of n, $R^1$, $R^3$, $R^4$, $R^5$ and $R^6$ as described for formula (II), as if each and every combination is individually described.

In some embodiments of formula (II), $R^3$ is:

unsubstituted $C_{6-12}$ aryl;

$C_{6-12}$ aryl substituted with 1 or 2 substituents independently selected from the group consisting of halo, alkyl, haloalkyl, aryl, cyano, —$OR^{3a}$, —$C(O)NR^{3a}R^{3b}$, —$SO_2R^{3a}$, —$SO_2NR^{3a}R^{3b}$, alkyl substituted with $NR^{3a}R^{3b}$, wherein $R^{3a}$ and $R^{3b}$ are independently hydrogen, $C_{1-6}$ alkyl, or —$SO_2R^{3c}$, wherein $R^{3c}$ is alkyl;

unsubstituted $C_{3-12}$ heteroaryl with 1 or 2 heteroatoms independently selected from the group consisting of nitrogen, oxygen and sulfur;

unsubstituted $C_{3-12}$ heterocycloalkyl with 1 or 2 heteroatoms independently selected from the group consisting of nitrogen, oxygen and sulfur; or $C_{3-12}$ heterocycloalkyl with 1 or 2 heteroatoms independently selected from the group consisting of nitrogen, oxygen and sulfur, and substituted with 1 or 2 alkyl substituents.

In certain embodiments of formula (II), $R^3$ is:

unsubstituted phenyl; or phenyl substituted with 1 or 2 substituents independently selected from the group consisting of fluoro, chloro, methyl, ethyl, propyl, butyl, phenyl, cyano, halomethyl, —$OR^{3a}$, —$C(O)NR^{3a}R^{3b}$, —$SO_2R^{3a}$, —$S(O)_2NR^{3a}R^{3b}$, methyl substituted with $NR^{3a}R^{3b}$, wherein $R^{3a}$ and $R^{3b}$ are independently hydrogen, methyl, ethyl, propyl, butyl, or —$SO_2R^{3c}$, wherein $R^{3c}$ is methyl, ethyl, propyl, butyl.

In one embodiment of formula (II), $R^3$ is:

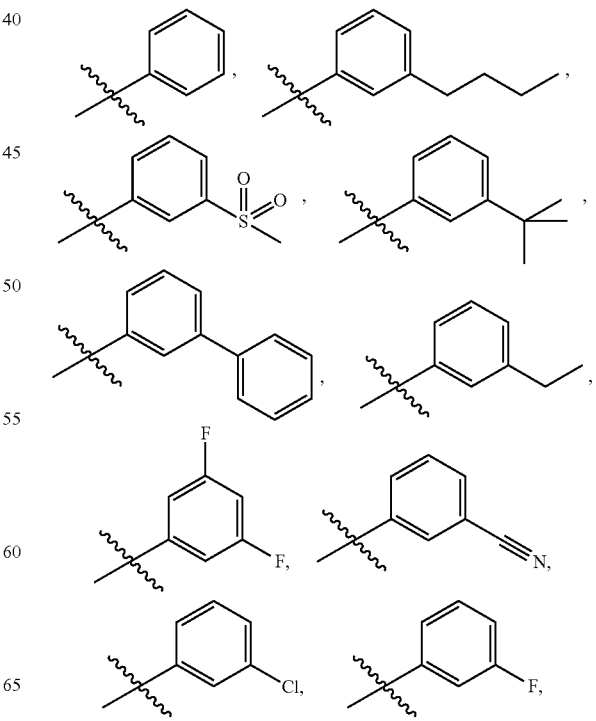

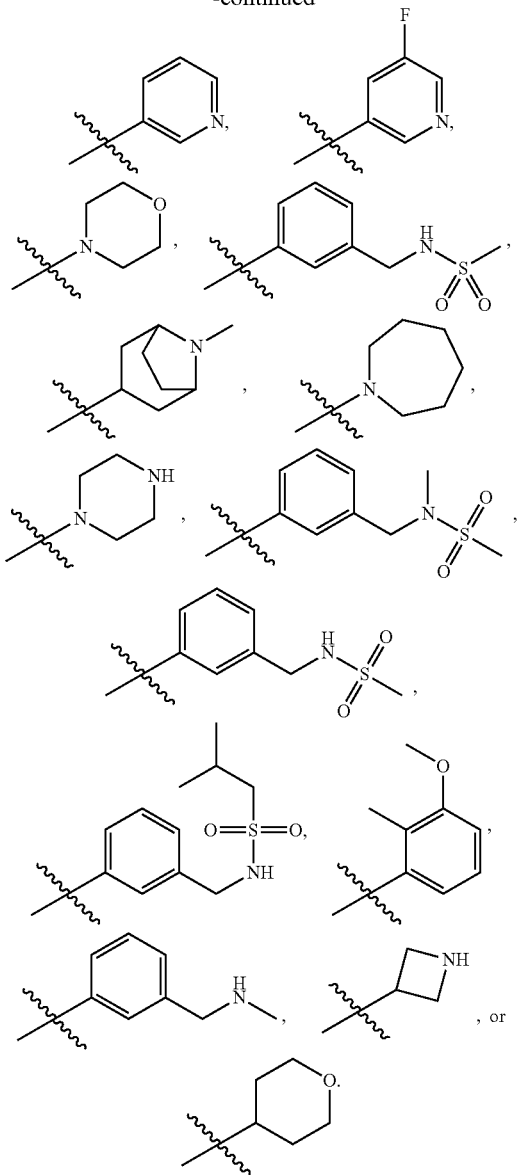

It is intended and understood that each and every variation of $R^3$ may be combined with each and every variation of $R^1$, n, $R^2$, $R^4$, $R^5$ and $R^6$ as described for formula (II), as if each and every combination is individually described.

In some embodiments of formula (II), $R^4$ is hydrogen, $C_{1-6}$ alkyl, or $NH_2$. In one embodiment, $R^4$ is hydrogen. In another embodiment, $R^4$ is methyl. In yet another embodiment, $R^4$ is $NH_2$.

It is intended and understood that each and every variation of $R^4$ may be combined with each and every variation of $R^1$, n, $R^2$, $R^3$, $R^5$ and $R^6$ as described for formula (II), as if each and every combination is individually described.

In some embodiments of formula (II), $R^5$ is $C_{1-6}$ alkyl. In one embodiment, $R^5$ is methyl. In one embodiment, $R^6$ is hydrogen. In other embodiments, $R^5$ together with the carbon to which it is attached and $R^6$ together with the nitrogen to which it is attached are taken together to form a five- or six-membered heterocycloalkyl. In some embodiments of formula (II), $R^5$ is alkyl substituted with OH or $OR^{5a}$, wherein $R^{5a}$ is alkyl.

It is intended and understood that each and every variation of $R^5$ may be combined with each and every variation of $R^1$, n, $R^2$, $R^3$, $R^4$ and $R^6$ as described for formula (II), as if each and every combination is individually described.

In some embodiments of formula (II), the compound of formula (II) is the (S)-enantiomer. In other embodiments of formula (II), the compound of formula (II) is the (R)-enantiomer.

For compounds of the invention, including the compounds of formula (I), (IA), (IB), (IC), or (II), or a pharmaceutically acceptable salt thereof, bearing one or more chiral centers, each unique stereoisomer has a compound number bearing a suffix "a", "b", etc. As an example, Compound 1 bearing one chiral center can be resolved into its individual enantiomers 1a and 1b.

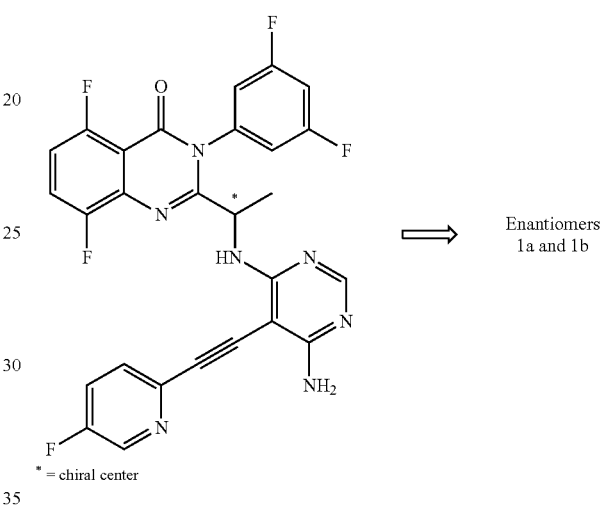

Enantiomers 1a and 1b

* = chiral center

In any one of the foregoing embodiments, the compound of formula (I), (IA), (IB), (IC), or (II), or a pharmaceutically acceptable salt thereof, is the (S)-enantiomer. In other embodiments, In some embodiments of formula (II), the compound of formula (II) is the (R)-enantiomer.

A composition containing a mixture of enantiomers of the compound of formula (I), (IA), (IB), (IC), or (II), or a pharmaceutically acceptable salt thereof, is also provided herein. In some embodiments, the composition contains the (S)-enantiomer of the compound and is substantially free of its corresponding (R)-enantiomer. In certain embodiments, a composition substantially free of the (R)-enantiomer has less than or about 40%, 35%, 30%, 25%, 20%, 15%, 10%, 5%, 1%, 0.05%, or 0.01% of the (R)-enantiomer. In other embodiments, the composition containing the (S)-enantiomer of a compound of formula (I), (IA), (IB), (IC), or (II), or a pharmaceutically acceptable salt thereof, predominates over its corresponding (R)-enantiomer by a molar ratio of at least or about 9:1, at least or about 19:1, at least or about 40:1, at least or about 80:1, at least or about 160:1, or at least or about 320:1.

The composition containing a compound of formula (I), (IA), (IB), (IC), or (II), or a pharmaceutically acceptable salt thereof, may also contain the compound in enantiomeric excess (e.e.). For instance, a compound with 95% (S)-isomer and 5% (R)-isomer will have an e.e. of 90%. In some embodiments, the compound has an e.e. of at least or about 60%, 75%, 80%, 85%, 90%, 95%, 98% or 99%. In some of the foregoing embodiments, the compound is enantiomerically-enriched in the (S)-isomer of compound of formula (I), (IA), (IB), (IC), or (II).

Provided is also a composition comprising a mixture of the (S)-enantiomer and the (R)-enantiomer of a compound of formula (I), (IA), (IB), (IC), or (II), or a pharmaceutically acceptable salt thereof. In one embodiment, the mixture is a racemic mixture. In other embodiments, the composition comprises the (S)-enantiomer of a compound of formula (I), (IA), (IB), (IC), or (II), or a pharmaceutically acceptable salt thereof, wherein the (S)-enantiomer of the compound is present in excess of over the corresponding the (R)-enantiomer of the compound, or a pharmaceutically acceptable salt thereof.

In any one of the foregoing embodiments, the compound of formula (I), (IA), (IB), (IC), or (II), or a pharmaceutically acceptable salt thereof, is an atropisomer. A composition containing a mixture of atropisomers of the compound of formula (I), (IA), (IB), (IC), or (II), or a pharmaceutically acceptable salt thereof, is also provided herein. "Atropisomers" refers to conformational stereoisomers which occur when rotation about a single bond in the molecule is prevented, or greatly slowed, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers are enantiomers without a single asymmetric atom. As an example, Compound 81 can be resolved into its individual atropisomers as depicted below.

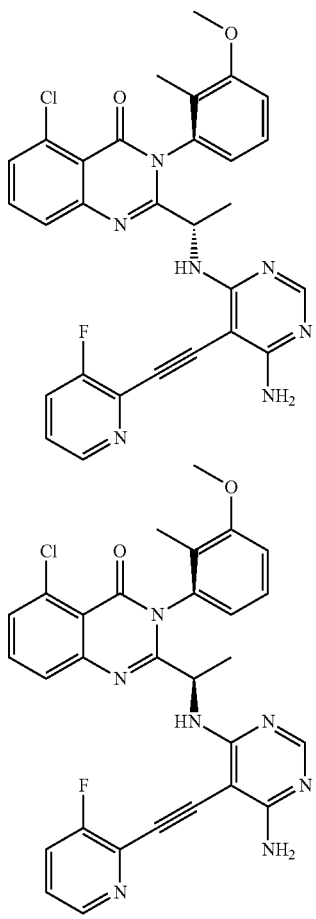

-continued

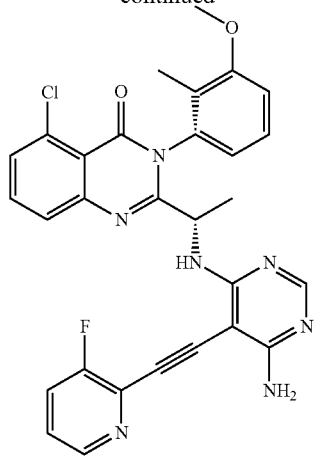

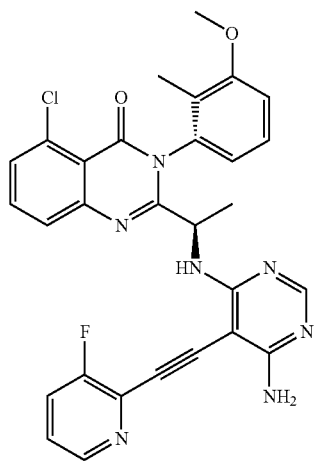

Representative compounds of the invention are listed in Table 1 and Table 1a below in its non-isomeric form. The compounds in Table 1 and Table 1a are named using ChemBioDraw Ultra 12.0 and it should be understood that other names may be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). The naming and numbering of the compounds of the present disclosure is illustrated with representative compounds of formula (I), (IA), (IB), (IC), or (II) shown in Table 1 and Table 1a below. The compounds provided in Table 1 and Table 1a may be a single enantiomer (e.g., (S)-enantiomer, (R)-enantiomer), or the compounds may be present in a composition having an enantiomeric mixture.

TABLE 1

| # | Structure | Name |
|---|-----------|------|
| 1 | 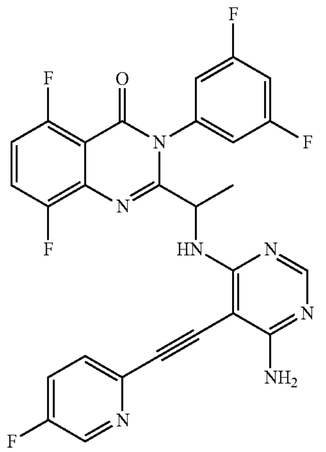 [SMILES: CC(Nc1ncnc(N)c1C#Cc1ccc(F)cn1)c1nc2c(F)ccc(F)c2c(=O)n1-c1cc(F)cc(F)c1] | 2-(1-((6-amino-5-((5-fluoro-pyridin-2-yl)ethynyl)pyrimidin-4-yl)amino)ethyl)-3-(3,5-difluorophenyl)-5,8-difluoro-quinazolin-4(3H)-one<br>1a: (S)-enantiomer<br>1b: (R)-enantiomer |
| 2 | 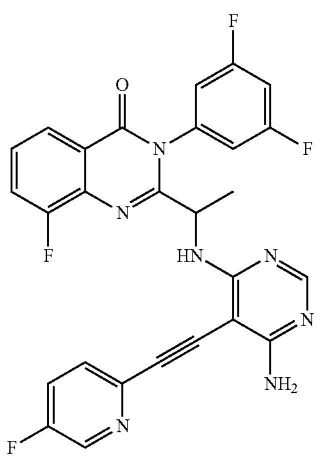 [SMILES: CC(Nc1ncnc(N)c1C#Cc1ccc(F)cn1)c1nc2c(F)cccc2c(=O)n1-c1cc(F)cc(F)c1] | 2-(1-((6-amino-5-((5-fluoro-pyridin-2-yl)ethynyl)pyrimidin-4-yl)amino)ethyl)-3-(3,5-difluorophenyl)-8-fluoroquinazolin-4(3H)-one<br>2a: (S)-enantiomer<br>2b: (R)-enantiomer |
| 3 | 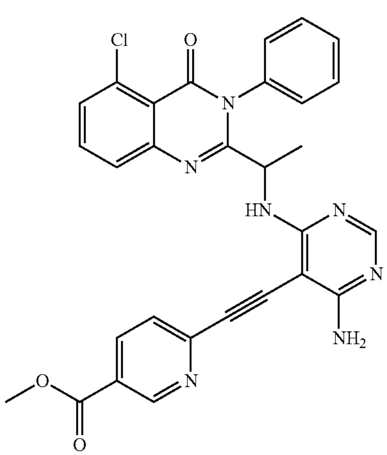 [SMILES: COC(=O)c1ccc(C#Cc2c(N)ncnc2NC(C)c2nc3cccc(Cl)c3c(=O)n2-c2ccccc2)nc1] | methyl 6-((4-amino-6-((1-(5-chloro-4-oxo-3-phenyl-3,4-dihydro-quinazolin-2-yl)ethyl)amino)pyrimidin-5-yl)ethynyl)nicotinate<br>3a: (S)-enantiomer<br>3b: (R)-enantiomer |
| 4 | | 2-(1-((6-amino-5-((5-fluoro-pyridin-2-yl)ethynyl)pyrimidin-4-yl)amino)ethyl)-5,8-difluoro-3-phenyl-quinazolin-4(3H)-one<br>4a: (S)-enantiomer<br>4b: (R)-enantiomer |
| 5 | | 2-(1-((6-amino-5-((5-fluoro-pyridin-2-yl)ethynyl)pyrimidin-4-yl)amino)ethyl)-8-chloro-3-phenyl-quinazolin-4(3H)-one<br>5a: (S)-enantiomer<br>5b: (R)-enantiomer |
| 6 | | 2-(1-((6-amino-5-((5-fluoro-pyridin-2-yl)ethynyl)pyrimidin-4-yl)amino)ethyl)-5-chloro-8-fluoro-3-phenyl-quinazolin-4(3H)-one<br>6a: (S)-enantiomer<br>6b: (R)-enantiomer |

TABLE 1-continued

Representative Compounds

| # | Structure | Name |
|---|---|---|
| 7 | 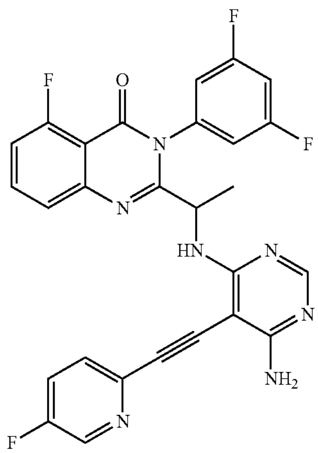 [SMILES: CC(Nc1ncnc(N)c1C#Cc1ccc(F)cn1)c1nc2cccc(F)c2c(=O)n1-c1cc(F)cc(F)c1] | 2-(1-((6-amino-5-((5-fluoro-pyridin-2-yl)ethynyl)pyrimidin-4-yl)amino)ethyl)-3-(3,5-difluoro-phenyl)-5-fluoro-quinazolin-4(3H)-one<br>7a: (S)-enantiomer<br>7b: (R)-enantiomer |
| 8 | 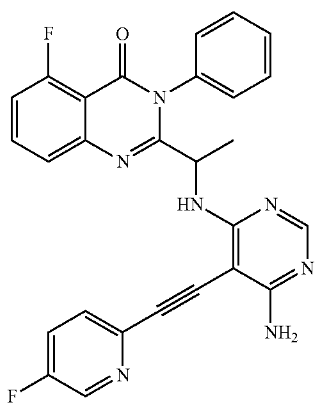 [SMILES: CC(Nc1ncnc(N)c1C#Cc1ccc(F)cn1)c1nc2cccc(F)c2c(=O)n1-c1ccccc1] | 2-(1-((6-amino-5-((5-fluoro-pyridin-2-yl)ethynyl)pyrimidin-4-yl)amino)ethyl)-5-fluoro-3-phenyl-quinazolin-4(3H)-one<br>8a: (S)-enantiomer<br>8b: (R)-enantiomer |
| 9 | 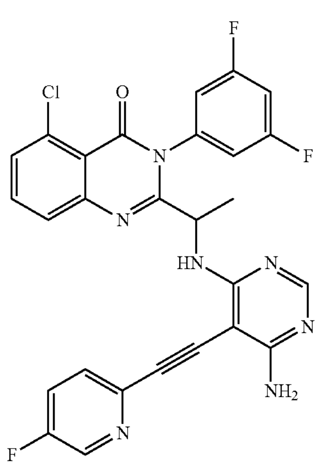 [SMILES: CC(Nc1ncnc(N)c1C#Cc1ccc(F)cn1)c1nc2cccc(Cl)c2c(=O)n1-c1cc(F)cc(F)c1] | 2-(1-((6-amino-5-((5-fluoro-pyridin-2-yl)ethynyl)pyrimidin-4-yl)amino)ethyl)-5-chloro-3-(3,5-difluorophenyl)quinazolin-4(3H)-one<br>9a: (S)-enantiomer<br>9b: (R)-enantiomer |
| 10 | | 2-(1-((6-amino-5-((5-methoxy-pyridin-2-yl)ethynyl)pyrimidin-4-yl)amino)ethyl)-5,8-dichloro-3-phenyl-quinazolin-4(3H)-one<br>10a: (S)-enantiomer<br>10b: (R)-enantiomer |
| 11 | | 2-(1-((6-amino-5-((5-fluoro-pyridin-2-yl)ethynyl)pyrimidin-4-yl)amino)ethyl)-5,8-dichloro-3-phenyl-quinazolin-4(3H)-one<br>11a: (S)-enantiomer<br>11b: (R)-enantiomer |
| 12 | | 2-(1-((6-amino-5-((5-methoxy-pyridin-2-yl)ethynyl)pyrimidin-4-yl)amino)ethyl)-8-fluoro-3-phenyl-quinazolin-4(3H)-one<br>12a: (S)-enantiomer<br>12b: (R)-enantiomer |

TABLE 1-continued

Representative Compounds

| # | Structure | Name |
|---|-----------|------|
| 13 | 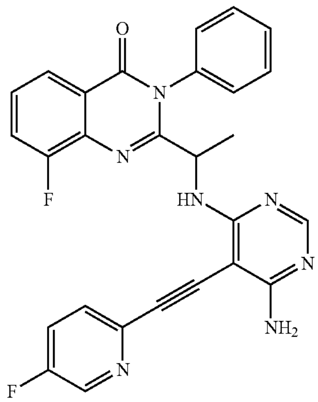 [SMILES: CC(Nc1ncnc(N)c1C#Cc1ccc(F)cn1)c1nc2c(F)cccc2c(=O)n1-c1ccccc1] | 2-(1-((6-amino-5-((5-fluoro-pyridin-2-yl)ethynyl)pyrimidin-4-yl)amino)ethyl)-8-fluoro-3-phenyl-quinazolin-4(3H)-one<br>13a: (S)-enantiomer<br>13b: (R)-enantiomer |
| 14 | 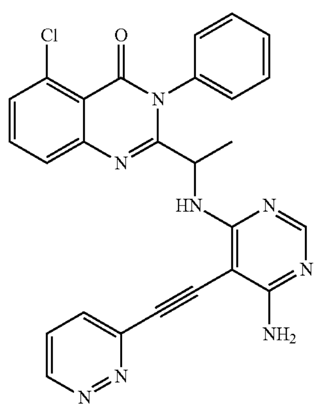 [SMILES: CC(Nc1ncnc(N)c1C#Cc1cccnn1)c1nc2cccc(Cl)c2c(=O)n1-c1ccccc1] | 2-(1-((6-amino-5-(pyridazin-3-ylethynyl)pyrimidin-4-yl)amino)ethyl)-5-chloro-3-phenyl-quinazolin-4(3H)-one<br>14a: (S)-enantiomer<br>14b: (R)-enantiomer |
| 15 | 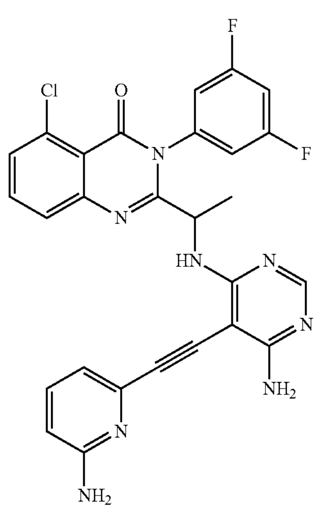 [SMILES: CC(Nc1ncnc(N)c1C#Cc1cccc(N)n1)c1nc2cccc(Cl)c2c(=O)n1-c1cc(F)cc(F)c1] | 2-(1-((6-amino-5-((6-amino-pyridin-2-yl)ethynyl)pyrimidin-4-yl)amino)ethyl)-5-difluorophenyl)quinazolin-4(3H)-one<br>15a: (S)-enantiomer<br>15b: (R)-enantiomer |
| 16 | | 2-(1-((6-amino-5-(pyrazin-2-ylethynyl)pyrimidin-4-yl)amino)ethyl)-5-chloro-3-phenyl-quinazolin-4(3H)-one<br>16a: (S)-enantiomer<br>16b: (R)-enantiomer |
| 17 | | 2-(1-((6-amino-5-((6-amino-4-(trifluoromethyl)pyridin-3-yl)ethynyl)pyrimidin-4-yl)amino)ethyl)-5-chloro-3-(3,5-difluorophenyl)quinazolin-4(3H)-one<br>17a: (S)-enantiomer<br>17b: (R)-enantiomer |
| 18 | | 2-(1-((6-amino-5-((6-amino-4-(trifluoromethyl)pyridin-3-yl)ethynyl)pyrimidin-4-yl)amino)ethyl)-5-chloro-3-phenyl-quinazolin-4(3H)-one<br>18a: (S)-enantiomer<br>18b: (R)-enantiomer |

TABLE 1-continued

Representative Compounds

| # | Structure | Name |
|---|---|---|
| 19 | 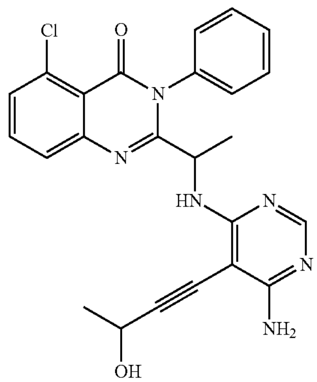 [SMILES: CC(O)C#Cc1c(N)ncnc1NC(C)c1nc2cccc(Cl)c2c(=O)n1-c1ccccc1] | 2-1-((6-amino-5-(3-hydroxybut-1-yn-1-yl)pyrimidin-4-yl)amino)ethyl)-5-chloro-3-phenyl-quinazolin-4(3H)-one<br>19a: (S), (R)-diastereomer<br>19b: (S), (S)-diastereomer |
| 20 | 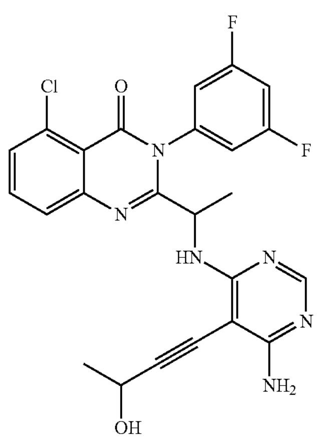 [SMILES: CC(O)C#Cc1c(N)ncnc1NC(C)c1nc2cccc(Cl)c2c(=O)n1-c1cc(F)cc(F)c1] | 2-(1-((6-amino-5-(3-hydroxybut-1-yn-1-yl)pyrimidin-4-yl)amino)ethyl)-5-chloro-3-(3,5-difluorophenyl)quinazolin-4(3H)-one<br>20a: (S), (R)-diastereomer<br>20b: (S), (S)-diastereomer |
| 23 | 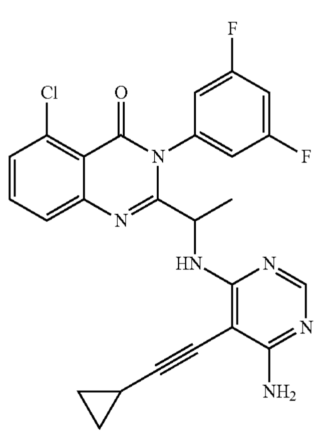 [SMILES: CC(Nc1ncnc(N)c1C#CC1CC1)c1nc2cccc(Cl)c2c(=O)n1-c1cc(F)cc(F)c1] | 2-(1-((6-amino-5-(cyclopropyl-ethynyl)pyrimidin-4-yl)amino)ethyl)-5-chloro-3-(3,5-difluorophenyl)quinazolin-4(3H)-one<br>23a: (S)-enantiomer<br>23b: (R)-enantiomer |
| 24 | | 2-(1-((6-amino-5-(cyclopropyl-ethynyl)pyrimidin-4-yl)amino)ethyl)-5-chloro-3-phenyl-quinazolin-4(3H)-one<br>24a: (S)-enantiomer<br>24b: (R)-enantiomer |
| 25 | | 5-chloro-2-(1-((2,6-diamino-5-(phenyl-ethynyl)pyrimidin-4-yl)amino)ethyl)-3-phenyl-quinazolin-4(3H)-one<br>25a: (S)-enantiomer<br>25b: (R)-enantiomer |
| 26 | | 2-(1-((6-amino-5-((4-(trifluoro-methoxy)phenyl)ethynyl)pyrimidin-4-yl)amino)ethyl)-5-chloro-3-(3,5-difluorophenyl)quinazolin-4(3H)-one<br>26a: (S)-enantiomer<br>26b: (R)-enantiomer |

TABLE 1-continued

Representative Compounds

| # | Structure | Name |
|---|-----------|------|
| 27 | 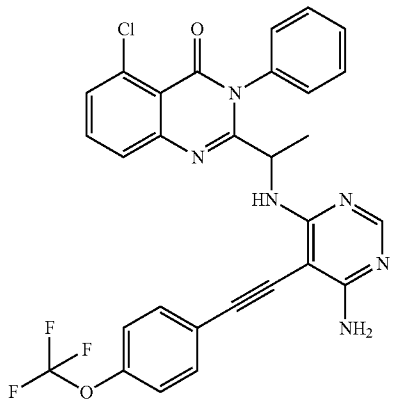 [SMILES: CC(Nc1ncnc(N)c1C#Cc1ccc(OC(F)(F)F)cc1)c1nc2cccc(Cl)c2c(=O)n1-c1ccccc1] | 2-(1-((6-amino-5-((4-(trifluoromethoxy)phenyl)ethynyl)pyrimidin-4-yl)amino)ethyl)-5-chloro-3-phenyl-quinazolin-4(3H)-one<br>27a: (S)-enantiomer<br>27b: (R)-enantiomer |
| 28 | 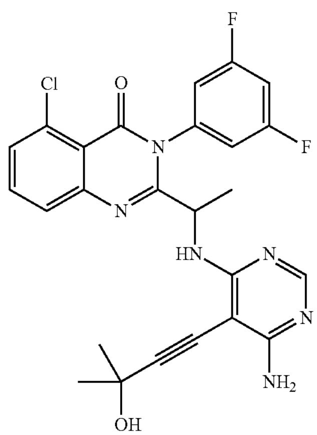 [SMILES: CC(Nc1ncnc(N)c1C#CC(C)(C)O)c1nc2cccc(Cl)c2c(=O)n1-c1cc(F)cc(F)c1] | 2-(1-((6-amino-5-(3-hydroxy-3-methylbut-1-yn-1-yl)pyrimidin-4-yl)amino)ethyl)-5-chloro-3-(3,5-difluorophenyl)quinazolin-4(3H)-one<br>28a: (S)-enantiomer<br>28b: (R)-enantiomer |
| 29 | 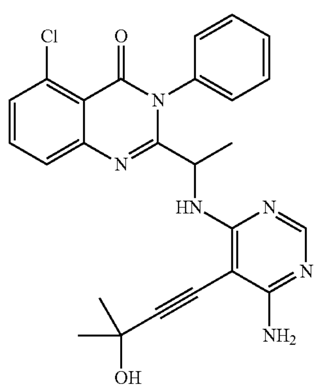 [SMILES: CC(Nc1ncnc(N)c1C#CC(C)(C)O)c1nc2cccc(Cl)c2c(=O)n1-c1ccccc1] | 2-(1-((6-amino-5-(3-hydroxy-3-methylbut-1-yn-1-yl)pyrimidin-4-yl)amino)ethyl)-5-chloro-3-phenyl-quinazolin-4(3H)-one<br>29a: (S)-enantiomer<br>29b: (R)-enantiomer |
| 30 | | 2-(1-((6-amino-5-(pyridin-2-ylethynyl)pyrimidin-4-yl)amino)ethyl)-5-methyl-3-phenyl-quinazolin-4(3H)-one<br>30a: (S)-enantiomer<br>30b: (R)-enantiomer |
| 31 | | 2-(1-((6-amino-5-((6-amino-pyridin-2-yl)ethynyl)pyrimidin-4-yl)amino)ethyl)-5-chloro-3-phenyl-quinazolin-4(3H)-one<br>31a: (S)-enantiomer<br>31b: (R)-enantiomer |
| 32 | | 2-(1-((6-amino-5-((2-amino-pyrimidin-5-yl)ethynyl)pyrimidin-4-yl)amino)ethyl)-5-chloro-3-(3,5-difluorophenyl)quinazolin-4(3H)-one<br>32a: (S)-enantiomer<br>32b: (R)-enantiomer |

TABLE 1-continued

Representative Compounds

| # | Structure | Name |
|---|---|---|
| 33 | | 2-(1-((6-amino-5-((2-amino-pyrimidin-5-yl)ethynyl)pyrimidin-4-yl)amino)ethyl)-5-chloro-3-phenyl-quinazolin-4(3H)-one<br>33a: (S)-enantiomer<br>33b: (R)-enantiomer |
| 34 | | 2-(1-((6-amino-5-((5-amino-pyrimidin-2-yl)ethynyl)pyrimidin-4-yl)amino)ethyl)-5-chloro-3-(3,5-difluorophenyl)quinazolin-4(3H)-one<br>34a: (S)-enantiomer<br>34b: (R)-enantiomer |
| 35 | | 2-(1-((6-amino-5-((5-amino-pyrimidin-2-yl)ethynyl)pyrimidin-4-yl)amino)ethyl)-5-chloro-3-phenyl-quinazolin-4(3H)-one<br>35a: (S)-enantiomer<br>35b: (R)-enantiomer |
| 36 | 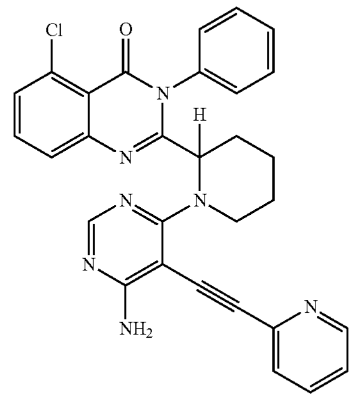 [SMILES: Nc1ncnc(N2CCCCC2c2nc3cccc(Cl)c3c(=O)n2-c2ccccc2)c1C#Cc1ccccn1] | 2-(1-(6-amino-5-(pyridin-2-ylethynyl)pyrimidin-4-yl)piperidin-2-yl)-5-chloro-3-phenyl-quinazolin-4(3H)-one<br>36a: (S)-enantiomer<br>36b: (R)-enantiomer |
| 37 | 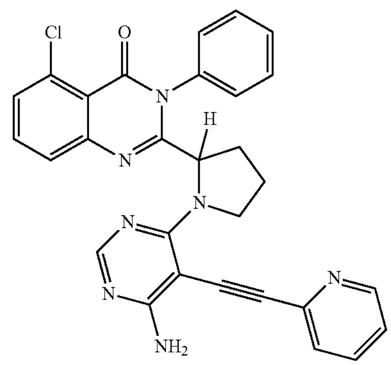 [SMILES: Nc1ncnc(N2CCCC2c2nc3cccc(Cl)c3c(=O)n2-c2ccccc2)c1C#Cc1ccccn1] | 2-(1-(6-amino-5-(pyridin-2-ylethynyl)pyrimidin-4-yl)pyrrolidin-2-yl)-5-chloro-3-phenyl-quinazolin-4(3H)-one<br>37a: (S)-enantiomer<br>37b: (R)-enantiomer |
| 38 | 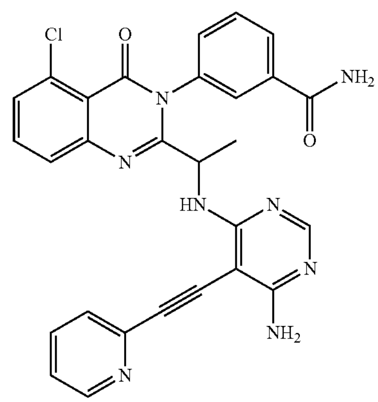 [SMILES: CC(Nc1ncnc(N)c1C#Cc1ccccn1)c1nc2cccc(Cl)c2c(=O)n1-c1cccc(C(N)=O)c1] | 3-(2-(1-((6-amino-5-(pyridin-2-ylethynyl)pyrimidin-4-yl)amino)ethyl)-5-chloro-4-oxoquinazolin-3(4H)-yl)benzamide<br>38a: (S)-enantiomer<br>38b: (R)-enantiomer |
| 39 | 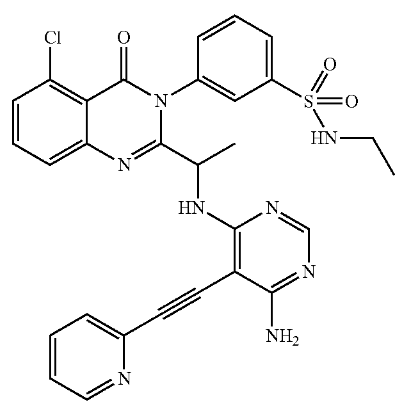 [SMILES: CCNS(=O)(=O)c1cccc(-n2c(C(C)Nc3ncnc(N)c3C#Cc3ccccn3)nc3cccc(Cl)c3c2=O)c1] | 3-(2-(1-((6-amino-5-(pyridin-2-ylethynyl)pyrimidin-4-yl)amino)ethyl)-5-chloro-4-oxoquinazolin-3(4H)-yl)-N-ethyl-benzene-sulfonamide<br>39a: (S)-enantiomer<br>39b: (R)-enantiomer |

TABLE 1-continued

Representative Compounds

| # | Structure | Name |
|---|---|---|
| 40 | 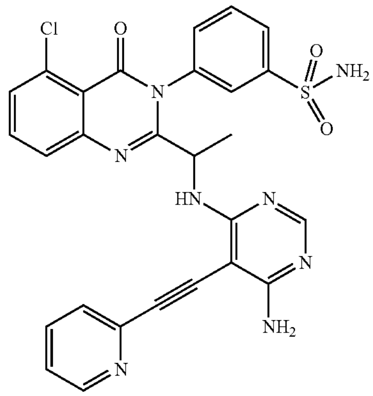 [SMILES: CC(Nc1ncnc(N)c1C#Cc1ccccn1)c1nc2cccc(Cl)c2c(=O)n1-c1cccc(S(N)(=O)=O)c1] | 3-(2-(1-((6-amino-5-(pyridin-2-ylethynyl)pyrimidin-4-yl)amino)ethyl)-5-chloro-4-oxoquinazolin-3(4H)-yl)benzenesulfonamide<br>40a: (S)-enantiomer<br>40b: (R)-enantiomer |
| 41 | 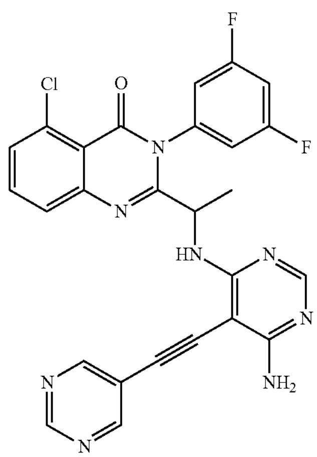 [SMILES: CC(Nc1ncnc(N)c1C#Cc1cncnc1)c1nc2cccc(Cl)c2c(=O)n1-c1cc(F)cc(F)c1] | 2-(1-((6-amino-5-(pyrimidin-5-ylethynyl)pyrimidin-4-yl)amino)ethyl)-5-chloro-3-(3,5-difluorophenyl)quinazolin-4(3H)-one<br>41a: (S)-enantiomer<br>41b: (R)-enantiomer |
| 42 | 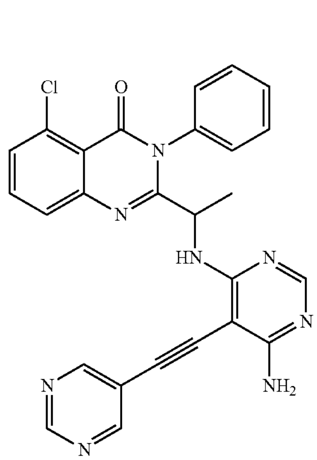 [SMILES: CC(Nc1ncnc(N)c1C#Cc1cncnc1)c1nc2cccc(Cl)c2c(=O)n1-c1ccccc1] | 2-(1-((6-amino-5-(pyrimidin-5-ylethynyl)pyrimidin-4-yl)amino)ethyl)-5-chloro-3-phenyl-quinazolin-4(3H)-one<br>42a: (S)-enantiomer<br>42b: (R)-enantiomer |
| 43 | | 2-(1-((6-amino-5-(pyridin-3-ylethynyl)pyrimidin-4-yl)amino)ethyl)-5-chloro-3-(3,5-difluorophenyl)quinazolin-4(3H)-one<br>43a: (S)-enantiomer<br>43b: (R)-enantiomer |
| 44 | | 2-(1-((6-amino-5-(pyridin-3-ylethynyl)pyrimidin-4-yl)amino)ethyl)-5-chloro-3-phenyl-quinazolin-4(3H)-one<br>44a: (S)-enantiomer<br>44b: (R)-enantiomer |
| 45 | | 2-(1-((6-amino-5-(pyridin-2-ylethynyl)pyrimidin-4-yl)amino)ethyl)-5-chloro-3-(3,5-difluorophenyl)quinazolin-4(3H)-one<br>45a: (S)-enantiomer<br>45b: (R)-enantiomer |

TABLE 1-continued

Representative Compounds

| # | Structure | Name |
|---|-----------|------|
| 46 | 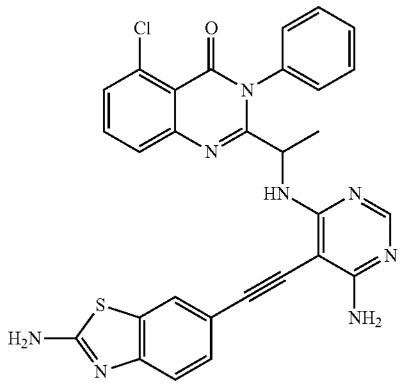 [SMILES: CC(Nc1ncnc(N)c1C#Cc1ccc2nc(N)sc2c1)c1nc2cccc(Cl)c2c(=O)n1-c1ccccc1] | 2-(1-((6-amino-5-((2-amino-benzo[d]thiazol-6-yl)ethynyl)pyrimidin-4-yl)amino)ethyl)-5-chloro-3-phenyl-quinazolin-4(3H)-one<br>46a: (S)-enantiomer<br>46b: (R)-enantiomer |
| 47 | 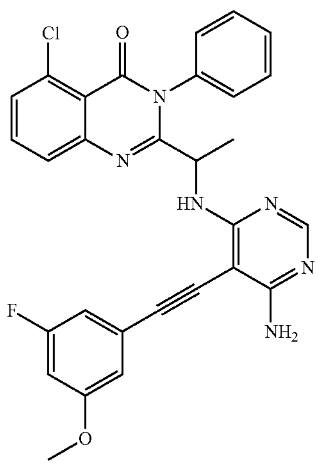 [SMILES: COc1cc(F)cc(C#Cc2c(N)ncnc2NC(C)c2nc3cccc(Cl)c3c(=O)n2-c2ccccc2)c1] | 2-(1-((6-amino-5-((3-fluoro-5-methoxyphenyl)ethynyl)pyrimidin-4-yl)amino)ethyl)-5-chloro-3-phenyl-quinazolin-4(3H)-one<br>47a: (S)-enantiomer<br>47b: (R)-enantiomer |
| 48 | 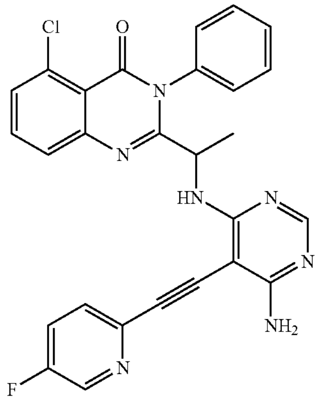 [SMILES: CC(Nc1ncnc(N)c1C#Cc1ccc(F)cn1)c1nc2cccc(Cl)c2c(=O)n1-c1ccccc1] | 2-(1-((6-amino-5-((5-fluoropyridin-2-yl)ethynyl)pyrimidin-4-yl)amino)ethyl)-5-chloro-3-phenyl-quinazolin-4(3H)-one<br>48a: (S)-enantiomer<br>48b: (R)-enantiomer |
| 49 | | 2-(1-((5-((1H-pyrazol-4-yl)ethynyl)-6-aminopyrimidin-4-yl)amino)ethyl)-5-chloro-3-phenyl-quinazolin-4(3H)-one<br>49a: (S)-enantiomer<br>49b: (R)-enantiomer |
| 50 | | 2-(1-((6-amino-5-(pyridin-2-ylethynyl)pyrimidin-4-yl)amino)ethyl)-5-chloro-3-phenyl-quinazolin-4(3H)-one<br>50a: (S)-enantiomer<br>50b: (R)-enantiomer |
| 51 | | 2-(1-((6-amino-5-(phenyl-ethynyl)pyrimidin-4-yl)amino)ethyl)-5-chloro-3-phenyl-quinazolin-4(3H)-one<br>51a: (S)-enantiomer<br>51b: (R)-enantiomer |

TABLE 1a

Representative Compounds

| # | Structure | Name |
|---|---|---|
| 52 | 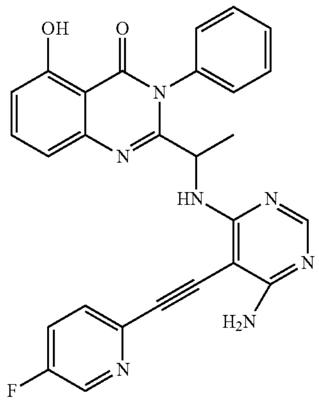 [SMILES: CC(Nc1ncnc(N)c1C#Cc1ccc(F)cn1)c1nc2cccc(O)c2c(=O)n1-c1ccccc1] | 2-(1-((6-amino-5-((5-fluoro-pyridin-2-yl)ethynyl)pyrimidin-4-yl)amino)ethyl)-5-hydroxy-3-phenyl-quinazolin-4(3H)-one<br>52a: (S)-enantiomer<br>52b: (R)-enantiomer |
| 53 | 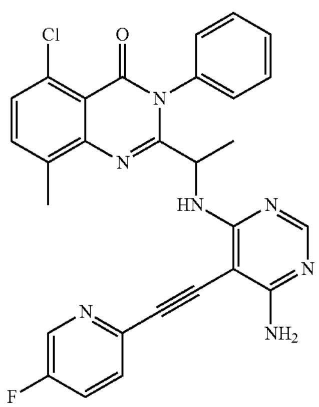 [SMILES: Cc1ccc(Cl)c2c(=O)n(-c3ccccc3)c(C(C)Nc3ncnc(N)c3C#Cc3ccc(F)cn3)nc12] | 2-(1-((6-amino-5-((5-fluoro-pyridin-2-yl)ethynyl)pyrimidin-4-yl)amino)ethyl)-5-chloro-8-methyl-3-phenyl-quinazolin-4(3H)-one<br>53a: (S)-enantiomer<br>53b: (R)-enantiomer |
| 54 | 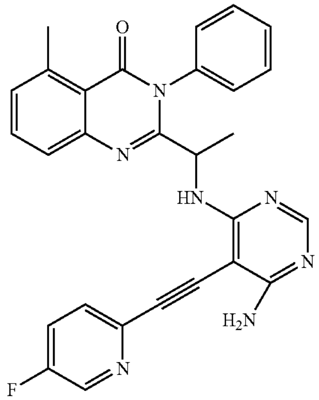 [SMILES: Cc1cccc2nc(C(C)Nc3ncnc(N)c3C#Cc3ccc(F)cn3)n(-c3ccccc3)c(=O)c12] | 2-(1-((6-amino-5-((5-fluoro-pyridin-2-yl)ethynyl)pyrimidin-4-yl)amino)ethyl)-5-methyl-3-phenyl-quinazolin-4(3H)-one<br>54a: (S)-enantiomer<br>54b: (R)-enantiomer |
| 55 | | 2-(1-((6-amino-5-(pyrazin-2-ylethynyl)pyrimidin-4-yl)amino)ethyl)-4-oxo-3-phenyl-3,4-dihydro-quinazoline-5-carbonitrile<br>55a: (S)-enantiomer<br>55b: (R)-enantiomer |
| 56 | | 2-(1-((6-amino-5-((5-fluoro-pyridin-2-yl)ethynyl)pyrimidin-4-yl)amino)ethyl)-8-methyl-3-phenyl-quinazolin-4(3H)-one<br>56a: (S)-enantiomer<br>56b: (R)-enantiomer |
| 57 | | 2-(1-((6-amino-5-((5-fluoro-pyridin-2-yl)ethynyl)pyrimidin-4-yl)amino)ethyl)-3-(3-butyl-phenyl)-5-chloro-quinazolin-4(3H)-one<br>57a: (S)-enantiomer<br>57b: (R)-enantiomer |

TABLE 1a-continued

Representative Compounds

| # | Name |
|---|---|
| 58 | 2-(1-((6-amino-5-((5-fluoro-pyridin-2-yl)ethynyl)pyrimidin-4-yl)amino)ethyl)-5-chloro-3-(3-(methylsulfonyl)phenyl)quinazolin-4(3H)-one<br>58a: (S)-enantiomer<br>58b: (R)-enantiomer |
| 59 | 2-(1-((6-amino-5-((5-fluoropyridin-2-yl)ethynyl)pyrimidin-4-yl)amino)ethyl)-3-(3-(tert-butyl)phenyl)-5-chloro-quinazolin-4(3H)-one<br>59a: (S)-enantiomer<br>59b: (R)-enantiomer |
| 60 | 3-([1,1'-biphenyl]-3-yl)-2-(1-((6-amino-5-((5-fluoropyridin-2-yl)ethynyl)pyrimidin-4-yl)amino)ethyl)-5-chloro-quinazolin-4(3H)-one<br>60a: (S)-enantiomer<br>60b: (R)-enantiomer |
| 61 | 2-(1-((6-amino-5-((5-fluoro-pyridin-2-yl)ethynyl)pyrimidin-4-yl)amino)ethyl)-5-chloro-3-(3-ethylphenyl)quinazolin-4(3H)-one<br>61a: (S)-enantiomer<br>61b: (R)-enantiomer |
| 62 | 2-(1-((6-amino-5-((5-fluoro-pyridin-2-yl)ethynyl)pyrimidin-4-yl)amino)ethyl)-8-fluoro-5-methyl-3-phenyl-quinazolin-4(3H)-one<br>62a: (S)-enantiomer<br>62b: (R)-enantiomer |
| 63 | 2-(1-((6-amino-5-((3-fluoro-5-methoxyphenyl)ethynyl)pyrimidin-4-yl)amino)ethyl)-5,8-difluoro-3-phenyl-quinazolin-4(3H)-one<br>63a: (S)-enantiomer<br>63b: (R)-enantiomer |

TABLE 1a-continued

Representative Compounds

| # | Structure | Name |
|---|-----------|------|
| 64 | 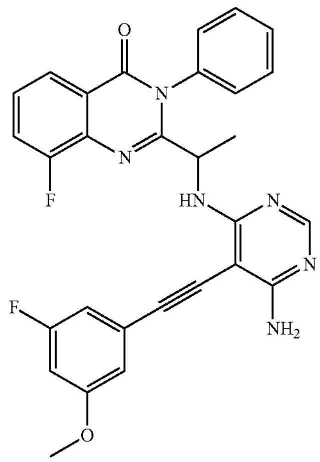 [SMILES: COc1cc(F)cc(C#Cc2c(N)ncnc2NC(C)c2nc3c(F)cccc3c(=O)n2-c2ccccc2)c1] | 2-(1-((6-amino-5-((3-fluoro-5-methoxyphenyl)ethynyl)pyrimidin-4-yl)amino)ethyl)-8-fluoro-3-phenyl-quinazolin-4(3H)-one<br>64a: (S)-enantiomer<br>64b: (R)-enantiomer |
| 65 | 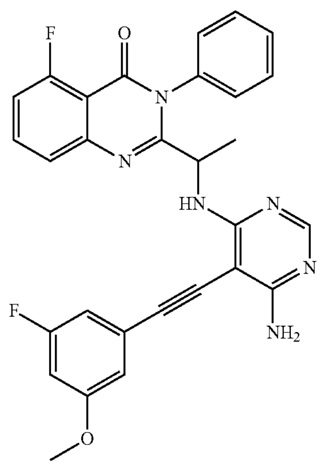 [SMILES: COc1cc(F)cc(C#Cc2c(N)ncnc2NC(C)c2nc3cccc(F)c3c(=O)n2-c2ccccc2)c1] | 2-(1-((6-amino-5-((3-fluoro-5-methoxyphenyl)ethynyl)pyrimidin-4-yl)amino)ethyl)-5-fluoro-3-phenyl-quinazolin-4(3H)-one<br>65a: (S)-enantiomer<br>65b: (R)-enantiomer |
| 66 | 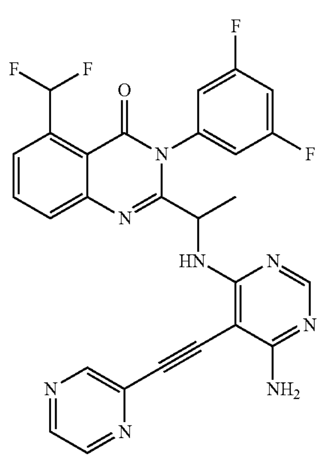 [SMILES: CC(Nc1ncnc(N)c1C#Cc1cnccn1)c1nc2cccc(C(F)F)c2c(=O)n1-c1cc(F)cc(F)c1] | 2-(1-((6-amino-5-(pyrazin-2-ylethynyl)pyrimidin-4-yl)amino)ethyl)-5-(difluoromethyl)-3-(3,5-difluorophenyl)quinazolin-4(3H)-one<br>66a: (S)-enantiomer<br>66b: (R)-enantiomer |
| 67 | | 2-(1-((6-amino-5-((5-fluoropyridin-2-yl)ethynyl)pyrimidin-4-yl)amino)ethyl)-5-(difluoromethyl)-3-phenyl-quinazolin-4(3H)-one<br>67a: (S)-enantiomer<br>67b: (R)-enantiomer |
| 68 | | 2-(1-((6-amino-5-((5-fluoropyridin-2-yl)ethynyl)pyrimidin-4-yl)amino)ethyl)-3-phenyl-5-(trifluoromethyl)quinazolin-4(3H)-one<br>68a: (S)-enantiomer<br>68b: (R)-enantiomer |
| 69 | | 2-(1-((6-amino-5-((5-fluoropyridin-2-yl)ethynyl)pyrimidin-4-yl)amino)ethyl)-5-fluoro-8-methyl-3-phenyl-quinazolin-4(3H)-one<br>69a: (S)-enantiomer<br>69b: (R)-enantiomer |

TABLE 1a-continued

Representative Compounds

| # | Structure | Name |
|---|---|---|
| 70 | 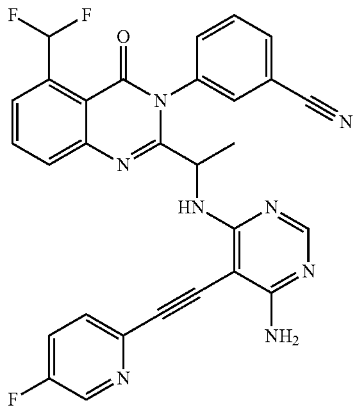 [SMILES: CC(Nc1ncnc(N)c1C#Cc1ccc(F)cn1)c1nc2cccc(C(F)F)c2c(=O)n1-c1cccc(C#N)c1] | 3-(2-(1-((6-amino-5-((5-fluoro-pyridin-2-yl)ethynyl)pyrimidin-4-yl)amino)ethyl)-5-(difluoro-methyl)-4-oxoquinazolin-3(4H)-yl)benzonitrile 70a: (S)-enantiomer 70b: (R)-enantiomer |
| 71 | 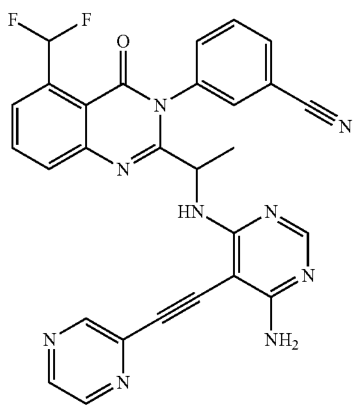 [SMILES: CC(Nc1ncnc(N)c1C#Cc1cnccn1)c1nc2cccc(C(F)F)c2c(=O)n1-c1cccc(C#N)c1] | 3-(2-(1-((6-amino-5-(pyrazin-2-ylethynyl)pyrimidin-4-yl)amino)ethyl)-5-(difluoro-methyl)-4-oxoquinazolin-3(4H)-yl)benzonitrile 71a: (S)-enantiomer 71b: (R)-enantiomer |
| 72 | 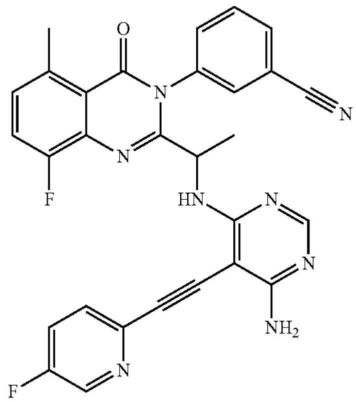 [SMILES: Cc1ccc(F)c2nc(C(C)Nc3ncnc(N)c3C#Cc3ccc(F)cn3)n(-c3cccc(C#N)c3)c(=O)c12] | 3-(2-(1-((6-amino-5-((5-fluoropyridin-2-yl)ethynyl)pyrimidin-4-yl)amino)ethyl)-8-fluoro-5-methyl-4-oxoquinazolin-3(4H)-yl)benzonitrile 72a: (S)-enantiomer 72b: (R)-enantiomer |
| 73 | | 3-(2-(1-((6-amino-5-(pyrazin-2-ylethynyl)pyrimidin-4-yl)amino)ethyl)-8-fluoro-5-methyl-4-oxoquinazolin-3(4H)-yl)benzonitrile 73a: (S)-enantiomer 73b: (R)-enantiomer |
| 74 | | 2-(1-((6-amino-5-(pyrazin-2-ylethynyl)pyrimidin-4-yl)amino)propyl)-5-(difluoro-methyl)-3-(3,5-difluorophenyl)quinazolin-4(3H)-one 74a: (S)-enantiomer 74b: (R)-enantiomer |
| 75 | | 2-(1-((6-amino-5-(pyrazin-2-ylethynyl)pyrimidin-4-yl)amino)ethyl)-8-fluoro-5-methyl-3-phenyl-quinazolin-4(3H)-one 75a: (S)-enantiomer 75b: (R)-enantiomer |

TABLE 1a-continued

Representative Compounds

| # | Structure | Name |
|---|---|---|
| 76 | 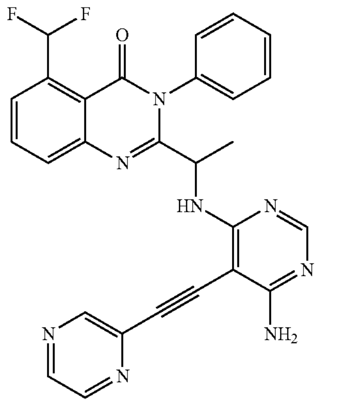 [SMILES: CC(Nc1ncnc(N)c1C#Cc1cnccn1)c1nc2cccc(C(F)F)c2c(=O)n1-c1ccccc1] | 2-(1-((6-amino-5-(pyrazin-2-ylethynyl)pyrimidin-4-yl)amino)ethyl)-5-(difluoromethyl)-3-phenylquinazolin-4(3H)-one<br>76a: (S)-enantiomer<br>76b: (R)-enantiomer |
| 77 | 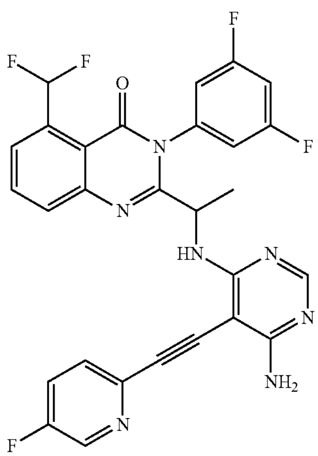 [SMILES: CC(Nc1ncnc(N)c1C#Cc1ccc(F)cn1)c1nc2cccc(C(F)F)c2c(=O)n1-c1cc(F)cc(F)c1] | 2-(1-((6-amino-5-((5-fluoropyridin-2-yl)ethynyl)pyrimidin-4-yl)amino)ethyl)-5-(difluoromethyl)-3-(3,5-difluorophenyl)quinazolin-4(3H)-one<br>77a: (S)-enantiomer<br>77b: (R)-enantiomer |
| 78 | 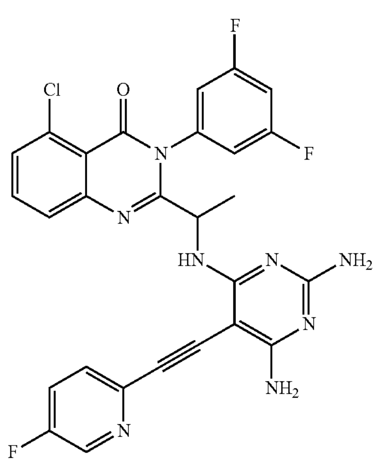 [SMILES: CC(Nc1nc(N)nc(N)c1C#Cc1ccc(F)cn1)c1nc2cccc(Cl)c2c(=O)n1-c1cc(F)cc(F)c1] | 5-chloro-2-(1-((2,6-diamino-5-((5-fluoropyridin-2-yl)ethynyl)pyrimidin-4-yl)amino)ethyl)-3-(3,5-difluorophenyl)quinazolin-4(3H)-one<br>78a: (S)-enantiomer<br>78b: (R)-enantiomer |
| 79 | | 2-(1-((6-amino-5-((3-fluoropyridin-2-yl)ethynyl)pyrimidin-4-yl)amino)ethyl)-5-chloro-3-phenylquinazolin-4(3H)-one<br>79a: (S)-enantiomer<br>79b: (R)-enantiomer |
| 80 | | 2-(1-((6-amino-5-((3-methoxypyridin-2-yl)ethynyl)pyrimidin-4-yl)amino)ethyl)-5-chloro-3-phenylquinazolin-4(3H)-one<br>80a: (S)-enantiomer<br>80b: (R)-enantiomer |
| 81 | | 2-(1-((6-amino-5-((3-fluoropyridin-2-yl)ethynyl)pyrimidin-4-yl)amino)ethyl)-5-chloro-3-(3-methoxy-2-methylphenyl)quinazolin-4(3H)-one<br>81a: (S)-enantiomer<br>81a-1 and a-2: atropisomers<br>81b: (R)-enantiomer<br>81b-1 and b-2: atropisomers |

TABLE 1a-continued

Representative Compounds

| # | Structure | Name |
|---|-----------|------|
| 82 | 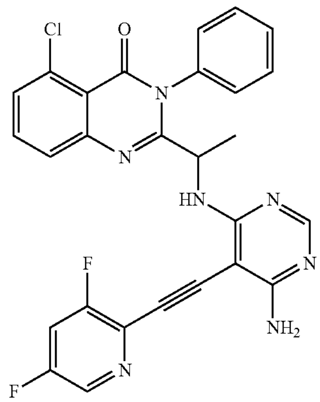 [SMILES: CC(Nc1ncnc(N)c1C#Cc1ncc(F)cc1F)c1nc2cccc(Cl)c2c(=O)n1-c1ccccc1] | 2-(1-((6-amino-5-((3,5-difluoro-pyridin-2-yl)ethynyl)pyrimidin-4-yl)amino)ethyl)-5-chloro-3-phenyl-quinazolin-4(3H)-one<br>82a: (S)-enantiomer<br>82b: (R)-enantiomer |
| 83 | 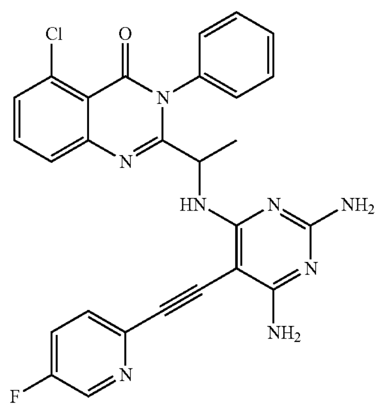 [SMILES: CC(Nc1nc(N)nc(N)c1C#Cc1ccc(F)cn1)c1nc2cccc(Cl)c2c(=O)n1-c1ccccc1] | 5-chloro-2-(1-((2,6-diamino-5-((5-fluoro-pyridin-2-yl)ethynyl)pyrimidin-4-yl)amino)ethyl)-3-phenyl-quinazolin-4(3H)-one<br>83a: (S)-enantiomer<br>83b: (R)-enantiomer |
| 84 | 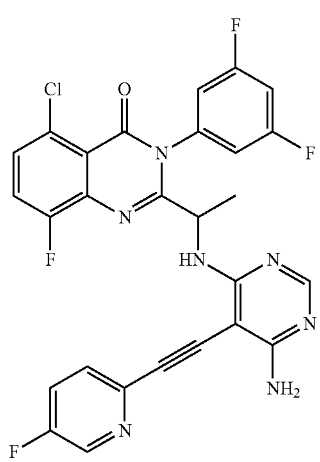 [SMILES: CC(Nc1ncnc(N)c1C#Cc1ccc(F)cn1)c1nc2c(F)ccc(Cl)c2c(=O)n1-c1cc(F)cc(F)c1] | 2-(1-((6-amino-5-((5-fluoro-pyridin-2-yl)ethynyl)pyrimidin-4-yl)amino)ethyl)-5-chloro-3-(3,5-difluorophenyl)-8-fluoro-quinazolin-4(3H)-one<br>84a: (S)-enantiomer<br>84b: (R)-enantiomer |
| 85 | | 2-(1-((6-amino-5-(pyrazin-2-ylethynyl)pyrimidin-4-yl)amino)ethyl)-5-chloro-3-(3,5-difluorophenyl)quinazolin-4(3H)-one<br>85a: (S)-enantiomer<br>85b: (R)-enantiomer |
| 86 | | 2-(1-((6-amino-5-(pyrazin-2-ylethynyl)pyrimidin-4-yl)amino)ethyl)-5-fluoro-3-phenyl-quinazolin-4(3H)-one<br>86a: (S)-enantiomer<br>86b: (R)-enantiomer |
| 87 | | 2-(1-((6-amino-5-(pyrazin-2-ylethynyl)pyrimidin-4-yl)amino)ethyl)-3-(3,5-difluorophenyl)-5-fluoro-quinazolin-4(3H)-one<br>87a: (S)-enantiomer<br>87b: (R)-enantiomer |

TABLE 1a-continued

Representative Compounds

| # | Structure | Name |
|---|---|---|
| 89 | 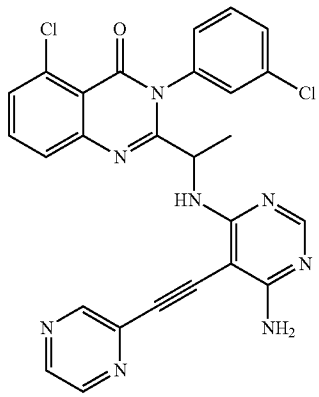 [SMILES: CC(Nc1ncnc(N)c1C#Cc1cnccn1)c1nc2cccc(Cl)c2c(=O)n1-c1cccc(Cl)c1] | 2-(1-((6-amino-5-(pyrazin-2-ylethynyl)pyrimidin-4-yl)amino)ethyl)-5-chloro-3-(3-chlorophenyl)quinazolin-4(3H)-one<br>89a: (S)-enantiomer<br>89b: (R)-enantiomer |
| 90 | 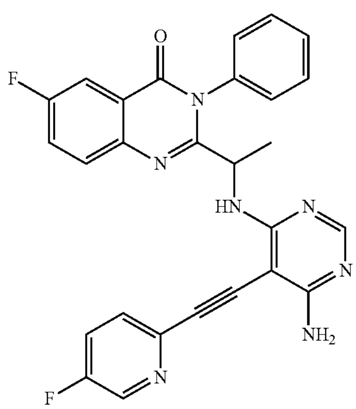 [SMILES: CC(Nc1ncnc(N)c1C#Cc1ccc(F)cn1)c1nc2ccc(F)cc2c(=O)n1-c1ccccc1] | 2-(1-((6-amino-5-((5-fluoro-pyridin-2-yl)ethynyl)pyrimidin-4-yl)amino)ethyl)-6-fluoro-3-phenyl-quinazolin-4(3H)-one<br>90a: (S)-enantiomer<br>90b: (R)-enantiomer |
| 91 | 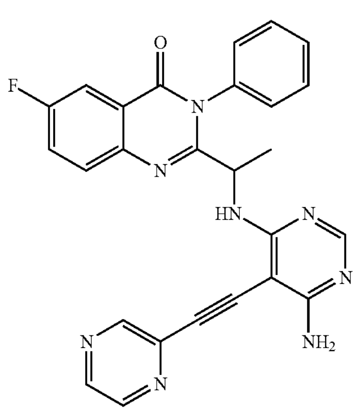 [SMILES: CC(Nc1ncnc(N)c1C#Cc1cnccn1)c1nc2ccc(F)cc2c(=O)n1-c1ccccc1] | 2-(1-((6-amino-5-(pyrazin-2-ylethynyl)pyrimidin-4-yl)amino)ethyl)-6-fluoro-3-phenyl-quinazolin-4(3H)-one<br>91a: (S)-enantiomer<br>91b: (R)-enantiomer |
| 92 | | 3-(2-(1-((6-amino-5-((5-fluoro-pyridin-2-yl)ethynyl)pyrimidin-4-yl)amino)ethyl)-5-chloro-4-oxo-quinazolin-3(4H)-yl)benzonitrile<br>92a: (S)-enantiomer<br>92b: (R)-enantiomer |
| 93 | | 3-(2-(1-((6-amino-5-(pyrazin-2-ylethynyl)pyrimidin-4-yl)amino)ethyl)-5-chloro-4-oxo-quinazolin-3(4H)-yl)benzonitrile<br>93a: (S)-enantiomer<br>93b: (R)-enantiomer |
| 94 | | 3-(2-(1-((6-amino-5-((5-fluoro-pyridin-2-yl)ethynyl)pyrimidin-4-yl)amino)ethyl)-6-fluoro-4-oxoquinazolin-3(4H)-yl)benzonitrile<br>94a: (S)-enantiomer<br>94b: (R)-enantiomer |

TABLE 1a-continued

Representative Compounds

| # | Structure | Name |
|---|---|---|
| 95 | 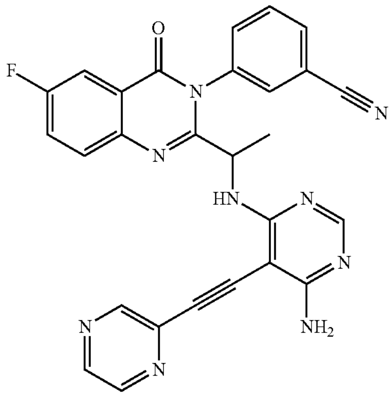 [SMILES: CC(Nc1ncnc(N)c1C#Cc1cnccn1)c1nc2ccc(F)cc2c(=O)n1-c1cccc(C#N)c1] | 3-(2-(1-((6-amino-5-(pyrazin-2-ylethynyl)pyrimidin-4-yl)amino)ethyl)-6-fluoro-4-oxo-quinazolin-3(4H)-yl)benzonitrile<br>95a: (S)-enantiomer<br>95b: (R)-enantiomer |
| 96 | 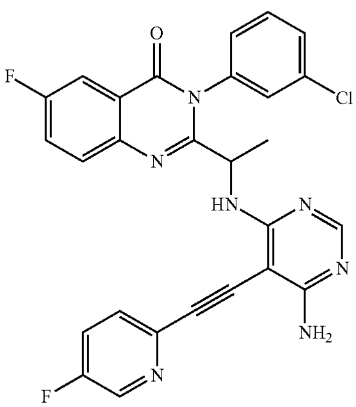 [SMILES: CC(Nc1ncnc(N)c1C#Cc1ccc(F)cn1)c1nc2ccc(F)cc2c(=O)n1-c1cccc(Cl)c1] | 2-(1-((6-amino-5-((5-fluoro-pyridin-2-yl)ethynyl)pyrimidin-4-yl)amino)ethyl)-3-(3-chloro-phenyl)-6-fluoro-quinazolin-4(3H)-one<br>96a: (S)-enantiomer<br>96b: (R)-enantiomer |
| 97 | 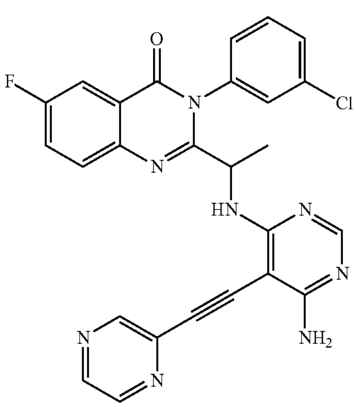 [SMILES: CC(Nc1ncnc(N)c1C#Cc1cnccn1)c1nc2ccc(F)cc2c(=O)n1-c1cccc(Cl)c1] | 2-(1-((6-amino-5-(pyrazin-2-ylethynyl)pyrimidin-4-yl)amino)ethyl)-3-(3-chloro-phenyl)-6-fluoro-quinazolin-4(3H)-one<br>97a: (S)-enantiomer<br>97b: (R)-enantiomer |
| 98 | | 2-(1-((6-amino-5-(pyrazin-2-ylethynyl)pyrimidin-4-yl)amino)ethyl)-5-methyl-3-phenyl-quinazolin-4(3H)-one<br>98a: (S)-enantiomer<br>98b: (R)-enantiomer |
| 99 | | 2-(1-((6-amino-5-((5-fluoro-pyridin-2-yl)ethynyl)pyrimidin-4-yl)amino)ethyl)-5-fluoro-3-(3-fluorophenyl)quinazolin-4(3H)-one<br>99a: (S)-enantiomer<br>99b: (R)-enantiomer |
| 100 | | 2-(1-((6-amino-5-(pyrazin-2-ylethynyl)pyrimidin-4-yl)amino)ethyl)-3-(3,5-difluoro-phenyl)-8-fluoro-quinazolin-4(3H)-one<br>100a: (S)-enantiomer<br>100b: (R)-enantiomer |

TABLE 1a-continued

Representative Compounds

| # | Structure | Name |
|---|---|---|
| 101 | 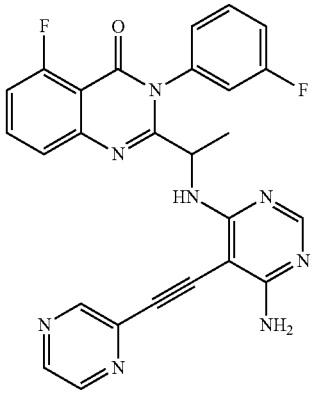 | 2-(1-((6-amino-5-(pyrazin-2-ylethynyl)pyrimidin-4-yl)amino)ethyl)-5-fluoro-3-(3-fluorophenyl)quinazolin-4(3H)-one<br>101a: (S)-enantiomer<br>101b: (R)-enantiomer |
| 102 | 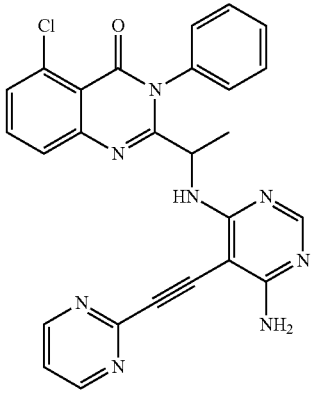 [SMILES: CC(Nc1ncnc(N)c1C#Cc1ncccn1)c1nc2cccc(Cl)c2c(=O)n1-c1ccccc1] | 2-(1-((6-amino-5-(pyrimidin-2-ylethynyl)pyrimidin-4-yl)amino)ethyl)-5-chloro-3-phenyl-quinazolin-4(3H)-one<br>102a: (S)-enantiomer<br>102b: (R)-enantiomer |
| 103 | 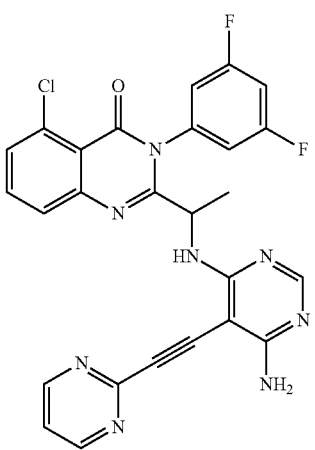 [SMILES: CC(Nc1ncnc(N)c1C#Cc1ncccn1)c1nc2cccc(Cl)c2c(=O)n1-c1cc(F)cc(F)c1] | 2-(1-((6-amino-5-(pyrimidin-2-ylethynyl)pyrimidin-4-yl)amino)ethyl)-5-chloro-3-(3,5-difluorophenyl)quinazolin-4(3H)-one<br>103a: (S)-enantiomer<br>103b: (R)-enantiomer |
| 104 | 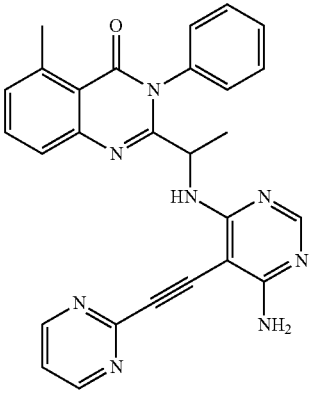 [SMILES: Cc1cccc2nc(C(C)Nc3ncnc(N)c3C#Cc3ncccn3)n(-c3ccccc3)c(=O)c12] | 2-(1-((6-amino-5-(pyrimidin-2-ylethynyl)pyrimidin-4-yl)amino)ethyl)-5-methyl-3-phenyl-quinazolin-4(3H)-one<br>104a: (S)-enantiomer<br>104b: (R)-enantiomer |
| 105 | 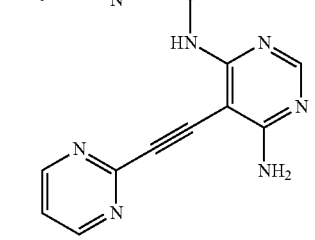 | 2-(1-((6-amino-5-(pyrimidin-2-ylethynyl)pyrimidin-4-yl)amino)ethyl)-3-(3,5-difluorophenyl)-5-methyl-quinazolin-4(3H)-one<br>105a: (S)-enantiomer<br>105b: (R)-enantiomer |
| 106 | 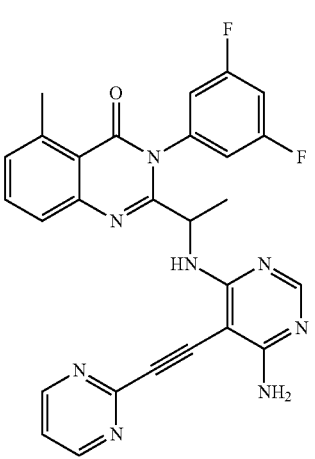 [SMILES: Cc1cccc2nc(C(C)Nc3ncnc(N)c3C#Cc3ncccn3)n(-c3cc(F)cc(F)c3)c(=O)c12] | 2-(1-((6-amino-5-(pyrazin-2-ylethynyl)pyrimidin-4-yl)amino)ethyl)-3-(3-fluorophenyl)-5-methyl-quinazolin-4(3H)-one<br>106a: (S)-enantiomer<br>106b: (R)-enantiomer |

TABLE 1a-continued

Representative Compounds

| # | Structure | Name |
|---|---|---|
| 107 | 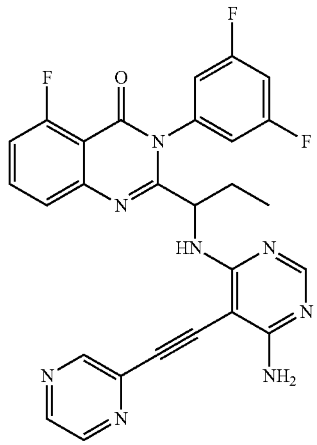 [SMILES: CCC(Nc1ncnc(N)c1C#Cc1cnccn1)c1nc2cccc(F)c2c(=O)n1-c1cc(F)cc(F)c1] | 2-(1-((6-amino-5-(pyrazin-2-ylethynyl)pyrimidin-4-yl)amino)propyl)-3-(3,5-difluorophenyl)-5-fluoroquinazolin-4(3H)-one<br>107a: (S)-enantiomer<br>107b: (R)-enantiomer |
| 108 | 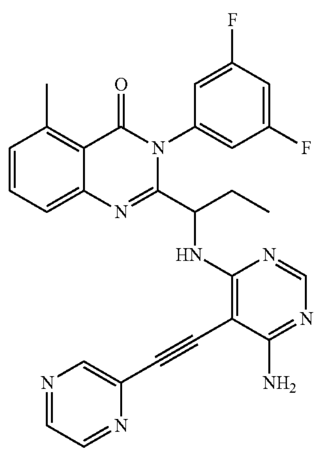 [SMILES: CCC(Nc1ncnc(N)c1C#Cc1cnccn1)c1nc2cccc(C)c2c(=O)n1-c1cc(F)cc(F)c1] | 2-(1-((6-amino-5-(pyrazin-2-ylethynyl)pyrimidin-4-yl)amino)propyl)-3-(3,5-difluorophenyl)-5-methylquinazolin-4(3H)-one<br>108a: (S)-enantiomer<br>108b: (R)-enantiomer |
| 109 | 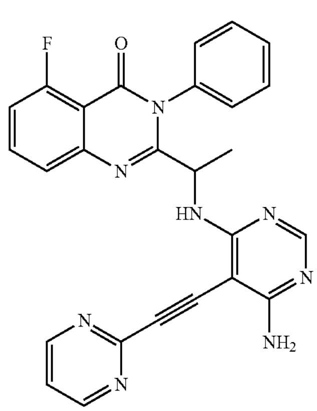 [SMILES: CC(Nc1ncnc(N)c1C#Cc1ncccn1)c1nc2cccc(F)c2c(=O)n1-c1ccccc1] | 2-(1-((6-amino-5-(pyrimidin-2-ylethynyl)pyrimidin-4-yl)amino)ethyl)-5-fluoro-3-phenylquinazolin-4(3H)-one<br>109a: (S)-enantiomer<br>109b: (R)-enantiomer |
| 110 | | 3-(2-(1-((6-amino-5-(phenylethynyl)pyrimidin-4-yl)amino)ethyl)-5-fluoro-4-oxoquinazolin-3(4H)-yl)benzonitrile<br>110a: (S)-enantiomer<br>110b: (R)-enantiomer |
| 111 | | 2-(1-((6-amino-5-(phenylethynyl)pyrimidin-4-yl)amino)ethyl)-5-fluoro-3-(3-fluorophenyl)quinazolin-4(3H)-one<br>111a: (S)-enantiomer<br>111b: (R)-enantiomer |
| 112 | | 2-(1-((6-amino-5-(phenylethynyl)pyrimidin-4-yl)amino)ethyl)-5-(methylsulfonyl)-3-phenylquinazolin-4(3H)-one<br>112a: (S)-enantiomer<br>112b: (R)-enantiomer |

TABLE 1a-continued

Representative Compounds

| # | Structure | Name |
|---|-----------|------|
| 113 | 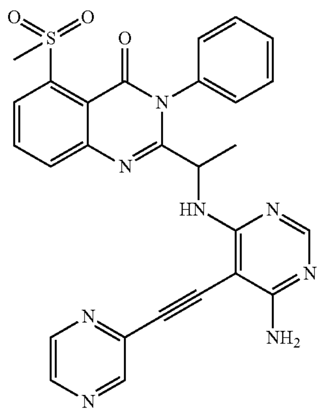 [SMILES: CC(Nc1ncnc(N)c1C#Cc1cnccn1)c1nc2cccc(S(C)(=O)=O)c2c(=O)n1-c1ccccc1] | 2-(1-((6-amino-5-(pyrazin-2-ylethynyl)pyrimidin-4-yl)amino)ethyl)-5-(methylsulfonyl)-3-phenyl-quinazolin-4(3H)-one<br>113a: (S)-enantiomer<br>113b: (R)-enantiomer |
| 114 | 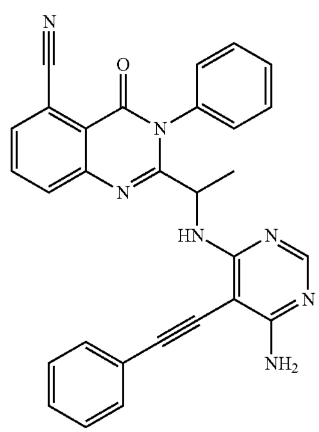 [SMILES: CC(Nc1ncnc(N)c1C#Cc1ccccc1)c1nc2cccc(C#N)c2c(=O)n1-c1ccccc1] | 2-(1-((6-amino-5-(phenyl-ethynyl)pyrimidin-4-yl)amino)ethyl)-4-oxo-3-phenyl-3,4-dihydro-quinazoline-5-carbonitrile<br>114a: (S)-enantiomer<br>114b: (R)-enantiomer |
| 115 | 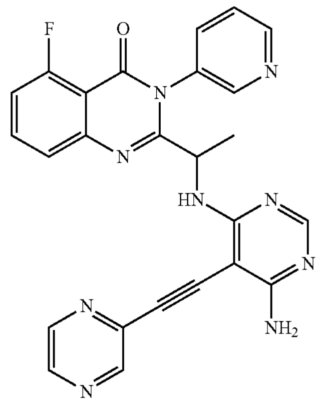 [SMILES: CC(Nc1ncnc(N)c1C#Cc1cnccn1)c1nc2cccc(F)c2c(=O)n1-c1cccnc1] | 2-(1-((6-amino-5-(pyrazin-2-ylethynyl)pyrimidin-4-yl)amino)ethyl)-5-fluoro-3-(pyridin-3-yl)quinazolin-4(3H)-one<br>115a: (S)-enantiomer<br>115b: (R)-enantiomer |
| 116 | | 2-(1-((6-amino-5-(phenyl-ethynyl)pyrimidin-4-yl)amino)ethyl)-5-fluoro-3-(pyridin-3-yl)quinazolin-4(3H)-one<br>116a: (S)-enantiomer<br>116b: (R)-enantiomer |
| 117 | | 2-(1-((6-amino-5-(pyrimidin-2-ylethynyl)pyrimidin-4-yl)amino)ethyl)-5-chloro-3-(pyridin-3-yl)quinazolin-4(3H)-one<br>117a: (S)-enantiomer<br>117b: (R)-enantiomer |
| 118 | | 2-(1-((6-amino-5-(pyrazin-2-ylethynyl)pyrimidin-4-yl)amino)ethyl)-5-chloro-3-(pyridin-3-yl)quinazolin-4(3H)-one<br>118a: (S)-enantiomer<br>118b: (R)-enantiomer |

TABLE 1a-continued

Representative Compounds

| # | Structure | Name |
|---|---|---|
| 119 | 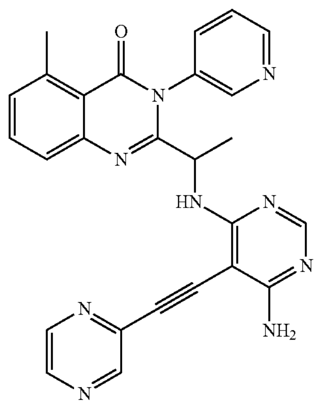 [SMILES: Cc1cccc2nc(C(C)Nc3ncnc(N)c3C#Cc3cnccn3)n(-c3cccnc3)c(=O)c12] | 2-(1-((6-amino-5-(pyrazin-2-ylethynyl)pyrimidin-4-yl)amino)ethyl)-5-methyl-3-(pyridin-3-yl)quinazolin-4(3H)-one<br>119a: (S)-enantiomer<br>119b: (R)-enantiomer |
| 120 | 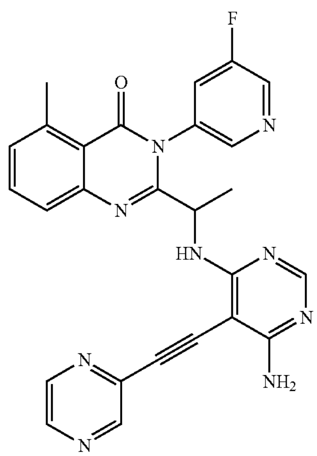 [SMILES: Cc1cccc2nc(C(C)Nc3ncnc(N)c3C#Cc3cnccn3)n(-c3cncc(F)c3)c(=O)c12] | 2-(1-((6-amino-5-(pyrazin-2-ylethynyl)pyrimidin-4-yl)amino)ethyl)-3-(5-fluoropyridin-3-yl)-5-methylquinazolin-4(3H)-one<br>120a: (S)-enantiomer<br>120b: (R)-enantiomer |
| 121 | 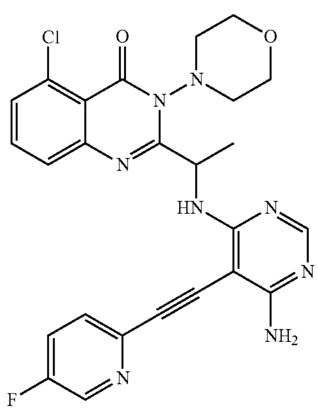 [SMILES: CC(Nc1ncnc(N)c1C#Cc1ccc(F)cn1)c1nc2cccc(Cl)c2c(=O)n1N1CCOCC1] | 2-(1-((6-amino-5-((5-fluoropyridin-2-yl)ethynyl)pyrimidin-4-yl)amino)ethyl)-5-chloro-3-morpholinoquinazolin-4(3H)-one<br>121a: (S)-enantiomer<br>121b: (R)-enantiomer |
| 122 | | 2-(1-((6-amino-5-((3-fluoro-5-methoxyphenyl)ethynyl)pyrimidin-4-yl)amino)ethyl)-5-chloro-3-morpholinoquinazolin-4(3H)-one<br>122a: (S)-enantiomer<br>122b: (R)-enantiomer |
| 123 | | N-(3-(2-(1-((6-amino-5-(pyrazin-2-ylethynyl)pyrimidin-4-yl)amino)ethyl)-5-chloro-4-oxoquinazolin-3(4H)-yl)benzyl)methanesulfonamide<br>123a: (S)-enantiomer<br>123b: (R)-enantiomer |
| 124 | | 2-(1-((6-amino-5-(pyrazin-2-ylethynyl)pyrimidin-4-yl)amino)ethyl)-5-chloro-3-((1R,5S)-8-methyl-8-azabicyclo[3.2.1]octan-3-yl)quinazolin-4(3H)-one<br>124a: (S)-enantiomer<br>124b: (R)-enantiomer |

TABLE 1a-continued

Representative Compounds

| # | Structure | Name |
|---|---|---|
| 125 | 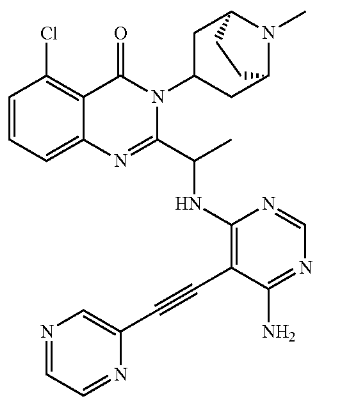 | 2-(1-((6-amino-5-(pyrazin-2-ylethynyl)pyrimidin-4-yl)amino)ethyl)-5-chloro-3-((1R,5S)-8-methyl-8-azabicyclo[3.2.1]octan-3-yl)quinazolin-4(3H)-one<br>125a: (S)-enantiomer<br>125b: (R)-enantiomer |
| 126 | 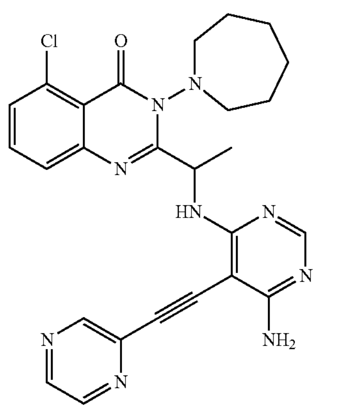 [SMILES: CC(Nc1ncnc(N)c1C#Cc1cnccn1)c1nc2cccc(Cl)c2c(=O)n1N1CCCCCC1] | 2-(1-((6-amino-5-(pyrazin-2-ylethynyl)pyrimidin-4-yl)amino)ethyl)-3-(azepan-1-yl)-5-chloroquinazolin-4(3H)-one<br>126a: (S)-enantiomer<br>126b: (R)-enantiomer |
| 127 | 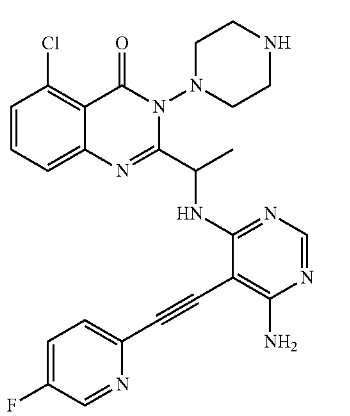 [SMILES: CC(Nc1ncnc(N)c1C#Cc1ccc(F)cn1)c1nc2cccc(Cl)c2c(=O)n1N1CCNCC1] | 2-(1-((6-amino-5-((5-fluoropyridin-2-yl)ethynyl)pyrimidin-4-yl)amino)ethyl)-5-chloro-3-(piperazin-1-yl)quinazolin-4(3H)-one<br>127a: (S)-enantiomer<br>127b: (R)-enantiomer |
| 128 | | N-(3-(2-(1-((6-amino-5-((5-fluoropyridin-2-yl)ethynyl)pyrimidin-4-yl)amino)ethyl)-5-methyl-4-oxoquinazolin-3(4H)-yl)benzyl)-N-methylmethanesulfonamide<br>128a: (S)-enantiomer<br>128b: (R)-enantiomer |
| 129 | | (S)-N-(3-(2-(1-((6-amino-5-((5-fluoropyridin-2-yl)ethynyl)pyrimidin-4-yl)(methyl)amino)ethyl)-5-chloro-4-oxoquinazolin-3(4H)-yl)benzyl)-N-methylmethanesulfonamide<br>129a: (S)-enantiomer<br>129b: (R)-enantiomer |
| 130 | | N-(3-(2-(1-((6-amino-5-((5-fluoropyridin-2-yl)ethynyl)pyrimidin-4-yl)amino)ethyl)-5-chloro-4-oxoquinazolin-3(4H)-yl)benzyl)methanesulfonamide<br>130a: (S)-enantiomer<br>130b: (R)-enantiomer |

TABLE 1a-continued

Representative Compounds

| # | Structure | Name |
|---|---|---|
| 131 | 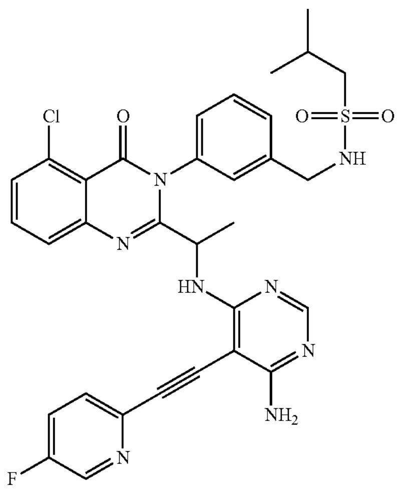 [SMILES: CC(C)CS(=O)(=O)NCc1cccc(-n2c(C(C)Nc3ncnc(N)c3C#Cc3ccc(F)cn3)nc3cccc(Cl)c3c2=O)c1] | N-(3-(2-(1-((6-amino-5-((5-fluoro-pyridin-2-yl)ethynyl)pyrimidin-4-yl)amino)ethyl)-5-chloro-4-oxoquinazolin-3(4H)-yl)benzyl)-2-methylpropane-1-sulfonamide<br>131a: (S)-enantiomer<br>131b: (R)-enantiomer |
| 132 | 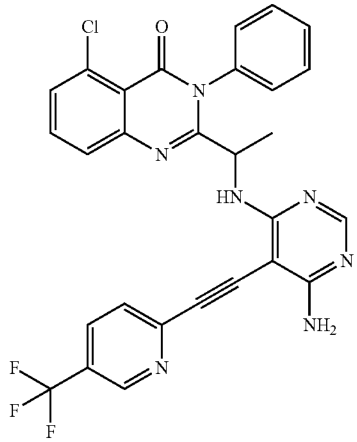 [SMILES: CC(Nc1ncnc(N)c1C#Cc1ccc(C(F)(F)F)cn1)c1nc2cccc(Cl)c2c(=O)n1-c1ccccc1] | 2-(1-((6-amino-5-((5-(trifluoromethyl)pyridin-2-yl)ethynyl)pyrimidin-4-yl)amino)ethyl)-5-chloro-3-phenyl-quinazolin-4(3H)-one<br>132a: (S)-enantiomer<br>132b: (R)-enantiomer |
| 133 | 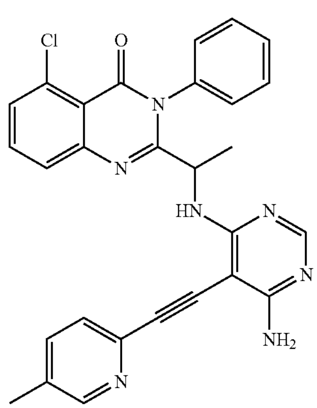 [SMILES: Cc1ccc(C#Cc2c(N)ncnc2NC(C)c2nc3cccc(Cl)c3c(=O)n2-c2ccccc2)nc1] | 2-(1-((6-amino-5-((5-methyl-pyridin-2-yl)ethynyl)pyrimidin-4-yl)amino)ethyl)-5-chloro-3-phenyl-quinazolin-4(3H)-one<br>133a: (S)-enantiomer<br>133b: (R)-enantiomer |
| 134 | 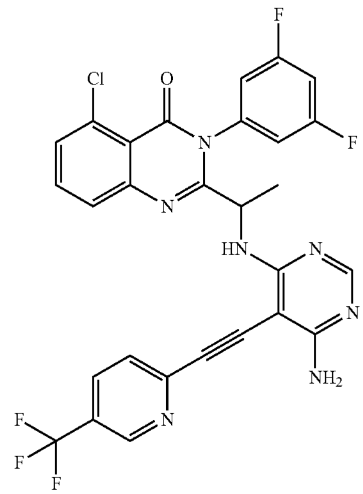 [SMILES: CC(Nc1ncnc(N)c1C#Cc1ccc(C(F)(F)F)cn1)c1nc2cccc(Cl)c2c(=O)n1-c1cc(F)cc(F)c1] | 2-(1-((6-amino-5-((5-(trifluoromethyl)pyridin-2-yl)ethynyl)pyrimidin-4-yl)amino)ethyl)-5-chloro-3-(3,5-difluorophenyl)quinazolin-4(3H)-one<br>134a: (S)-enantiomer<br>134b: (R)-enantiomer |
| 135 | 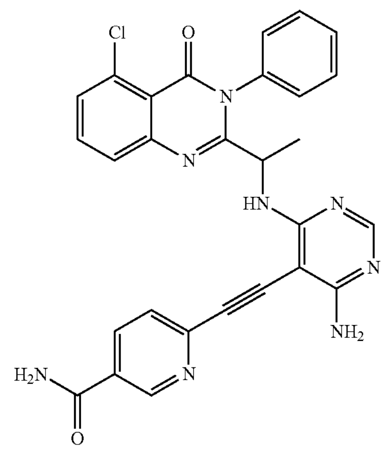 [SMILES: CC(Nc1ncnc(N)c1C#Cc1ccc(C(N)=O)cn1)c1nc2cccc(Cl)c2c(=O)n1-c1ccccc1] | 6-((4-amino-6-((1-(5-chloro-4-oxo-3-phenyl-3,4-dihydro-quinazolin-2-yl)ethyl)amino)pyrimidin-5-yl)ethynyl)nicotinamide<br>135a: (S)-enantiomer<br>135b: (R)-enantiomer |
| 136 | 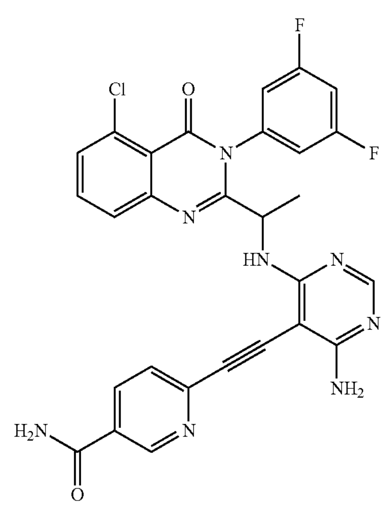 [SMILES: CC(Nc1ncnc(N)c1C#Cc1ccc(C(N)=O)cn1)c1nc2cccc(Cl)c2c(=O)n1-c1cc(F)cc(F)c1] | 6-((4-amino-6-((1-(5-chloro-3-(3,5-difluoro-phenyl)-4-oxo-3,4-dihydro-quinazolin-2-yl)ethyl)amino)pyrimidin-5-yl)ethynyl)nicotinamide<br>136a: (S)-enantiomer<br>136b: (R)-enantiomer |

TABLE 1a-continued

Representative Compounds

| # | Structure | Name |
|---|---|---|
| 137 | 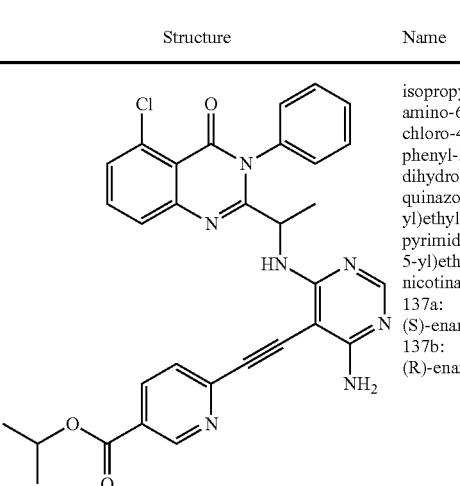 | isopropyl 6-((4-amino-6-((1-(5-chloro-4-oxo-3-phenyl-3,4-dihydro-quinazolin-2-yl)ethyl)amino)pyrimidin-5-yl)ethynyl)nicotinate 137a: (S)-enantiomer 137b: (R)-enantiomer |
| 138 | 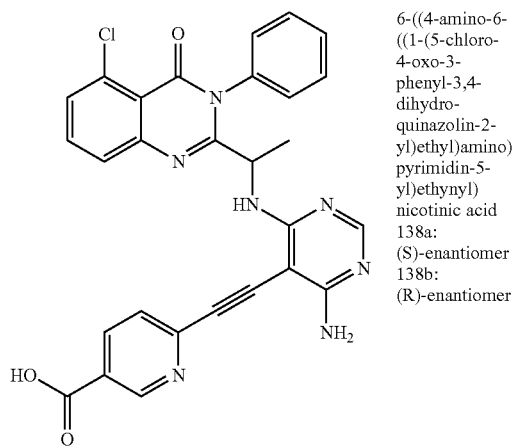 | 6-((4-amino-6-((1-(5-chloro-4-oxo-3-phenyl-3,4-dihydro-quinazolin-2-yl)ethyl)amino)pyrimidin-5-yl)ethynyl)nicotinic acid 138a: (S)-enantiomer 138b: (R)-enantiomer |
| 139 | 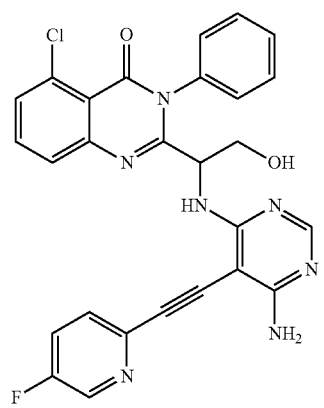 [SMILES: Nc1ncnc(NC(CO)c2nc3cccc(Cl)c3c(=O)n2-c2ccccc2)c1C#Cc1ccc(F)cn1] | 2-(1-((6-amino-5-((5-fluoro-pyridin-2-yl)ethynyl)pyrimidin-4-yl)amino)-2-hydroxyethyl)-5-chloro-3-phenyl-quinazolin-4(3H)-one 139a: (S)-enantiomer 139b: (R)-enantiomer |

TABLE 1a-continued

Representative Compounds

| # | Structure | Name |
|---|---|---|
| 140 | | 2-(1-((6-amino-5-((5-fluoro-6-methylpyridin-2-yl)ethynyl)pyrimidin-4-yl)amino)ethyl)-5-chloro-3-phenyl-quinazolin-4(3H)-one 140a: (S)-enantiomer 140b: (R)-enantiomer |
| 141 | | 2-(1-((6-amino-5-((6-methyl-pyridin-2-yl)ethynyl)pyrimidin-4-yl)amino)ethyl)-5-chloro-3-phenyl-quinazolin-4(3H)-one 141a: (S)-enantiomer 141b: (R)-enantiomer |
| 142 | 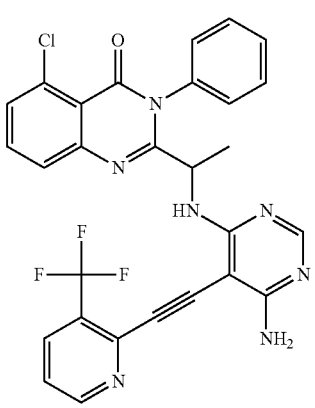 [SMILES: CC(Nc1ncnc(N)c1C#Cc1ncccc1C(F)(F)F)c1nc2cccc(Cl)c2c(=O)n1-c1ccccc1] | 2-(1-((6-amino-5-((3-(trifluoro-methyl)pyridin-2-yl)ethynyl)pyrimidin-4-yl)amino)ethyl)-5-chloro-3-phenyl-quinazolin-4(3H)-one 142a: (S)-enantiomer 142b: (R)-enantiomer |

TABLE 1a-continued

Representative Compounds

| # | Structure | Name |
|---|---|---|
| 143 | 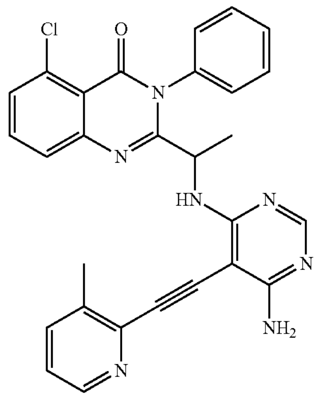 [SMILES: Cc1cccnc1C#Cc1c(N)ncnc1NC(C)c1nc2cccc(Cl)c2c(=O)n1-c1ccccc1] | 2-(1-((6-amino-5-((3-methyl-pyridin-2-yl)ethynyl)pyrimidin-4-yl)amino)ethyl)-5-chloro-3-phenyl-quinazolin-4(3H)-one<br>143a: (S)-enantiomer<br>143b: (R)-enantiomer |
| 144 | 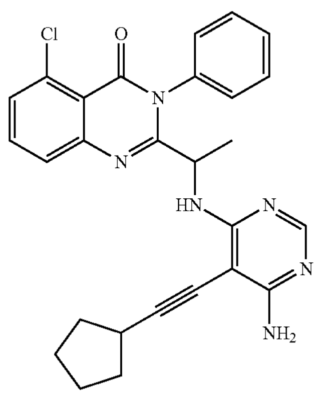 [SMILES: CC(Nc1ncnc(N)c1C#CC1CCCC1)c1nc2cccc(Cl)c2c(=O)n1-c1ccccc1] | 2-(1-((6-amino-5-(cyclopentyl-ethynyl)pyrimidin-4-yl)amino)ethyl)-5-chloro-3-phenyl-quinazolin-4(3H)-one<br>144a: (S)-enantiomer<br>144b: (R)-enantiomer |
| 145 | 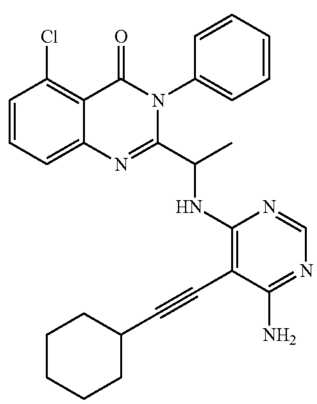 [SMILES: CC(Nc1ncnc(N)c1C#CC1CCCCC1)c1nc2cccc(Cl)c2c(=O)n1-c1ccccc1] | 2-(1-((6-amino-5-(cyclohexyl-ethynyl)pyrimidin-4-yl)amino)ethyl)-5-chloro-3-phenyl-quinazolin-4(3H)-one<br>145a: (S)-enantiomer<br>145b: (R)-enantiomer |
| 146 | | 2-(1-((6-amino-5-((5-fluoro-pyridin-2-yl)ethynyl)pyrimidin-4-yl)amino)-2-methoxyethyl)-5-chloro-3-(3,5-difluoro-phenyl)quinazolin-4(3H)-one<br>146a: (S)-enantiomer<br>146b: (R)-enantiomer |
| 147 | | 2-(1-((6-amino-5-((4-methyl-pyridin-2-yl)ethynyl)pyrimidin-4-yl)amino)ethyl)-5-chloro-3-phenyl-quinazolin-4(3H)-one<br>147a: (S)-enantiomer<br>147b: (R)-enantiomer |
| 148 | | 2-(1-((6-amino-5-((4-(trifluoro-methyl)pyridin-2-yl)ethynyl)pyrimidin-4-yl)amino)ethyl)-5-chloro-3-phenyl-quinazolin-4(3H)-one<br>148a: (S)-enantiomer<br>148b: (R)-enantiomer |

TABLE 1a-continued

Representative Compounds

| # | Structure | Name |
|---|---|---|
| 149 | 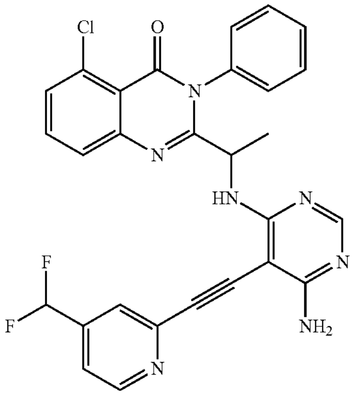 [SMILES: CC(Nc1ncnc(N)c1C#Cc1cc(C(F)F)ccn1)c1nc2cccc(Cl)c2c(=O)n1-c1ccccc1] | 2-(1-((6-amino-5-((4-(difluoromethyl)pyridin-2-yl)ethynyl)pyrimidin-4-yl)amino)ethyl)-5-chloro-3-phenyl-quinazolin-4(3H)-one<br>149a: (S)-enantiomer<br>149b: (R)-enantiomer |
| 150 | 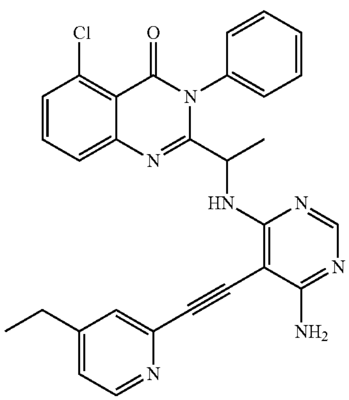 [SMILES: CCc1ccnc(C#Cc2c(N)ncnc2NC(C)c2nc3cccc(Cl)c3c(=O)n2-c2ccccc2)c1] | 2-(1-((6-amino-5-((4-ethyl-pyridin-2-yl)ethynyl)pyrimidin-4-yl)amino)ethyl)-5-chloro-3-phenyl-quinazolin-4(3H)-one<br>150a: (S)-enantiomer<br>150b: (R)-enantiomer |
| 151 | 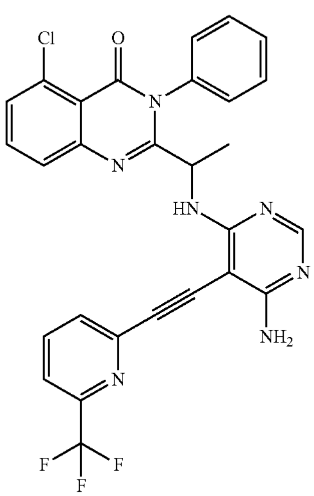 [SMILES: CC(Nc1ncnc(N)c1C#Cc1cccc(C(F)(F)F)n1)c1nc2cccc(Cl)c2c(=O)n1-c1ccccc1] | 2-(1-((6-amino-5-((6-(trifluoromethyl)pyridin-2-yl)ethynyl)pyrimidin-4-yl)amino)ethyl)-5-chloro-3-phenyl-quinazolin-4(3H)-one<br>151a: (S)-enantiomer<br>151b: (R)-enantiomer |
| 152 | | 2-(1-((5-((3-acetylpyridin-2-yl)ethynyl)-6-amino-pyrimidin-4-yl)amino)ethyl)-5-chloro-3-phenyl-quinazolin-4(3H)-one<br>152a: (S)-enantiomer<br>152b: (R)-enantiomer |
| 153 | | 2-(1-((5-((6-acetylpyridin-2-yl)ethynyl)-6-amino-pyrimidin-4-yl)amino)ethyl)-5-chloro-3-phenyl-quinazolin-4(3H)-one<br>153a: (S)-enantiomer<br>153b: (R)-enantiomer |
| 154 | | 2-(1-((6-amino-5-((4-(hydroxymethyl)pyridin-2-yl)ethynyl)pyrimidin-4-yl)amino)ethyl)-5-chloro-3-phenyl-quinazolin-4(3H)-one<br>154a: (S)-enantiomer<br>154b: (R)-enantiomer |

TABLE 1a-continued

Representative Compounds

| # | Structure | Name |
|---|---|---|
| 155 | 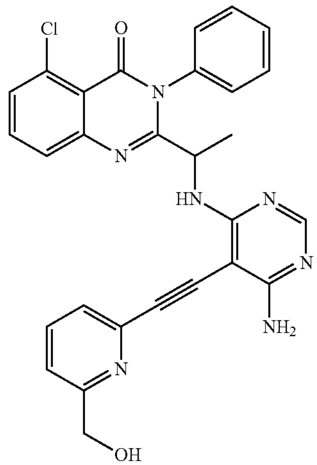 [SMILES: CC(Nc1ncnc(N)c1C#Cc1cccc(CO)n1)c1nc2cccc(Cl)c2c(=O)n1-c1ccccc1] | 2-(1-((6-amino-5-((6-(hydroxy-methyl)pyridin-2-yl)ethynyl)pyrimidin-4-yl)amino)ethyl)-5-chloro-3-phenyl-quinazolin-4(3H)-one<br>155a: (S)-enantiomer<br>155b: (R)-enantiomer |
| 156 | 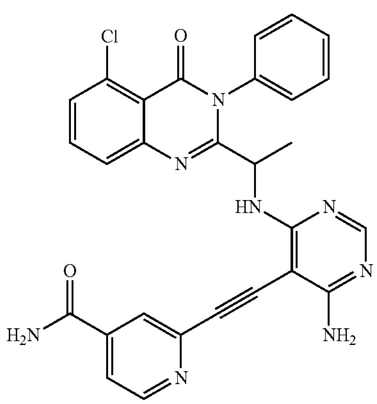 [SMILES: CC(Nc1ncnc(N)c1C#Cc1cc(C(N)=O)ccn1)c1nc2cccc(Cl)c2c(=O)n1-c1ccccc1] | 2-((4-amino-6-((1-(5-chloro-4-oxo-3-phenyl-3,4-dihydro-quinazolin-2-yl)ethyl)amino)pyrimidin-5-yl)ethynyl)isonicotinamide<br>156a: (S)-enantiomer<br>156b: (R)-enantiomer |
| 157 | 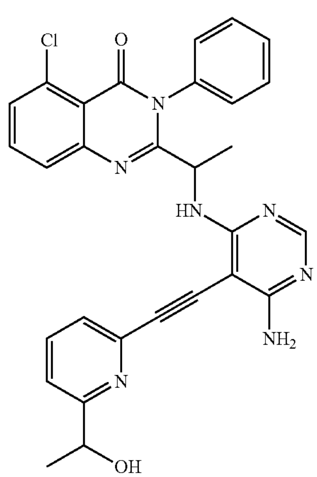 [SMILES: CC(O)c1cccc(C#Cc2c(N)ncnc2NC(C)c2nc3cccc(Cl)c3c(=O)n2-c2ccccc2)n1] | 2-(1-((6-amino-5-((6-(1-hydroxyethyl)pyridin-2-yl)ethynyl)pyrimidin-4-yl)amino)ethyl)-5-chloro-3-phenyl-quinazolin-4(3H)-one<br>157a: (S)-enantiomer<br>157b: (R)-enantiomer |
| 158 | | methyl 2-((4-amino-6-((1-(5-chloro-4-oxo-3-phenyl-3,4-dihydro-quinazolin-2-yl)ethyl)amino)pyrimidin-5-yl)ethynyl)isonicotinate<br>158a: (S)-enantiomer<br>158b: (R)-enantiomer |
| 159 | | 2-(1-((6-amino-5-((6-(amino-methyl)pyridin-2-yl)ethynyl)pyrimidin-4-yl)amino)ethyl)-5-chloro-3-phenyl-quinazolin-4(3H)-one<br>159a: (S)-enantiomer<br>159b: (R)-enantiomer |
| 160 | | 2-((4-amino-6-((1-(5-chloro-4-oxo-3-phenyl-3,4-dihydro-quinazolin-2-yl)ethyl)amino)pyrimidin-5-yl)ethynyl)isonicotinic acid<br>160a: (S)-enantiomer<br>160b: (R)-enantiomer |

TABLE 1a-continued

Representative Compounds

| # | Structure | Name |
|---|---|---|
| 161 | 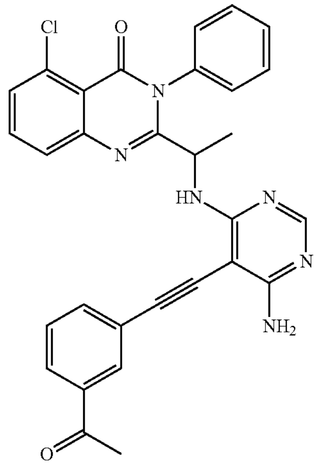 [SMILES: CC(=O)c1cccc(C#Cc2c(N)ncnc2NC(C)c2nc3cccc(Cl)c3c(=O)n2-c2ccccc2)c1] | 2-(1-((5-((3-acetylphenyl)ethynyl)-6-amino-pyrimidin-4-yl)amino)ethyl)-5-chloro-3-phenyl-quinazolin-4(3H)-one<br>161a: (S)-enantiomer<br>161b: (R)-enantiomer |
| 162 | 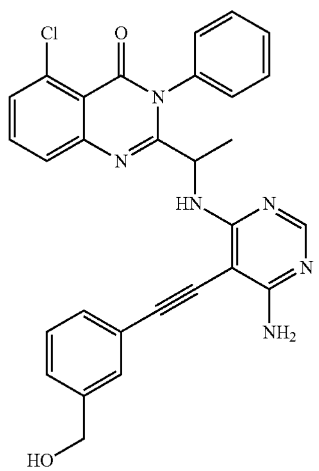 [SMILES: CC(Nc1ncnc(N)c1C#Cc1cccc(CO)c1)c1nc2cccc(Cl)c2c(=O)n1-c1ccccc1] | 2-(1-((6-amino-5-((3-(hydroxy-methyl)phenyl)ethynyl)pyrimidin-4-yl)amino)ethyl)-5-chloro-3-phenyl-quinazolin-4(3H)-one<br>162a: (S)-enantiomer<br>162b: (R)-enantiomer |
| 163 | 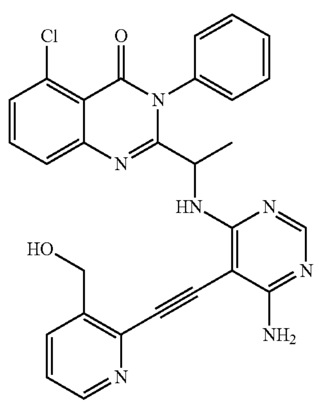 [SMILES: CC(Nc1ncnc(N)c1C#Cc1ncccc1CO)c1nc2cccc(Cl)c2c(=O)n1-c1ccccc1] | 2-(1-((6-amino-5-((3-(hydroxy-methyl)pyridin-2-yl)ethynyl)pyrimidin-4-yl)amino)ethyl)-5-chloro-3-phenyl-quinazolin-4(3H)-one<br>163a: (S)-enantiomer<br>163b: (R)-enantiomer |
| 164 | | 2-(1-((6-amino-5-((5-methyl-pyridin-2-yl)ethynyl)pyrimidin-4-yl)amino)ethyl)-5-chloro-3-(3,5-difluorophenyl)quinazolin-4(3H)-one<br>164a: (S)-enantiomer<br>164b: (R)-enantiomer |
| 165 | | 2-(1-((6-amino-5-((5-fluoro-pyridin-2-yl)ethynyl)pyrimidin-4-yl)amino)ethyl)-5-chloro-3-(3-((methylamino)methyl)phenyl)quinazolin-4(3H)-one<br>165a: (S)-enantiomer<br>165b: (R)-enantiomer |
| 166 | | 2-(1-((6-amino-5-((5-fluoro-pyridin-2-yl)ethynyl)pyrimidin-4-yl)amino)ethyl)-3-(azetidin-3-yl)-5-chloro-quinazolin-4(3H)-one<br>166a: (S)-enantiomer<br>166b: (R)-enantiomer |

TABLE 1a-continued

Representative Compounds

| # | Structure | Name |
|---|-----------|------|
| 167 | 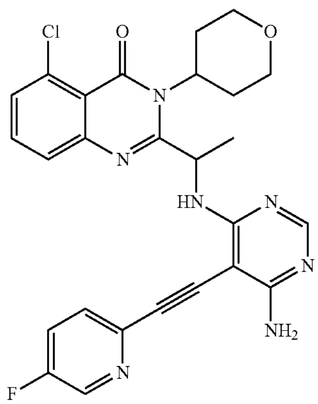 [SMILES: CC(Nc1ncnc(N)c1C#Cc1ccc(F)cn1)c1nc2cccc(Cl)c2c(=O)n1C1CCOCC1] | 2-(1-(((6-amino-5-((5-fluoro-pyridin-2-yl)ethynyl) pyrimidin-4-yl)amino)ethyl)-5-chloro-3-(tetrahydro-2H-pyran-4-yl) quinazolin-4(3H)-one 167a: (S)-enantiomer 167b: (R)-enantiomer |

Provided are also compounds of formula (I), (IA), (IB), (IC), or (II), or pharmaceutically acceptable salts, prodrugs, or solvates thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds of formula (I), (IA), (IB), (IC), or (II), or pharmaceutically acceptable salts, prodrugs, or solvates thereof, when administered to a mammal. See, e.g., Foster, "Deuterium Isotope Effects in Studies of Drug Metabolism", Trends Pharmacol. Sci., 5(12): 524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds of formula (I), (IA), (IB), (IC), or (II).

"Pharmaceutically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds of formula (I), (IA), (IB), (IC), or (II) are also provided. Hydrates of the compounds of formula (I), (IA), (IB), (IC), or (II) are also provided.

A "prodrug" includes any compound that becomes a compound of formula (I), (IA), (IB), (IC), or (II) when administered to a subject, e.g., upon metabolic processing of the prodrug.

In certain embodiments, provided are optical isomers, racemates, or other mixtures thereof, of the compounds of formula (I), (IA), (IB), (IC), or (II), or pharmaceutically acceptable salts, prodrugs, or solvates thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the compounds of formula (I), (IA), (IB), (IC), or (II), or pharmaceutically acceptable salts, prodrugs, or solvates thereof with carbon-carbon double bonds. Provided are also all tautomeric forms of the compounds of formula (I), (IA), (IB), (IC), or (II), or pharmaceutically acceptable salts, prodrugs, or solvates thereof.

Compositions provided herein that include a compound of formula (I), (IA), (IB), (IC), or (II), or a pharmaceutically acceptable salt, prodrug, or solvate thereof, may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided herein are also crystalline and amorphous forms of the compounds of formula (I), (IA), (IB), (IC), or (II), or pharmaceutically acceptable salts, prodrugs, or solvates thereof.

In certain embodiments, provided are also chelates, non-covalent complexes, and mixtures thereof, of the compounds of formula (I), (IA), (IB), (IC), or (II), or pharmaceutically acceptable salts, prodrugs, or solvates thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The compounds of formula (I), (IA), (IB), (IC), or (II), or a pharmaceutically acceptable salt, prodrug, or solvate thereof may be used for the treatment of diseases and/or conditions mediated by PI3K isomers, such as PI3Kδ. Thus, provided herein are methods for inhibiting one or more PI3K isomers. In one embodiment, provided are methods for inhibiting PI3Kδ activity using a compound of formula (I), (IA), (IB), (IC), or (II), or a pharmaceutically acceptable salt, prodrug, or solvate thereof. The PI3K isomers may be selectively or specifically inhibited. Additionally, the compounds may be used to inhibit PI3K activity therapeutically or prophylactically.

In some embodiments, the methods include administering a compound of formula (I), (IA), (IB), (IC), or (II), or a pharmaceutically acceptable salt, prodrug, or solvate thereof, in a therapeutically effective amount to a subject (including a human) in need thereof. The method can be employed to treat a subject who has or is believed to have a disease or condition whose symptoms or pathology is mediated by PI3Kδ expression or activity.

"Treatment" or "treating" is an approach for obtaining beneficial or desired results including clinical results. Beneficial or desired clinical results may include one or more of the following:

a) inhibiting the disease or condition (e.g., decreasing one or more symptoms resulting from the disease or condition, and/or diminishing the extent of the disease or condition);

b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" of a compound of formula (I), (IA), (IB), (IC), or (II), or a pharmaceutically acceptable salt, prodrug, or solvate thereof, means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of PI3K isomers" or variants thereof refer to a decrease in activity in any PI3K isomer (e.g., alpha, beta, gamma, or delta) as a direct or indirect response to the presence of a compound of formula (I), (IA), (IB), (IC), or (II), or a pharmaceutically acceptable salt, prodrug, or solvent thereof, relative to the activity of PI3K in the absence of the compound of formula (I), (IA), (IB), (IC), or (II), or a pharmaceutically acceptable salt, prodrug, or solvent thereof. "Inhibition of PI3Kδ activity" or variants thereof refer to a decrease in PI3Kδ activity as a direct or indirect response to the presence of a compound of formula (I), (IA), (IB), (IC), or (II), or a pharmaceutically acceptable salt, prodrug, or solvate thereof, relative to the activity of PI3Kδ in the absence of the compound of formula (I), (IA), (IB), (IC), or (II), or a pharmaceutically acceptable salt, prodrug, or solvate thereof. In some embodiments, the inhibition of PI3Kδ activity may be compared in the same subject prior to treatment, or other subjects not receiving the treatment.

Without wishing to be bound to any theory, the decrease in PI3Kδ activity may be due to the direct interaction of the compound with PI3Kδ, or due to the interaction of the compounds described herein with one or more other factors that in turn affect PI3Kδ activity. For example, the presence of the compounds of formula (I), (IA), (IB), (IC), or (II), or a pharmaceutically acceptable salt, prodrug, or solvate thereof, may decrease PI3Kδ activity by directly binding to the PI3Kδ, by causing (directly or indirectly) another factor to decrease PI3Kδ activity, or by (directly or indirectly) decreasing the amount of PI3Kδ present in the cell or organism.

The terms "PI3K isoform selective inhibitor" generally refers to a compound that inhibits the activity of one or more PI3K isoforms more effectively than the other remaining PI3K isoforms. By way of example, the term "PI3Kδ selective inhibitor" generally refers to a compound that inhibits the activity of the PI3Kδ isoform more effectively than other isoforms of the PI3K family (e.g., PI3K α, β, or γ).

The relative efficacies of compounds as inhibitors of an enzyme activity (or other biological activity) can be established by determining the concentrations at which each compound inhibits the activity to a predefined extent and then comparing the results. In one embodiment, the efficacy of a compound as an inhibitor of one or more PI3K isoforms can be measured by the concentration that inhibits 50% of the activity in a biochemical assay, i.e., the 50% inhibitory concentration or "$IC_{50}$". $IC_{50}$ determinations can be accomplished using conventional techniques known in the art, including the techniques describes in the Examples below. In general, an $IC_{50}$ can be determined by measuring the activity of a given enzyme in the presence of a range of concentrations of the compound under study. The experimentally obtained values of enzyme activity may then be plotted against the compound concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it may be desirable to establish a 90% inhibitory concentration, i.e., $IC_{90}$.

In one embodiment, a PI3Kδ selective inhibitor is a compound that exhibits a 50% inhibitory concentration ($IC_{50}$) with respect to PI3Kδ that is at least 10-fold, in another aspect at least 20-fold, and in another aspect at least 30-fold, lower than the $IC_{50}$ value with respect to any or all of the other Class I PI3K family members. In another embodiment, a PI3Kδ selective inhibitor is a compound that exhibits an $IC_{50}$ with respect to PI3Kδ that is at least 50-fold, in another aspect at least 100-fold, in an additional aspect at least 200-fold, and in yet another aspect at least 500-fold, lower than the $IC_{50}$ with respect to any or all of the other PI3K Class I family members. A PI3Kδ selective inhibitor is typically administered in an amount such that it selectively inhibits PI3Kδ activity, as described above.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of a PI3Kδ selective inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds of formula (I), (IA), (IB), (IC), or (II), or a pharmaceutically acceptable salt, prodrug, or solvate thereof, may be further characterized to examine the safety or tolerance dosage in human or non-human subjects. Such properties may be examined using commonly known methods to those skilled in the art.

Compared to other PI3K isoforms, PI3Kδ is generally expressed in hematopoietic cells. Consequently, the direct effects of selective inhibitors of PI3Kδ can be observed in hematopoietic cells. Hematopoietic cells typically differentiate into either lymphoid progenitor cells or myeloid progenitor cells, both of which ultimately differentiate into various mature cell types including leukocytes. Aberrant proliferation of hematopoietic cells of one type often interferes with the production or survival of other hematopoietic cell types, which can result in compromised immunity, anemia, and/or thrombocytopenia. The methods described herein may treat aberrant proliferation of hematopoietic cells by inhibiting aberrant proliferation of hematopoietic cells. As a result, these methods may also ameliorate the symptoms and secondary conditions that result from a primary effect such as excessive system or localized levels of leukocytes or lymphocytes.

In some embodiments, the compounds described herein may be used to treat subjects having various disease states, disorders, and conditions (also collectively referred to as "indications") involving aberrant proliferation of hematopoietic cells (including excessive production of lymphoid progenitor cell-derived cells and/or myeloid progenitor cell-derived cells). Such indications may include, for example, leukemias, lymphomas, myeloproliferative disorders, myelodysplastic syndromes, and plasma cell neoplasms. In certain embodiments, the compounds described herein may be used to treat hematologic malignancies, inflammation, autoimmune disorders, allergic conditions, cardiovascular disease, and autoimmune diseases. In certain embodiments, allergic conditions may include all forms of hypersensitivity.

In other embodiments, the compounds described herein may be used to treat cancers that are mediated by, dependent on or associated with PI3K activity, such as PI3Kδ activity. In certain embodiments, the disease is a hematologic malignancy. In certain embodiments, the disease is lymphoma, multiple myeloma, or leukemia. In particular embodiments, the hematologic malignancy is leukemia or lymphoma. In specific embodiments, the disease is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), juvenile myelomonocytic leukemia (JMML), multiple myeloma (MM), Hodgkin lymphoma, indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), minimal residual disease (MRD), T-cell lymphoma, B-cell lymphoma, diffuse large B-cell lymphoma (DLBCL), T-cell acute lymphoblastic leukemia (T-ALL), B-cell acute lymphoblastic leukemia (B-ALL), lymphoplasmacytic lymphoma, marginal zone lymphoma, or Burkitt lymphoma. In one embodiment, the disease is T-cell acute lymphoblastic leukemia (T-ALL), or B-cell acute lymphoblastic leukemia (B-ALL). It should be understood that the non-Hodgkin lymphoma may, in certain embodiments, encompass the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL).

In other embodiments, the disease is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

Provided is a method for treating a subject, who has or is suspected of having a disease or condition responsive or believed to be responsive to the inhibition of PI3Kδ activity by administering to the subject a compound of formula (I), (IA), (IB), (IC), or (II), or a pharmaceutically acceptable salt, prodrug, or solvate thereof.

Provided is also a method of inhibiting kinase activity of a phosphatidylinositol 3-kinase delta polypeptide by contacting the polypeptide with a compound of formula (I), (IA), (IB), (IC), or (II), or a pharmaceutically acceptable salt, prodrug, or solvate thereof. Also provided is a method for increasing sensitivity of cancer cells to chemotherapy, comprising administering to a patient undergoing chemotherapy with a chemotherapeutic agent an amount a compound of formula (I), (IA), (IB), (IC), or (II), or a pharmaceutically acceptable salt, prodrug, or solvate thereof, sufficient to increase the sensitivity of cancer cells to the chemotherapeutic agent. In some embodiments, the cancers cells are of hematopoietic origin.

Combination Therapies

In one embodiment, the compounds of the present application (e.g., a compound of formula (I), (IA), (IB), (IC), or (II), or a pharmaceutically acceptable salt, prodrug, or solvate thereof) may be used in combination with one or more additional therapeutic agent that are being used and/or developed to treat cancers or inflammatory disorders. The one or more additional therapeutic agent may be an inhibitor to PI3K such as PI3Kγ, PI3Kβ, and/or PI3Kα, Janus kinase (JAK) such as JAK1, JAK2 and/or JAK3, spleen tyrosine kinase (SYK), Bruton's tyrosine kinase (BTK), bromodomain containing protein inhibitor (BRD) such as BRD4, a lysyl oxidase protein (LOX), lysyl oxidase-like protein (LOXL) such as LOXL1-5, matrix metalloprotease (MMP) such as MMP 1-10, adenosine A2B receptor (A2B), isocitrate dehydrogenase (IDH) such as IDH1, apoptosis signal-regulating kinase (ASK) such as ASK1, serine/threonine kinase TPL2, discoidin domain receptor (DDR) such as DDR1 and DDR2, histone deacetylase (HDAC), protein kinase C (PKC), or any combination thereof.

One, two, three, or more of the therapeutic agents (e.g. a PI3K inhibitor, a JAK inhibitor, a SYK inhibitor, a BTK inhibitor, a BRD4 inhibitor, a LOXL2 inhibitor, a MMP9 inhibitor, a A2B inhibitor, an IDH inhibitor, an ASK inhibitor, a TPL2 inhibitor, a DDR1 inhibitor, a TBK inhibitor, a HDAC inhibitor, a PKC inhibitor) may be further used or combined with a chemotherapeutic agent, an immunotherapeutic agent, a radiotherapeutic agent, an anti-neoplastic agent, an anti-cancer agent, an anti-fibrotic agent, an anti-angiogenic agent, a therapeutic antibody, or any combination thereof.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate); compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, *Pseudomonas exotoxin, Bordetella pertussis* adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) may encompass any non-proteinaceous (e.g., non-peptidic) chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofuran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL(r), Bristol Meyers Squibb Oncology, Princeton, N.J.) and docetaxel (TAXOTERE(r), Rhone-Poulenc Rorer, Antony, France); chlorambucil; gemcitabine (Gemzar(r)); 6-thioguanine; mercaptopurine; methotrexate; platinum analogs such as cisplatin and carboplatin; vinblastine; platinum; etoposide (VP-16); ifosfamide; mitoxantrone; vancristine; vinorelbine (Navelbine(r)); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application. For example, gemcitabine, nab-paclitaxel, and gemcitabine/nab-paclitaxel are used with the JAK inhibitor and/or PI3Kδ inhibitor for treating hyperproliferative disorders.

Chemotherapeutic agents may also include, for example, anti-hormonal agents that act to regulate or inhibit hormone action on tumors such as anti-estrogens and selective estrogen receptor modulators (SERMs), including, for example, tamoxifen (including Nolvadex), raloxifene, droloxifene, 4-hydroxytamoxifen, trioxifene, keoxifene, LY117018, onapristone, and toremifene (Fareston(r)); inhibitors of the enzyme aromatase, which regulates estrogen production in the adrenal glands, such as, for example, 4(5)-imidazoles, aminoglutethimide, megestrol acetate (Megace(r)), exemestane, formestane, fadrozole, vorozole (Rivisor(r)), letrozole (Femara(r)), and anastrozole (Arimidex(r).); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN(r), ENDOSTATIN(r), suramin, squalamine, tissue inhibitor of metalloproteinase-1, tissue inhibitor of metalloprotemase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3, 4-dehydroproline, thiaproline, .alpha.-dipyridyl, beta-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N, and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,5059,714; U.S. Pat. No. 5,120,764; U.S. Pat. No. 5,182,297; U.S. Pat. No. 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131.

The application also provides a method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In certain embodiments, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107 (1), p. 265-276.

Examples of immunotherapeutic agents treating lymphoma or leukemia include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCl-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP(R-MCP).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Kits

Provided herein are also kits that include a compound of formula (I), (IA), (IB), (IC), or (II), or a pharmaceutically acceptable salt, prodrug, or solvate thereof, and suitable packaging. In one embodiment, a kit further includes instructions for use. In one aspect, a kit includes a compound of formula (I), (IA), (IB), (IC), or (II), or a pharmaceutically acceptable salt, prodrug, or solvate thereof, and a label and/or instructions for use of the compounds in the treatment of the indications, including the diseases or conditions, described herein.

Provided herein are also articles of manufacture that include a compound of formula (I), (IA), (IB), (IC), or (II), or a pharmaceutically acceptable salt, prodrug, or solvate thereof, in a suitable container. The container may be a vial, jar, ampoule, preloaded syringe, and intravenous bag.

Pharmaceutical Compositions and Administration

Compounds provided herein are usually administered in the form of pharmaceutical compositions. Thus, provides herein are also pharmaceutical compositions that contain one or more of the compounds of formula (I), (IA), (IB), (IC), or (II), or a pharmaceutically acceptable salt, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant. In certain embodiments, the compound of formula (I), (IA), (IB), (IC), or (II), or a pharmaceutically acceptable salt, prodrug, or solvate thereof, is administered intraveneously, intramuscularly, parenterally, nasally or orally.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of formula (I), (IA), (IB), (IC), or (II), or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of formula (I), (IA), (IB), (IC), or (II), or a pharmaceutically acceptable salt, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound of formula (I), (IA), (IB), (IC), or (II), or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

Exemplary unit dosage levels of a compound of formula (I), (IA), (IB), (IC), or (II), or a pharmaceutically acceptable salt, prodrug, or solvate thereof, for a human subject may, in certain variations, be between about 0.01 mg to about 1000 mg, between about 1 mg to about 15 mg, or between about 50 mg to about 200 mg, or about 5 mg, about 10 mg, about 15 mg, about 25 mg, about 50 mg, about 75 mg, about 100 mg, about 125 mg, or about 150 mg, or about 175 mg, about 200 mg, or about 250 mg.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of formula (I), (IA), (IB), (IC), or (II), for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of formula (I), (IA), (IB), (IC), or (II) per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound of formula (I), (IA), (IB), (IC), or (II) administered per dose or per day. Daily dosage of a compound of formula (I), (IA), (IB), (IC), or (II) may be between about 1 mg/day and 4,000 mg/day, between about 2,000 mg/day to 4,000 mg/day, between about 1 mg/day to 2,000 mg/day, between about 1 mg/day to 1,000 mg/day, between about 10 mg/day to 500 mg/day, between about 20 mg/day to 500 mg/day, between about 50 mg/day to 300 mg/day, between about 75 mg/day to 200 mg/day, between about 15 mg/day to 150 mg/day, or between 1 mg/day and 15 mg/day.

When administered orally, the total daily dosage for a human subject may be between 1 mg and 1,000 mg, between about 10-500 mg/day, between about 50-300 mg/day, between about 75-200 mg/day, or between about 100-150 mg/day.

The compounds of formula (I), (IA), (IB), (IC), or (II) or the compositions thereof may be administered once, twice, three, or four times daily, using any suitable mode described above. Also, administration or treatment with the compounds formula (I), (IA), (IB), (IC), or (II) may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound of formula (I), (IA), (IB), (IC), or (II) and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula (I), (IA), (IB), (IC) or (II)

The compounds of formula (I), (IA), (IB), (IC) or (II) may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds of Formula I or II

One method of preparing compounds of formula (I) is shown in Reaction Scheme I.

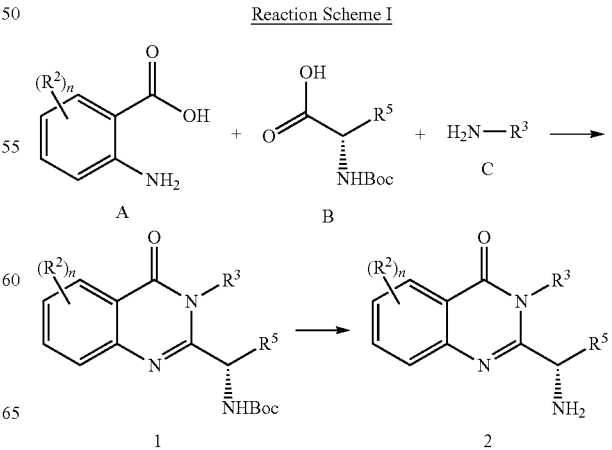

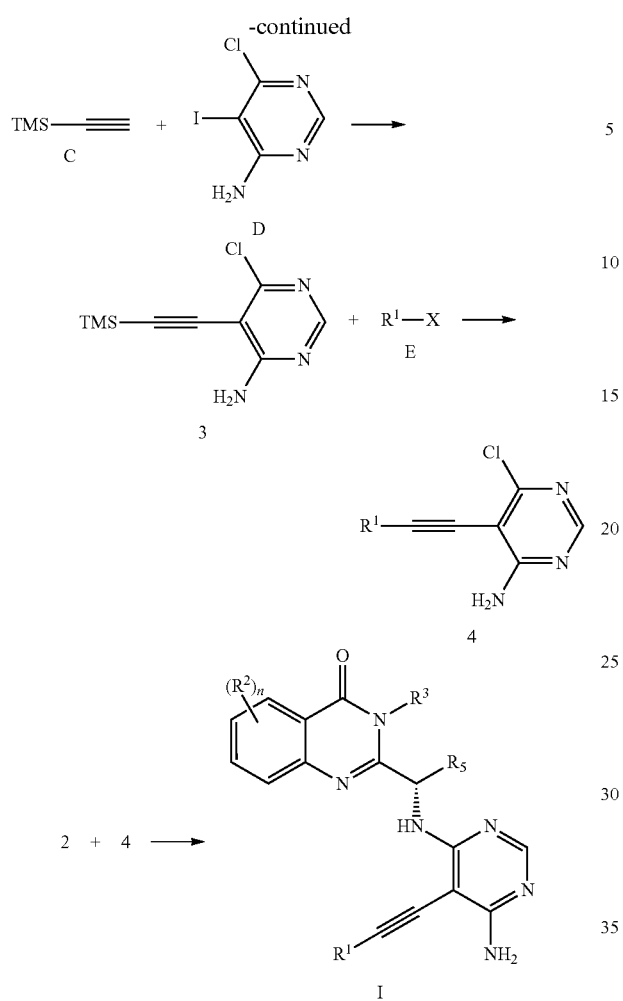

It should be understood that Reaction Scheme I depicted above and described in further detail below may also be used to synthesize compounds of formula (II).

Step 1

Preparation of a Compound of Formula (1)

The compound of formula (1) can be made by combining compounds (A), (B) and (C) in the presence of a dehydrating agent in a solvent. Compounds (A), (B) and (C) are commercially available. With respect to compound (A), $R^2$ is as defined herein. With respect to compound (B), $R^5$ is as defined herein. With respect to compound (C), $R^3$ is as defined herein. Compound (A) can be mixed with Compound (B) in the presence of a coupling agent such as diphenyl phosphite in a solvent such as pyridine. After stirring at a temperature between ambient and 100° C. for between 1 and 5 hours, compound (C) is added. After further stirring at a temperature between ambient and 100° C. for between 5 and 24 hours, the reaction mixture is allowed to cool to room temperature. To extract the compound of formula (1), an organic solvent such as ethyl acetate (EtOAc) may be added, followed by washing with, mild acid, water, and brine. The organic phase can be concentrated to obtain the compound of formula (1). The compound of formula (1) may be purified by any suitable methods known in the art, such as chromatography on silica gel. Alternatively, the compound of formula (1) may be used in the next step without purification.

Step 2

Preparation of a Compound of Formula (2)

The compound of formula (2) can be made by removing the protecting group from the compound of formula (1). The compound of formula (1) is dissolved in a suitable solvent and treated with a suitable acid. Suitable solvents may include, for example, dichloromethane, dioxane, or mixtures thereof. Suitable acids may include, for example, trifluoroacetic acid or hydrochloric acid. The reaction can be carried out temperatures between −20° C. to ambient temperature. On reaction completion, solvent is removed to obtain the compound of formula (2).

Step 3

Preparation of Compound (3)

Compound (3) can be made by performing a Sonogashira coupling of commercially available trimethylsilylalkyne (TMS-alkyne; compound (C)) and 4-amino-6-chloro-5-iodopyrimidine (compound (D)). This type of reaction generally uses a palladium catalyst, a copper catalyst and a base to form a carbon-carbon bond between the terminal alkyne of compound (C) and the heteroaryl halide (i.e., compound (D)). An example of a suitable palladium catalyst is $Pd(PPh_3)_4$. An example of a suitable copper catalyst is CuI. An example of a suitable base is triethylamine (TEA). The coupling reaction may also be performed in the presence of a solvent. An example of a suitable solvent is N-methylpyrrolidone (NMP). The coupling reaction may be performed at elevated temperatures, for example, between 80° C. and 100° C. for about 30 minutes to 24 hours. The reaction can be quenched by addition of water, and the reaction mixture can be extracted with a suitable solvent such as ethyl acetate (EtOAc). The organic layer can be isolated, dried (e.g., using $Na_2SO_4$), and concentrated. The residue can then be purified using any suitable methods known in the art, for example, on a silica column, to yield compound (3). The residue may also be used crude, without purification, in the next step.

Step 4

Preparation of a Compound of Formula (4)

The compound of formula (4) can be made by a second Sonogashira coupling between compound (3) and compound (E) having the formula $R^1$—X, where $R^1$ is as defined herein, and X is halo. The conditions for this second Sonogashira coupling is similar to the first coupling discussed above; however, this reaction further involves the use of a reagent to remove the TMS protecting group. Such a suitable reagent is tetra-n-butylammonium fluoride (TBAF). Similar to the first Sonogashira coupling, this reaction generally uses a palladium catalyst, a copper catalyst and a base. An example of a suitable palladium catalyst is $Pd(PPh_3)_4$. An example of a suitable copper catalyst is CuI. An example of a suitable base is triethylamine (TEA). The coupling reaction may also be performed in the presence of a solvent. An example of a suitable solvent is N-methylpyrrolidone (NMP). This coupling reaction may be performed at elevated temperatures, for example, between 80° C. to 100° C. for about 1 to 24 hours. The reaction is quenched by addition of water, and the reaction mixture can be extracted with a suitable solvent such as ethyl acetate (EtOAc). The organic layer can be isolated, dried (e.g., using $Na_2SO_4$), and concentrated. The residue can then be purified using any suitable methods known in the art, for example, on a silica column, to yield a compound of formula (4). The residue may also be used crude, without purification, in the next step.

Step 5

Preparation of a Compound of Formula (I)

The compound of formula (I) can generally be prepared by coupling compound of formula (2) and compound of formula (4) in the presence of a suitable base in a suitable solvent. An example of a suitable base is diisopropylethylamine. An example of a suitable solvent is N-methylpyrrolidone (NMP). The reaction is typically performed at a temperature between 50° C. to 150° C. for about 30 minutes to 24 hours. Alternatively the reaction can be performed in a microwave at a temperature between 100° C. to 150° C. for about 30 minutes to 24 hours. Water can be added to quench the reaction upon completion, and the precipitate may be filtered and then dissolved in an organic solvent such as dichloromethane (DCM). The product can be isolated by methods known in the art, for example by removal of solvent under reduced pressure. The product can be purified using any suitable methods known in the art, for example, chromatography of the residue on a silica column.

Alternative Preparation

Another method of preparing compounds of formula (I) or (II) is shown in Reaction Scheme II.

The compound of formula (I) may also be prepared by coupling a compound of formula (6) with commercially available compound of formula (G). The compound of formula (6) may be prepared in a manner similar to that described above for a compound of formula (1), by reacting a compound of formula (2) with an appropriately-substituted 4-chloro-6-aminopyrimidine. Compound (G) has a structure of formula $R^1$—C≡C, where $R^1$ is as defined herein.

The coupling reaction is performed in the presence of a palladium catalyst, a copper catalyst and a base to form a carbon-carbon bond between the terminal alkyne of Compound (G) and the compound of formula (6). An example of a suitable palladium catalyst is $Pd(PPh_3)_2C_2$. An example of a suitable copper catalyst is CuI. An example of a suitable base is triethylamine (TEA). The coupling reaction may also be performed in the presence of a solvent. An example of a suitable solvent is tetrahydrofuran (THF). The coupling reaction may be performed at elevated temperatures, for example, between 50° C. and 120° C. for about 1 to 12 hours. Upon completion, the reaction is concentrated by removal of the solvent. The residue can be purified using any suitable methods known in the art, for example, chromatography of the residue on a silica column.

Example 1a

Preparation of a Compound of Formula (1)

A. Preparation of a Compound of Formula (1) in which n is 1, $R^2$ is chloro, and $R^3$ is phenyl Reaction Scheme II

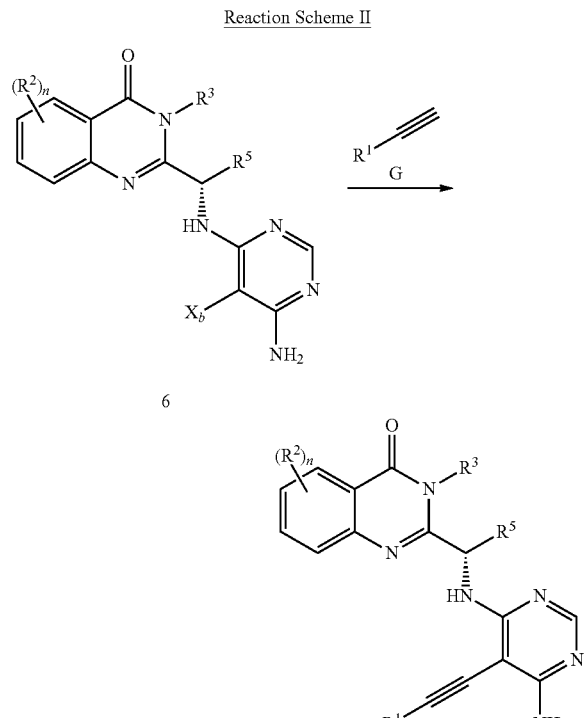

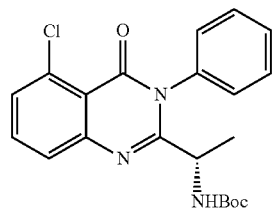 [SMILES: C[C@H](NC(=O)OC(C)(C)C)c1nc2cccc(Cl)c2c(=O)n1-c1ccccc1]

Diphenyl phosphonate (1.9 mL, 10 mmol) was added to a solution of 2-amino-6-chlorobenzoic acid (495 mg, 2.9 mmol) and (S)-2-(tert-butoxycarbonylamino)propanoic acid (710 mg, 3.77 mmol) in pyridine (3 mL). The reaction mixture was stirred at 40° C. for 2 hours. Aniline (274 mg, 3.48 mmol) was then added to the reaction mixture, which was then stirred at 55° C. for 12 hours. The reaction mixture was cooled to room temperature. This mixture was then diluted with EtOAc (50 mL), washed with 1N aqueous HCl (2×50 mL), brine (50 mL), and dried over sodium sulfate. The organics layer was filtered and concentrated in vacuuo to afford material which was purified by column chromatography on $SiO_2$ eluting with EtOAc in hexanes (0-50%) to afford (S)-tert-butyl 1-(5-chloro-4-oxo-3-phenyl-3,4-dihydroquinazolin-2-yl)ethylcarbamate as a solid. ES/MS m/z=400.1 $(M+H)^+$.

B. Preparation of a Compound of Formula (1), Varying $R^2$ and $R^3$

Following the procedure described in Example 1a.A and Reaction Scheme I, but varying the $R^2$ and $R^3$ substituents, other compounds of formula (I) were prepared including:

It should be understood that Reaction Scheme II depicted above and described in further detail below may also be used to synthesize compounds of formula (II).

(S)-tert-butyl 2-(5-chloro-4-oxo-3-phenyl-3,4-dihydroquinazolin-2-yl)pyrrolidine-1-carboxylate, ES/MS m/z=426.1 (M+H)⁺;
(S)-tert-butyl 2-(5-chloro-4-oxo-3-phenyl-3,4-dihydroquinazolin-2-yl)piperidine-1-carboxylate, ES/MS m/z=440.1 (M+H)⁺;
(S)-tert-butyl 1-(8-fluoro-4-oxo-3-phenyl-3,4-dihydroquinazolin-2-yl)ethylcarbamate, ES/MS m/z=384.1 (M+H)⁺;
(S)-tert-butyl 1-(5,8-dichloro-4-oxo-3-phenyl-3,4-dihydroquinazolin-2-yl)ethylcarbamate, ES/MS m/z=434.2 (M+H)⁺;
(S)-tert-butyl 1-(5-chloro-8-fluoro-4-oxo-3-phenyl-3,4-dihydroquinazolin-2-yl)ethylcarbamate, ES/MS m/z=418.1 (M+H)⁺;
(S)-tert-butyl 1-(8-chloro-4-oxo-3-phenyl-3,4-dihydroquinazolin-2-yl)ethylcarbamate, ES/MS m/z=400.1 (M+H)⁺;
(S)-tert-butyl 1-(5,8-difluoro-4-oxo-3-phenyl-3,4-dihydroquinazolin-2-yl)ethylcarbamate, ES/MS m/z=402.1 (M+H)⁺;
(S)-tert-butyl (1-(5-methoxy-4-oxo-3-phenyl-3,4-dihydroquinazolin-2-yl)ethyl)carbamate;
(S)-tert-butyl (1-(5-chloro-8-methyl-4-oxo-3-phenyl-3,4-dihydroquinazolin-2-yl)ethyl)carbamate;
(S)-tert-butyl (1-(5-methyl-4-oxo-3-phenyl-3,4-dihydroquinazolin-2-yl)ethyl)carbamate;
(S)-tert-butyl (1-(5-bromo-4-oxo-3-phenyl-3,4-dihydroquinazolin-2-yl)ethyl)carbamate;
(S)-tert-butyl (1-(8-methyl-4-oxo-3-phenyl-3,4-dihydroquinazolin-2-yl)ethyl)carbamate;
(S)-tert-butyl (1-(3-(3-butylphenyl)-5-chloro-4-oxo-3,4-dihydroquinazolin-2-yl)ethyl)carbamate;
(S)-tert-butyl (1-(3-(3-t-butylphenyl)-5-chloro-4-oxo-3,4-dihydroquinazolin-2-yl)ethyl)carbamate;
(S)-tert-butyl (1-(5-chloro-3-(3-(methylsulfonyl)phenyl)-4-oxo-3,4-dihydroquinazolin-2-yl)ethyl)carbamate;
(S)-tert-butyl (1-(3-([1,1'-biphenyl]-3-yl)-5-chloro-4-oxo-3,4-dihydroquinazolin-2-yl)ethyl)carbamate;
(S)-tert-butyl (1-(3-(3-ethylphenyl)-5-chloro-4-oxo-3,4-dihydroquinazolin-2-yl)ethyl)carbamate;
(S)-tert-butyl (1-(8-fluoro-5-methyl-4-oxo-3-phenyl-3,4-dihydroquinazolin-2-yl)ethyl)carbamate;
(S)-tert-butyl (1-(5,8-difluoro-4-oxo-3-phenyl-3,4-dihydroquinazolin-2-yl)ethyl)carbamate;
(S)-tert-butyl (1-(8-fluoro-4-oxo-3-phenyl-3,4-dihydroquinazolin-2-yl)ethyl)carbamate;
(S)-tert-butyl (1-(5-fluoro-4-oxo-3-phenyl-3,4-dihydroquinazolin-2-yl)ethyl)carbamate;
(S)-tert-butyl (1-(5-(difluoromethyl)-3-(3,5-difluorophenyl)-4-oxo-3,4-dihydroquinazolin-2-yl)ethyl)carbamate;
(S)-tert-butyl (1-(5-(difluoromethyl)-4-oxo-3-phenyl-3,4-dihydroquinazolin-2-yl)ethyl)carbamate;
(S)-tert-butyl (1-(5-(trifluoromethyl)-3-(3,5-difluorophenyl)-4-oxo-3,4-dihydroquinazolin-2-yl)ethyl)carbamate;
(S)-tert-butyl (1-(5-fluoro-8-methyl-4-oxo-3-phenyl-3,4-dihydroquinazolin-2-yl)ethyl)carbamate;
(S)-tert-butyl (1-(3-(3-cyanophenyl)-5-(difluoromethyl)-4-oxo-3,4-dihydroquinazolin-2-yl)ethyl)carbamate;
(S)-tert-butyl (1-(3-(3-cyanophenyl)-8-fluoro-5-methyl-4-oxo-3,4-dihydroquinazolin-2-yl)ethyl)carbamate;
(S)-tert-butyl (1-(5-(difluoromethyl)-3-(3,5-difluorophenyl)-4-oxo-3,4-dihydroquinazolin-2-yl)propyl)carbamate;
(S)-tert-butyl (1-(5-chloro-3-(3-methoxy-2-methylphenyl)-4-oxo-3,4-dihydroquinazolin-2-yl)ethyl)carbamate;
(S)-tert-butyl (1-(5-chloro-3-(3,5-difluorophenyl)-8-fluoro-4-oxo-3,4-dihydroquinazolin-2-yl)ethyl)carbamate;
(S)-tert-butyl (1-(5-chloro-3-(3,5-difluorophenyl)-4-oxo-3,4-dihydroquinazolin-2-yl)ethyl)carbamate;
(S)-tert-butyl (1-(3-(3,5-difluorophenyl)-5-fluoro-4-oxo-3,4-dihydroquinazolin-2-yl)ethyl)carbamate;
(R)-tert-butyl (1-(5-chloro-3-(3,5-difluorophenyl)-4-oxo-3,4-dihydroquinazolin-2-yl)ethyl)carbamate;
(S)-tert-butyl (1-(5-chloro-3-(3-chlorophenyl)-4-oxo-3,4-dihydroquinazolin-2-yl)ethyl)carbamate;
(S)-tert-butyl (1-(6-fluoro-4-oxo-3-phenyl-3,4-dihydroquinazolin-2-yl)ethyl)carbamate;
(S)-tert-butyl (1-(5-chloro-3-(3-cyanophenyl)-4-oxo-3,4-dihydroquinazolin-2-yl)ethyl)carbamate;
(S)-tert-butyl (1-(3-(3-cyanophenyl)-6-fluoro-4-oxo-3,4-dihydroquinazolin-2-yl)ethyl)carbamate;
(S)-tert-butyl (1-(3-(3-chlorophenyl)-6-fluoro-4-oxo-3,4-dihydroquinazolin-2-yl)ethyl)carbamate;
(S)-tert-butyl (1-(5-fluoro-3-(3-fluorophenyl)-4-oxo-3,4-dihydroquinazolin-2-yl)ethyl)carbamate;
(S)-tert-butyl (1-(3-(3-fluorophenyl)-5-methyl-4-oxo-3,4-dihydroquinazolin-2-yl)ethyl)carbamate;
(S)-tert-butyl (1-(3-(3,5-difluorophenyl)-5-fluoro-4-oxo-3,4-dihydroquinazolin-2-yl)propyl)carbamate;
(S)-tert-butyl (1-(3-(3,5-difluorophenyl)-5-methyl-4-oxo-3,4-dihydroquinazolin-2-yl)propyl)carbamate;
(S)-tert-butyl (1-(3-(3-cyanophenyl)-5-fluoro-4-oxo-3,4-dihydroquinazolin-2-yl)ethyl)carbamate;
(S)-tert-butyl (1-(5-(methylsulfonyl)-4-oxo-3-phenyl-3,4-dihydroquinazolin-2-yl)ethyl)carbamate;
(S)-tert-butyl (1-(5-cyano-4-oxo-3-phenyl-3,4-dihydroquinazolin-2-yl)ethyl)carbamate;
(S)-tert-butyl (1-(5-fluoro-4-oxo-3-(pyridin-3-yl)-3,4-dihydroquinazolin-2-yl)ethyl)carbamate;
(S)-tert-butyl (1-(5-chloro-4-oxo-3-(pyridin-3-yl)-3,4-dihydroquinazolin-2-yl)ethyl)carbamate;
(S)-tert-butyl (1-(5-methyl-4-oxo-3-(pyridin-3-yl)-3,4-dihydroquinazolin-2-yl)ethyl)carbamate;
(S)-tert-butyl (1-(3-(5-fluoropyridin-3-yl)-5-methyl-4-oxo-3,4-dihydroquinazolin-2-yl)ethyl)carbamate;
(S)-tert-butyl (1-(5-chloro-3-morpholino-4-oxo-3,4-dihydroquinazolin-2-yl)ethyl)carbamate;
(S)-tert-butyl (1-(5-chloro-3-(3-(methylsulfonamidomethyl)phenyl)-4-oxo-3,4-dihydroquinazolin-2-yl)ethyl)carbamate;
tert-butyl ((1S)-1-(5-chloro-3-((1R,5S)-8-methyl-8-azabicyclo[3.2.1]octan-3-yl)-4-oxo-3,4-dihydroquinazolin-2-yl)ethyl)carbamate;
(S)-tert-butyl (1-(3-(azepan-1-yl)-5-chloro-4-oxo-3,4-dihydroquinazolin-2-yl)ethyl)carbamate;
(S)-tert-butyl (1-(5-chloro-4-oxo-3-(piperazin-1-yl)-3,4-dihydroquinazolin-2-yl)ethyl)carbamate;
(S)-tert-butyl (1-(5-methyl-3-(3-((N-methylmethylsulfonamido)methyl)phenyl)-4-oxo-3,4-dihydroquinazolin-2-yl)ethyl)carbamate;
(S)-tert-butyl (1-(5-chloro-3-(3-((N-methylmethylsulfonamido)methyl)phenyl)-4-oxo-3,4-dihydroquinazolin-2-yl)ethyl)carbamate;
(S)-tert-butyl (1-(5-chloro-3-(3-((N-isobutylmethylsulfonamido)methyl)phenyl)-4-oxo-3,4-dihydroquinazolin-2-yl)ethyl)carbamate;
(R)-tert-butyl (1-(5-chloro-4-oxo-3-phenyl-3,4-dihydroquinazolin-2-yl)-2-hydroxyethyl)carbamate; and (R)-tert-butyl (1-(5-chloro-3-(3,5-difluorophenyl)-4-oxo-3,4-dihydroquinazolin-2-yl)-2-methoxyethyl)carbamate.

Example 1b

Preparation of a Compound of Formula (1)

A. Preparation of a Compound of Formula (1) in which n is 1, $R^2$ is cyano, and $R^3$ is phenyl

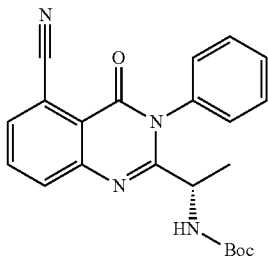 [SMILES: C[C@H](NC(=O)OC(C)(C)C)c1nc2cccc(C#N)c2c(=O)n1-c1ccccc1]

(S)-tert-butyl (1-(5-bromo-4-oxo-3-phenyl-3,4-dihydroquinazolin-2-yl)ethyl)carbamate (500 mg, 1.13 mmol), zinc cyanide (166 mg, 1.41 mmol), and tetrakis(triphenylphosphine)Pd(0) (124 mg, 0.11 mmol) were combined in NMP (5 mL). The mixture was degassed under Ar and heated to 90° C. overnight. The reaction was poured into EtOAc, washed with water (3×), and purified by flash chromatography (40 g silica, 0-50% EtOAc/hexanes) to give (S)-tert-butyl (1-(5-cyano-4-oxo-3-phenyl-3,4-dihydroquinazolin-2-yl)ethyl)carbamate as a white solid. ES/MS 391.2 (M+H$^+$).

Example 2a

Preparation of a Compound of Formula (2)

A. Preparation of a Compound of Formula (2) in which n is 1, $R^2$ is chloro, and $R^3$ is phenyl

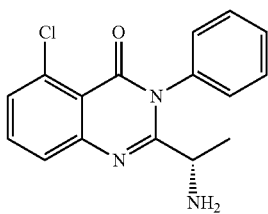 [SMILES: C[C@H](N)c1nc2cccc(Cl)c2c(=O)n1-c1ccccc1]

Trifluoroacetic acid (3 mL) was added to a solution of (S)-tert-butyl 1-(5-chloro-4-oxo-3-phenyl-3,4-dihydroquinazolin-2-yl)ethylcarbamate (1 g, 2.5 mmol) in dichloromethane (3 mL). The resultant was stirred at room temperature for 3 hours. The solvent was removed in vacuuo to afford (S)-2-(1-aminoethyl)-5-chloro-3-phenylquinazolin-4(3H)-one 2,2,2-trifluoroacetic acid salt. ES/MS m/z=300.1 (M+H)$^+$ B. Preparation of a Compound of Formula (2), varying $R^2$ and $R^3$ Following the procedure described in Example 2a.A and Reaction Scheme I, but varying the $R^2$ and $R^3$ substituents, other compounds of formula (2) were prepared including:
(S)-5-chloro-3-phenyl-2-(pyrrolidin-2-yl)quinazolin-4(3H)-one, ES/MS m/z=326.1 (M+H)$^+$;
(S)-5-chloro-3-phenyl-2-(piperidin-2-yl)quinazolin-4(3H)-one, ES/MS m/z=340.1 (M+H)$^+$;
(S)-2-(1-aminoethyl)-5-(3-morpholino-3-oxopropyl)-3-phenylquinazolin-4(3H)-one, ES/MS m/z=407.2 (M+H)$^+$;
(S)-3-(2-(1-aminoethyl)-4-oxo-3-phenyl-3,4-dihydroquinazolin-5-yl)-N,N-dimethylpropanamide, ES/MS m/z=365.2 (M+H$^+$);
(S)-2-(1-aminoethyl)-8-fluoro-3-phenylquinazolin-4(3H)-one, ES/MS m/z=284.1 (M+H)$^+$;
(S)-2-(1-aminoethyl)-5,8-dichloro-3-phenylquinazolin-4(3H)-one, ES/MS m/z=334.1 (M+H)$^+$;
(S)-2-(1-aminoethyl)-5-chloro-8-fluoro-3-phenylquinazolin-4(3H)-one, ES/MS m/z=318.1 (M+H);
(S)-2-(1-aminoethyl)-8-chloro-3-phenylquinazolin-4(3H)-one, ES/MS m/z=300.1 (M+H)$^+$;
(S)-2-(1-aminoethyl)-5,8-difluoro-3-phenylquinazolin-4(3H)-one, ES/MS m/z=302.1 (M+H)$^+$;
(S)-2-(1-aminoethyl)-5-chloro-8-methyl-3-phenylquinazolin-4(3H)-one;
(S)-2-(1-aminoethyl)-5-methyl-3-phenylquinazolin-4(3H)-one;
(S)-2-(1-aminoethyl)-4-oxo-3-phenyl-3,4-dihydroquinazoline-5-carbonitrile;
(S)-2-(1-aminoethyl)-8-methyl-3-phenylquinazolin-4(3H)-one;
(S)-2-(1-aminoethyl)-3-(3-butylphenyl)-5-chloroquinazolin-4(3H)-one;
(S)-2-(1-aminoethyl)-3-(3-ethylphenyl)-5-chloroquinazolin-4(3H)-one;
(S)-2-(1-aminoethyl)-3-(3-t-butylphenyl)-5-chloroquinazolin-4(3H)-one;
(S)-2-(1-aminoethyl)-5-chloro-3-(3-(methylsulfonyl)phenyl)quinazolin-4(3H)-one;
(S)-3-([1,1'-biphenyl]-3-yl)-2-(1-aminoethyl)-5-chloroquinazolin-4(3H)-one;
(S)-2-(1-aminoethyl)-8-fluoro-5-methyl-3-phenylquinazolin-4(3H)-one;
(S)-2-(1-aminoethyl)-5,8-difluoro-3-phenylquinazolin-4(3H)-one;
(S)-2-(1-aminoethyl)-8-fluoro-3-phenylquinazolin-4(3H)-one;
(S)-2-(1-aminoethyl)-5-fluoro-3-phenylquinazolin-4(3H)-one;
(S)-2-(1-aminoethyl)-5-(difluoromethyl)-3-(3,5-difluorophenyl)quinazolin-4(3H)-one;
(S)-2-(1-aminoethyl)-5-(difluoromethyl)-3-phenylquinazolin-4(3H)-one;
(S)-2-(1-aminoethyl)-5-(trifluoromethyl)-3-(3,5-difluorophenyl)quinazolin-4(3H)-one;
(S)-2-(1-aminoethyl)-5-fluoro-8-methyl-3-phenylquinazolin-4(3H)-one;
(S)-3-(2-(1-aminoethyl)-5-(difluoromethyl)-4-oxoquinazolin-3(4H)-yl)benzonitrile;
(S)-3-(2-(1-aminoethyl)-8-fluoro-5-methyl-4-oxoquinazolin-3(4H)-yl)benzonitrile;
(S)-2-(1-aminopropyl)-5-(difluoromethyl)-3-(3,5-difluorophenyl)quinazolin-4(3H)-one;
(S)-2-(1-aminoethyl)-5-chloro-3-(3-methoxy-2-methylphenyl)quinazolin-4(3H)-one;
(S)-2-(1-aminoethyl)-5-chloro-3-(3,5-difluorophenyl)-8-fluoroquinazolin-4(3H)-one;
(S)-2-(1-aminoethyl)-5-chloro-3-(3,5-difluorophenyl)quinazolin-4(3H)-one;
(S)-2-(1-aminoethyl)-3-(3,5-difluorophenyl)-5-fluoroquinazolin-4(3H)-one;
(R)-2-(1-aminoethyl)-5-chloro-3-(3,5-difluorophenyl)quinazolin-4(3H)-one;
(S)-2-(1-aminoethyl)-5-chloro-3-(3-chlorophenyl)quinazolin-4(3H)-one;

(S)-2-(1-aminoethyl)-6-fluoro-3-phenylquinazolin-4(3H)-one;
(S)-3-(2-(1-aminoethyl)-5-chloro-4-oxoquinazolin-3(4H)-yl)benzonitrile;
(S)-3-(2-(1-aminoethyl)-6-fluoro-4-oxoquinazolin-3(4H)-yl)benzonitrile;
(S)-2-(1-aminoethyl)-3-(3-chlorophenyl)-6-fluoroquinazolin-4(3H)-one;
(S)-2-(1-aminoethyl)-5-fluoro-3-(3-fluorophenyl)quinazolin-4(3H)-one;
(S)-2-(1-aminoethyl)-3-(3-fluorophenyl)-5-methylquinazolin-4(3H)-one;
(S)-2-(1-aminopropyl)-3-(3,5-difluorophenyl)-5-fluoroquinazolin-4(3H)-one;
(S)-2-(1-aminopropyl)-3-(3,5-difluorophenyl)-5-methylquinazolin-4(3H)-one;
(S)-3-(2-(1-aminoethyl)-5-fluoro-4-oxoquinazolin-3(4H)-yl)benzonitrile;
(S)-2-(1-aminoethyl)-5-(methylsulfonyl)-3-phenylquinazolin-4(3H)-one;
(S)-2-(1-aminoethyl)-4-oxo-3-phenyl-3,4-dihydroquinazoline-5-carbonitrile;
(S)-2-(1-aminoethyl)-5-fluoro-3-(pyridin-3-yl)quinazolin-4(3H)-one;
(S)-2-(1-aminoethyl)-5-chloro-3-(pyridin-3-yl)quinazolin-4(3H)-one;
(S)-2-(1-aminoethyl)-5-methyl-3-(pyridin-3-yl)quinazolin-4(3H)-one;
(S)-2-(1-aminoethyl)-3-(5-fluoropyridin-3-yl)-5-methylquinazolin-4(3H)-one;
(S)-2-(1-aminoethyl)-5-chloro-3-morpholinoquinazolin-4(3H)-one;
(S)—N-(3-(2-(1-aminoethyl)-5-chloro-4-oxoquinazolin-3(4H)-yl)benzyl)methanesulfonamide;
2-((S)-1-aminoethyl)-5-chloro-3-((1R,5S)-8-methyl-8-azabicyclo[3.2.1]octan-3-yl)quinazolin-4(3H)-one;
(S)-2-(1-aminoethyl)-3-(azepan-1-yl)-5-chloroquinazolin-4(3H)-one;
(S)-2-(1-aminoethyl)-5-chloro-3-(piperazin-1-yl)quinazolin-4(3H)-one;
(S)—N-(3-(2-(1-aminoethyl)-5-methyl-4-oxoquinazolin-3(4H)-yl)benzyl)-N-methylmethanesulfonamide;
(S)—N-(3-(2-(1-aminoethyl)-5-chloro-4-oxoquinazolin-3(4H)-yl)benzyl)-N-methylmethanesulfonamide;
(S)—N-(3-(2-(1-aminoethyl)-5-chloro-4-oxoquinazolin-3(4H)-yl)benzyl)-N-isobutylmethanesulfonamide;
(R)-2-(1-amino-2-hydroxyethyl)-5-chloro-3-phenylquinazolin-4(3H)-one; and
(R)-2-(1-amino-2-methoxyethyl)-5-chloro-3-(3,5-difluorophenyl)quinazolin-4(3H)-one.

Example 2b

Preparation of a Compound of Formula (2)

A. Preparation of a Compound of Formula (2) in which n is 1, $R^2$ is hydroxy, and $R^3$ is phenyl

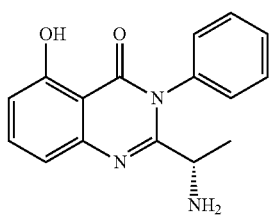

To a solution of (S)-tert-butyl (1-(5-methoxy-4-oxo-3-phenyl-3,4-dihydroquinazolin-2-yl)ethyl)carbamate (100 mg,
0.25 mmol) in DCM (3 mL) at −78° C. was added $BBr_3$ (1M/DCM, 0.63 mL, 0.63 mmol). The reaction was stirred at −78° C. for 20 min, then warmed to ambient temperature. After stirring 10 minutes at ambient temperature, MeOH (5 mL) was added. The reaction was concentrated in vacuo. Purification by flash chromatography (12 g silica, 0-100% EtOAc/DCM then 0-30% MeOH/DCM) provided (S)-2-(1-aminoethyl)-5-hydroxy-3-phenylquinazolin-4(3H)-on as an orange residue. ES/MS 282.1 (M+H$^+$).

Example 3

Preparation of a Compound of Formula (3)

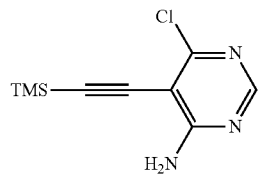 [SMILES: C[Si](C)(C)C#Cc1c(N)ncnc1Cl]

To 4-amino-6-chloro-5-iodopyrimidine (2.0 g, 7.8 mmol) in NMP (20 mL) was added Pd(PPh$_3$)$_4$ (0.907 g, 0.785 mmol), CuI (0.149 g, 0.785 mmol), TEA (2.20 ml, 15.7 mmol), and TMS-alkyne (1.22 mL, 8.64 mmol). After stirring at 90° C. for 1 hour, water was added and the mixture was extracted with EtOAc (3×50 mL), dried (Na$_2$SO$_4$), and concentrated. The residue was purified on a silica column (0-75% ethyl acetate in hexanes) to give 6-chloro-5-((trimethylsilyl)ethynyl)pyrimidin-4-amine. ES/MS m/z=226.1 (M$^+$), 228.1 (M$^{+2}$).

Example 4

Preparation of a Compound of Formula (4)

A. Preparation of a Compound of Formula (4) in which $R^1$ is 5-methoxycarbonylpyridin-2-yl

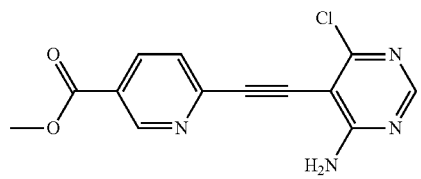 [SMILES: COC(=O)c1ccc(C#Cc2c(N)ncnc2Cl)nc1]

To 6-chloro-5-((trimethylsilyl)ethynyl)pyrimidin-4-amine (30.0 mg, 1.33 mmol) (prepared according to the procedure in Example 3 above) in NMP (5 mL) was added Pd(PPh$_3$)$_4$ (0.154 g, 0.133 mmol), CuI (25 mg, 0.78 mmol), TEA (0.371 mL, 2.66 mmol), tBAF (0.385 mL, 2.66 mmol), and methyl 6-bromonicotinate (0.345 g 1.60 mmol). After stirring at 90° C. overnight, water was added and the mixture was extracted with EtOAc (3×25 mL), dried (Na$_2$SO$_4$), and concentrated. Methyl 6-((4-amino-6-chloropyrimidin-5-yl)ethynyl)nicotinate was carried forward crude. ES/MS m/z=289.1 (M$^+$), 291.0 (M$^{+2}$).

B. Preparation of a Compound of Formula (4), varying $R^1$

Following the procedure described in Example 4A and Reaction Scheme I, but varying the $R^1$ substituent, other compounds of formula (4) were prepared including:

6-chloro-5-(pyridin-2-ylethynyl)pyrimidin-4-amine, ES/MS m/z=231.5 (M+H⁺);
5-((1H-pyrazol-4-yl)ethynyl)-6-chloropyrimidin-4-amine, ES/MS m/z=220 (M+H⁺);
6-chloro-5-((5-fluoropyridin-2-yl)ethynyl)pyrimidin-4-amine, ES/MS m/z=249.5 (M+H⁺);
6-chloro-5-((3-fluoro-5-methoxyphenyl)ethynyl)pyrimidin-4-amine, ES/MS m/z=278.2 (M+H⁺);
6-((4-amino-6-chloropyrimidin-5-yl)ethynyl)benzo[d]thiazol-2-amine, ES/MS m/z=302.5 (M+H⁺);
6-chloro-5-(pyridin-2-ylethynyl)pyrimidin-4-amine, ES/MS m/z=231.2 (M+H⁺);
6-chloro-5-(pyridin-3-ylethynyl)pyrimidin-4-amine, ES/MS m/z=231.1 (M+H⁺);
6-chloro-5-(pyrimidin-5-ylethynyl)pyrimidin-4-amine, ES/MS m/z=232.6 (M+H⁺);
5-((5-aminopyridin-2-yl)ethynyl)-6-chloropyrimidin-4-amine, ES/MS m/z=246.7 (M+H⁺);
5-((4-amino-6-chloropyrimidin-5-yl)ethynyl)pyrimidin-2-amine, ES/MS m/z=247 (M+H⁺);
5-((6-aminopyridin-2-yl)ethynyl)-6-chloropyrimidin-4-amine, ES/MS m/z=246.1 (M+H⁺);
4-(4-amino-6-chloropyrimidin-5-yl)-2-methylbut-3-yn-2-ol, ES/MS m/z=212.3 (M+H⁺);
6-chloro-5-((4-(trifluoromethoxy)phenyl)ethynyl)pyrimidin-4-amine, ES/MS m/z=314.5 (M+H⁺);
6-chloro-5-(cyclopropylethynyl)pyrimidin-4-amine, ES/MS m/z=194 (M+H⁺);
(S)-4-(4-amino-6-chloropyrimidin-5-yl)but-3-yn-2-ol, ES/MS m/z=198.1 (M+H⁺);
(R)-4-(4-amino-6-chloropyrimidin-5-yl)but-3-yn-2-ol, ES/MS m/z=198.2 (M+H⁺);
5-((6-amino-4-(trifluoromethyl)pyridin-3-yl)ethynyl)-6-chloropyrimidin-4 amine, ES/MS m/z=314.7 (M+H⁺);
6-chloro-5-(pyrazin-2-ylethynyl)pyrimidin-4-amine, ES/MS m/z=232.5 (M+H⁺);
6-chloro-5-(pyridazin-3-ylethynyl)pyrimidin-4-amine, ES/MS m/z=232.2 (M+H⁺);
6-chloro-5-((3-fluoro-5-methoxyphenyl)ethynyl)pyrimidin-4-amine;
6-chloro-5-((5-fluoropyridin-2-yl)ethynyl)pyrimidine-2,4-diamine;
6-chloro-5-((3-fluoropyridin-2-yl)ethynyl)pyrimidin-4-amine;
6-chloro-5-((3-methoxypyridin-2-yl)ethynyl)pyrimidin-4-amine;
6-chloro-5-((3,5-difluoropyridin-2-yl)ethynyl)pyrimidin-4-amine;
6-chloro-5-(pyrazin-2-ylethynyl)pyrimidin-4-amine;
6-chloro-5-(pyrimidin-2-ylethynyl)pyrimidin-4-amine;
6-chloro-5-((5-(trifluoromethyl)pyridin-2-yl)ethynyl)pyrimidin-4-amine;
6-chloro-5-((5-methylpyridin-2-yl)ethynyl)pyrimidin-4-amine;
6-chloro-5-((5-(trifluoromethyl)pyridin-2-yl)ethynyl)pyrimidin-4-amine;
6-((4-amino-6-chloropyrimidin-5-yl)ethynyl)nicotinamide;
isopropyl 6-((4-amino-6-chloropyrimidin-5-yl)ethynyl)nicotinate;
6-((4-amino-6-chloropyrimidin-5-yl)ethynyl)nicotinic acid;
6-chloro-5-((5-fluoro-6-methylpyridin-2-yl)ethynyl)pyrimidin-4-amine; 6-chloro-5-((6-methylpyridin-2-yl)ethynyl)pyrimidin-4-amine;
6-chloro-5-((3-(trifluoromethyl)pyridin-2-yl)ethynyl)pyrimidin-4-amine;
6-chloro-5-((3-methylpyridin-2-yl)ethynyl)pyrimidin-4-amine;
6-chloro-5-(cyclopentylethynyl)pyrimidin-4-amine;
6-chloro-5-(cyclohexylethynyl)pyrimidin-4-amine;
6-chloro-5-((4-methylpyridin-2-yl)ethynyl)pyrimidin-4-amine;
6-chloro-5-((4-(trifluoromethyl)pyridin-2-yl)ethynyl)pyrimidin-4-amine;
6-chloro-5-((4-(difluoromethyl)pyridin-2-yl)ethynyl)pyrimidin-4-amine;
6-chloro-5-((4-ethylpyridin-2-yl)ethynyl)pyrimidin-4-amine;
6-chloro-5-((6-methylpyridin-2-yl)ethynyl)pyrimidin-4-amine;
1-(2-((4-amino-6-chloropyrimidin-5-yl)ethynyl)pyridin-3-yl)ethanone;
1-(2-((4-amino-6-chloropyrimidin-5-yl)ethynyl)pyridin-6-yl)ethanone;
(2-((4-amino-6-chloropyrimidin-5-yl)ethynyl)pyridin-4-yl)methanol;
(2-((4-amino-6-chloropyrimidin-5-yl)ethynyl)pyridin-6-yl)methanol;
2-((4-amino-6-chloropyrimidin-5-yl)ethynyl)isonicotinamide;
1-(6-((4-amino-6-chloropyrimidin-5-yl)ethynyl)pyridin-2-yl)ethanol;
methyl 2-((4-amino-6-chloropyrimidin-5-yl)ethynyl)isonicotinate;
5-((6-(aminomethyl)pyridin-2-yl)ethynyl)-6-chloropyrimidin-4-amine;
2-((4-amino-6-chloropyrimidin-5-yl)ethynyl)isonicotinic acid;
1-(3-((4-amino-6-chloropyrimidin-5-yl)ethynyl)phenyl)ethanone;
(3-((4-amino-6-chloropyrimidin-5-yl)ethynyl)phenyl)methanol; and
(2-((4-amino-6-chloropyrimidin-5-yl)ethynyl)pyridin-3-yl)methanol.

Example 5

Preparation of a Compound of Formula (6)

A. Preparation of a Compound of Formula (6) in which n is 1, R² is chloro, and R³ is phenyl

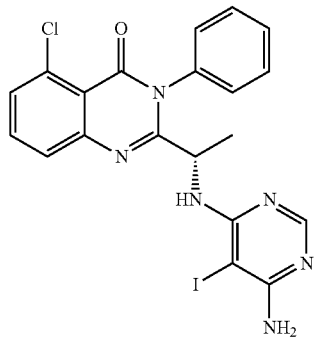 [SMILES: C[C@H](Nc1ncnc(N)c1I)c1nc2cccc(Cl)c2c(=O)n1-c1ccccc1]

To (S)-2-(1-aminoethyl)-5-chloro-3-phenylquinazolin-4(3H)-one (400 mg, 1.33 mmol) (prepared according to the procedure in Example 2a.A above) and 4-amino-6-chloro-5-iodopyrimidine (338 mg, 1.32 mmol) in IPA (5 mL) was added Hunig's base (0.4 mL). After stirring at 90° C. for 2 hours in a microwave reactor, water was added and the mixture was extracted with EtOAc (3×50 mL), dried (MgSO₄), and concentrated. The residue was purified on a reverse phase system run from 0 to 95% ACN in water (0.1% TFA) to give (S)-2-(1-(6-amino-5-iodopyrimidin-4-ylamino)ethyl)-5-chloro-3-phenylquinazolin-4(3H)-one. ES/MS m/z=519.0 (M+), 521.0 (M+2).

Example 6

Preparation of a Compound of Formula (I) or (II)

A. Preparation of a Compound of Formula (I) in which n is 1, R¹ is 5-methoxycarbonylpyridin-2-yl, R² is chloro, and R³ is phenyl (Compound 3a)

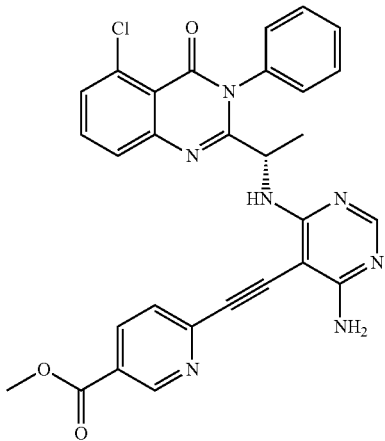 [SMILES: COC(=O)c1ccc(C#Cc2c(N)ncnc2N[C@@H](C)c2nc3cccc(Cl)c3c(=O)n2-c2ccccc2)nc1]

To methyl 6-((4-amino-6-chloropyrimidin-5-yl)ethynyl)nicotinate (50 mg, 0.17 mmol) (prepared according to the procedure in Example 3 above) in NMP (5 mL) was added (S)-2-(1-aminoethyl)-5-chloro-3-phenylquinazolin-4(3H)-one (62 mg 0.21 mmol) (prepared according to the procedure in Example 2A above), KF (33 mg 0.35 mmol), and Hunig's base (0.15 ml, 0.21 mmol). After stirring overnight at 120° C. the reaction was cooled to rt. Water was added. The precipitate was filtered, and then dissolved in DCM. Purification on silica with 0 to 100% EtOAc in hexanes then 0 to 20% MeOH in EtOAc gave material that required further purification. Purification on a reverse phase system run from 0 to 95% ACN in water (0.1% TFA) gave (S)-methyl 6-((4-amino-6-(1-(5-chloro-4-oxo-3-phenyl-3,4-dihydroquinazolin-2-yl)ethylamino)pyrimidin-5-yl)ethynyl)nicotinate.

B. Preparation of a Compound of Formula (I) in which n is 1, R² is chloro, and R¹ and R³ are both phenyl (Compound 51a)

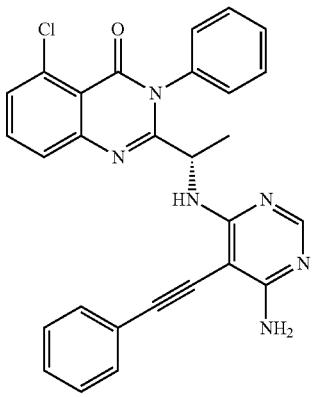 [SMILES: C[C@H](Nc1ncnc(N)c1C#Cc1ccccc1)c1nc2cccc(Cl)c2c(=O)n1-c1ccccc1]

To (S)-2-(1-(6-amino-5-iodopyrimidin-4-ylamino)ethyl)-5-chloro-3-phenylquinazolin-4(3H)-one (58 mg, 0.11 mmol) (prepared according to the procedure in Example 5A) in THF (5 mL) was added Pd(PPh₃)₂Cl₂ (2 mg, 2.5%), CuI (1 mg, 5%), TEA (0.1 mL, 0.16 mmol), and phenylacetylene (20 mg 0.16 mmol). After stirring at 70° C. for 2 hours, the solvent was stripped. The residue was purified on silica with 0 to 10% MeOH in DCM to give material that required further purification. Purification on silica with 0 to 100% EtOAc in hexanes gave (S)-2-(1-(6-amino-5-(phenylethynyl)pyrimidin-4-ylamino)ethyl)-5-chloro-3-phenylquinazolin-4(3H)-one. ¹H NMR (400 MHz, DMSO-D₆) δ7.88 (s, 1H), 7.78 (t, J=8.0 Hz, 1H), 7.88 (dt, J=6.8, 1.6 Hz, 2H), 7.59-7.41 (m, 10H), 6.92 (d, J=7.0 Hz, 1H), 6.75 (bs, 2H), 4.73 (p, J=6.8 Hz, 1H), 1.35 (d, J=6.7 Hz, 3H). ES/MS m/z=493.1 (M+H+).

C. Preparation of a Compound of Formula (I) or (II), varying R¹, R² and R³

Following the procedure described in Examples 6A and 6B, and Reaction Scheme I, but varying the R¹ substituent, other compounds of formula (I) or (II) were prepared including:

(S)-2-(1-(6-amino-5-((5-fluoropyridin-2-yl)ethynyl)pyrimidin-4-ylamino)ethyl)-5,8-difluoro-3-phenylquinazolin-4(3H)-one (Compound 4a); ¹H NMR (400 MHz, DMSO-d6) δ 8.64 (d, 1H, J=2.3 Hz), 8.02 (s, 1H), 7.91-7.82 (m, 2H), 7.80-7.74 (m, 1H), 7.60-7.45 (m, 5H), 7.39-7.31 (m, 3H), 4.91-4.82 (m, 2H), 1.40 (d, 3H, J=6.6 Hz); ES/MS m/z=514.1 (M+H)+;

(S)-2-(1-((6-amino-5-((5-fluoropyridin-2-yl)ethynyl)pyrimidin-4-yl)amino)ethyl)-3-(3,5-difluorophenyl)-5,8-difluoroquinazolin-4(3H)-one (Compound 1a); ¹H NMR (400 MHz, DMSO-d6) δ 8.81-8.39 (m, 1H), 8.06 (s, 1H), 7.95-7.71 (m, 2H), 7.64-7.37 (m, 3H), 7.42-7.08 (m, 3H), 5.01 (t, J=6.9 Hz, 1H), 1.45 (d, J=6.6 Hz, 3H). ES/MS 550.3 (M+H+);

(S)-2-(1-((6-amino-5-((5-fluoropyridin-2-yl)ethynyl)pyrimidin-4-yl)amino)ethyl)-3-(3,5-difluorophenyl)-8-fluoroquinazolin-4(3H)-one (Compound 2a); ¹H NMR (400 MHz, DMSO-d6) δ 8.76-8.44 (m, 1H), 8.05 (s, 1H), 7.98-7.64 (m, 3H), 7.64-7.39 (m, 3H), 7.39-7.13 (m, 2H), 5.19-4.89 (m, 1H), 1.70-1.32 (m, 3H). ES/MS 532.2 (M+H+);

(S)-2-(1-(6-amino-5-((5-fluoropyridin-2-yl)ethynyl)pyrimidin-4-ylamino)ethyl)-8-chloro-3-phenylquinazolin-4(3H)-one (Compound 5a); ¹H NMR (400 MHz, DMSO-d6) δ 8.65 (d, 1H, J=2.8 Hz), 8.09 (s, 1H), 8.07 (s, 1H), 7.99 (d, 1H, J=7.8 Hz), 7.92-7.84 (m, 2H), 7.68-7.47 (m, 8H), 5.09-5.01 (m, 2H), 1.38 (d, 3H, J=6.7 Hz); ES/MS m/z=512.1 (M+H);

(S)-2-(1-(6-amino-5-((5-fluoropyridin-2-yl)ethynyl)pyrimidin-4-ylamino)ethyl)-5-chloro-8-fluoro-3-phenylquinazolin-4(3H)-one (Compound 6a); ¹H NMR (400 MHz, DMSO-d6) δ 8.65 (d, 1H, J=2.7 Hz), 8.06 (s, 1H), 7.91-7.83 (m, 2H), 7.73 (dt, 1H, J=9.0 and 0.8 Hz), 7.65-7.44 (m, 8H), 4.91-4.84 (m, 2H), 1.40 (d, 3H, J=6.7 Hz); ES/MS m/z=530.1 (M+H);

(S)-2-(1-(6-amino-5-((5-fluoropyridin-2-yl)ethynyl)pyrimidin-4-ylamino)ethyl)-3-(3,5-difluorophenyl)-5-fluoroquinazolin-4(3H)-one (Compound 7a); ¹H NMR (400 MHz, DMSO-d6) δ 8.66 (t, J=14.3 Hz, 1H), 8.05 (s, 1H), 7.88 (dtd, J=10.9, 8.5, 4.5 Hz, 2H), 7.65 (d, J=8.2 Hz, 1H), 7.57-6.98 (m, 8H), 5.00-4.69 (m, 1H), 1.33 (d, J=6.6 Hz, 3H). ES/MS m/z=532.2 (M+H+);

(S)-2-(1-(6-amino-5-((5-fluoropyridin-2-yl)ethynyl)pyrimidin-4-ylamino)ethyl)-5-fluoro-3-phenylquinazolin-4(3H)-one (Compound 8a); ¹H NMR (400 MHz, DMSO-d6) δ 8.73 (d, J=2.9 Hz, 1H), 8.01-7.79 (m, 4H), 7.73-7.39 (m, 8H), 7.38-7.17 (m, 2H), 4.85-4.74 (m, 1H), 1.35 (dd, J=13.1, 6.6 Hz, 3H). ES/MS m/z=496.1 (M+H+);

(S)-2-(1-(6-amino-5-((5-fluoropyridin-2-yl)ethynyl)pyrimidin-4-ylamino)ethyl)-5-chloro-3-(3,5-difluorophenyl)quinazolin-4(3H)-one (Compound 9a); ¹H NMR (400 MHz, dmso) δ 8.68 (d, J=2.4 Hz, 1H), 8.01 (s, 1H), 7.97-7.73 (m, 4H), 7.60 (d, J=7.7 Hz, 1H), 7.53 (d, J=8.7 Hz, 2H), 7.38 (m, 8.9 Hz, 4H), 4.97-4.80 (m, 1H), 1.38 (d, J=6.5 Hz, 3H). ES/MS m/z=548.3 (M+H⁺);

(S)-2-(1-(6-amino-5-((5-methoxypyridin-2-yl)ethynyl)pyrimidin-4-ylamino)ethyl)-5,8-dichloro-3-phenylquinazolin-4(3H)-one (Compound 10a); ¹H NMR (400 MHz, DMSO-d6) δ 8.34 (d, 1H, J=3.1 Hz), 8.04 (s, 1H), 7.93 (d, 1H, J=8.6 Hz), 7.76 (d, 1H, J=8.6 Hz), 7.60-7.48 (m, 8H), 7.45-7.32 (br s, 2H), 5.04-4.97 (m, 2H), 1.35 (d, 3H, J=6.6 Hz); ES/MS m/z=558.2 (M+H)⁺;

(S)-2-(1-(6-amino-5-((5-fluoropyridin-2-yl)ethynyl)pyrimidin-4-ylamino)ethyl)-5,8-dichloro-3-phenylquinazolin-4(3H)-one (Compound 11a); ¹H NMR (400 MHz, DMSO-d6) δ 8.65 (d, 1H, J=3.1 Hz), 8.04 (s, 1H), 7.94 (d, 1H, J=8.6 Hz), 7.91-7.84 (m, 2H), 7.60-7.49 (m, 8H), 5.04-4.97 (m, 2H), 1.36 (d, 3H, J=6.7 Hz); ES/MS m/z=546.1 (M+H)⁺;

(S)-2-(1-(6-amino-5-((5-methoxypyridin-2-yl)ethynyl)pyrimidin-4-ylamino)ethyl)-8-fluoro-3-phenylquinazolin-4(3H)-one (Compound 12a); ¹H NMR (400 MHz, DMSO-d6) δ 8.35 (d, 1H, J=3.5 Hz), 8.08 (s, 1H), 7.95 (dm, 1H, J=7.8 Hz), 7.77 (d, 1H, J=8.6 Hz), 7.76-7.67 (m, 2H), 7.60-7.47 (m, 8H), 4.96-4.89 (m, 2H), 1.43 (d, 3H, J=7.1 Hz); ES/MS m/z=508.2 (M+H)⁺;

(S)-2-(1-(6-amino-5-((5-fluoropyridin-2-yl)ethynyl)pyrimidin-4-ylamino)ethyl)-8-fluoro-3-phenylquinazolin-4(3H)-one (Compound 13a); ¹H NMR (400 MHz, DMSO-d6) δ 8.57 (d, 1H, J=2.8 Hz), 7.99 (s, 1H), 7.88 (d, 1H, J=7.8 Hz), 7.84-7.76 (m, 2H), 7.70-7.50 (m, 2H), 7.54-7.35 (m, 6H), 4.89-4.82 (m, 2H), 1.35 (d, 3H, J=6.6 Hz); ES/MS found m/z=496.2 (M+H)⁺;

(S)-2-(1-(6-amino-5-(pyridazin-3-ylethynyl)pyrimidin-4-ylamino)ethyl)-5-chloro-3-phenylquinazolin-4(3H)-one (Compound 14a); ¹H NMR (400 MHz, dmso) δ 13.07-12.79 (m, 1H), 9.15 (s, 1H), 8.93-8.52 (m, 1H), 8.37-7.97 (m, 2H), 8.01-7.47 (m, 8H), 7.40 (s, 2H), 4.81 (s, 1H), 1.49 (d, J=6.8 Hz, 3H). ES/MS m/z=495.2 (M+H⁺);

(S)-2-(1-(6-amino-5-((6-aminopyridin-2-yl)ethynyl)pyrimidin-4-ylamino)ethyl)-5-chloro-3-(3,5-difluorophenyl)quinazolin-4(3H)-one (Compound 15a); ¹H NMR (400 MHz, dmso) δ 7.97 (s, 2H), 7.87 (s, 1H), 7.81-7.69 (m, 1H), 7.67-7.55 (m, 2H), 7.51 (d, J=9.7 Hz, 1H), 7.39 (m, 2H), 7.27 (d, J=10.2 Hz, 1H), 7.24 (d, J=8.6 Hz, 1H), 6.87 (d, J=8.5 Hz, 1H), 4.85 (s, 1H), 1.46 (d, J=6.4 Hz, 3H). ES/MS m/z=545.9 (M+H⁺);

(S)-2-(1-(6-amino-5-(pyrazin-2-ylethynyl)pyrimidin-4-ylamino)ethyl)-5-chloro-3-phenylquinazolin-4(3H)-one (Compound 16a); ¹H NMR (400 MHz, DMSO-d6) δ 9.03 (d, J=1.6 Hz, 1H), 8.78 (dd, J=2.5, 1.6 Hz, 1H), 8.60 (d, J=24.1 Hz, 1H), 8.07 (s, 1H), 7.92-7.68 (m, 2H), 7.64-7.23 (m, 9H), 4.89-4.61 (m, 1H), 1.34 (d, J=6.7 Hz, 3H). ES/MS m/z=495.4 (M+H⁺);

(S)-2-(1-(6-amino-5-((6-amino-4-(trifluoromethyl)pyridin-3-yl)ethynyl)pyrimidin-4-ylamino)ethyl)-5-chloro-3-(3,5-difluorophenyl)quinazolin-4(3H)-one (Compound 17a); ¹H NMR (400 MHz, DMSO-d6) δ 8.43 (d, J=47.4 Hz, 1H), 8.11 (s, 1H), 7.76 (t, J=8.0 Hz, 1H), 7.68-7.34 (m, 6H), 7.32-7.13 (m, 2H), 7.10 (s, 3H), 6.81 (s, 1H), 4.96 (d, J=6.2 Hz, 1H), 1.41 (d, J=6.5 Hz, 3H). ES/MS m/z=613.7 (M+H⁺);

(S)-2-(1-(6-amino-5-((6-amino-4-(trifluoromethyl)pyridin-3-yl)ethynyl)pyrimidin-4-ylamino)ethyl)-5-chloro-3-phenylquinazolin-4(3H)-one (Compound 18a); ¹H NMR (400 MHz, DMSO-d6) δ 8.51 (s, 1H), 8.09 (s, 1H), 7.86-7.60 (m, 1H), 7.63-7.37 (m, 8H), 7.04 (s, 4H), 6.83 (d, J=12.2 Hz, 1H), 5.02-4.52 (m, 1H), 1.35 (d, J=6.7 Hz, 3H). ES/MS m/z=577.5 (M+H⁺);

2-((S)-1-(6-amino-5-((R)-3-hydroxybut-1-ynyl)pyrimidin-4-ylamino)ethyl)-5-chloro-3-phenylquinazolin-4(3H)-one (Compound 19a); ¹H NMR (400 MHz, DMSO-d6) δ 8.08 (s, 1H), 7.83-7.71 (m, 1H), 7.66 (d, J=7.0 Hz, 1H), 7.55 (dd, J=16.0, 14.0 Hz, 10H), 4.84-4.48 (m, 2H), 1.52-1.38 (m, 3H), 1.33 (d, J=6.6 Hz, 3H). ES/MS m/z=461(M+H⁺);

2-((S)-1-(6-amino-5-((S)-3-hydroxybut-1-ynyl)pyrimidin-4-ylamino)ethyl)-5-chloro-3-phenylquinazolin-4(3H)-one (Compound 19b); ¹H NMR (400 MHz, DMSO-d6) δ 8.06 (s, 1H), 7.83-7.69 (m, 1H), 7.67 (dd, J=8.2, 1.1 Hz, 1H), 7.57-7.43 (m, 8H), 7.38-7.07 (m, 2H), 4.89-4.55 (m, 2H), 1.45 (d, J=6.6 Hz, 3H), 1.32 (d, J=6.7 Hz, 3H). ES/MS m/z=461.9 (M+H⁺);

2-((S)-1-(6-amino-5-((R)-3-hydroxybut-1-ynyl)pyrimidin-4-ylamino)ethyl)-5-chloro-3-(3,5-difluorophenyl)quinazolin-4(3H)-one (Compound 20a); ¹H NMR (400 MHz, DMSO-d6) δ 8.05 (s, 1H), 7.79 (t, J=8.1 Hz, 5H), 7.67 (d, J=8.3 Hz, 1H), 7.59 (d, J=7.8 Hz, 1H), 7.52 (d, J=8.1 Hz, 1H), 7.44-7.17 (m, 6H), 4.85 (s, 1H), 4.67 (d, J=6.6 Hz, 1H), 1.41 (dd, J=6.6, 6.6 Hz, 6H). ES/MS m/z=497.1 (M+H⁺);

2-((S)-1-(6-amino-5-((S)-3-hydroxybut-1-ynyl)pyrimidin-4-ylamino)ethyl)-5-chloro-3-(3,5-difluorophenyl)quinazolin-4(3H)-one (Compound 20b); ¹H NMR (400 MHz, DMSO-d6) δ 8.05 (s, 1H), 7.80 (t, J=8.0 Hz, 1H), 7.68 (d, J=8.1 Hz, 1H), 7.59 (d, J=7.9 Hz, 1H), 7.52 (d, J=9.1 Hz, 1H), 7.46-7.10 (m, 6H), 4.85 (s, 1H), 4.66 (d, J=6.6 Hz, 1H), 1.51-1.34 (m, 6H). ES/MS m/z=497.3 (M+H⁺);

(S)-2-(1-(6-amino-5-(cyclopropylethynyl)pyrimidin-4-ylamino)ethyl)-5-chloro-3-(3,5-difluorophenyl)quinazolin-4(3H)-one (Compound 23a); ¹H NMR (400 MHz, DMSO-d6) δ 7.99 (s, 1H), 7.81 (t, J=8.2 Hz, 2H), 7.80 (d, J=8.1 Hz, 2H), 7.62 (dd, J=7.7, 7.9 Hz, 1H), 7.51 (d, J=9.0 Hz, 1H), 7.37 (d, J=9.4 Hz, 1H), 7.27 (d, J=9.2 Hz, 1H), 7.21-7.06 (m, 1H), 4.84 (s, 1H), 1.64 (s, 1H), 1.38 (d, J=6.6 Hz, 3H), 1.01-0.73 (m, 4H). ES/MS m/z=494.5 (M+H⁺);

(S)-2-(1-(6-amino-5-(cyclopropylethynyl)pyrimidin-4-ylamino)ethyl)-5-chloro-3-phenylquinazolin-4(3H)-one (Compound 24a); ¹H NMR (400 MHz, DMSO-d6) δ 8.05 (s, 1H), 7.80 (t, J=8.0 Hz, 1H), 7.63 (dd, J=8.2, 1.2 Hz, 1H), 7.59 (dd, J=7.8, 1.1 Hz, 1H), 7.56-7.54 (m, 2H), 7.49 (dd, J=4.5, 3.1 Hz, 4H), 7.34 (s, 2H), 4.83-4.66 (m, 1H), 1.69 (ddd, J=13.1, 8.2, 5.1 Hz, 1H), 1.33 (d, J=6.7 Hz, 3H), 1.05-0.73 (m, 4H). ES/MS m/z=457.2 (M+H⁺);

(S)-2-(1-(6-amino-5-((4-(trifluoromethoxy)phenyl)ethynyl)pyrimidin-4-ylamino)ethyl)-5-chloro-3-(3,5-difluorophenyl)quinazolin-4(3H)-one (Compound 26a); ¹H NMR (400 MHz, DMSO-d6) δ 8.04 (s, 1H), 7.87-7.81 (m, 2H), 7.78 (t, J=8.0 Hz, 1H), 7.60 (dd, J=12.2, 4.5 Hz, 3H), 7.52 (d, J=9.1 Hz, 1H), 7.44 (d, J=8.5 Hz, 2H), 7.36 (t, J=9.3 Hz, 2H), 7.29 (d, J=9.2 Hz, 1H), 5.00-4.81 (m, 1H), 1.45 (d, J=6.7 Hz, 3H). ES/MS m/z=613.9 (M+H⁺);

(S)-2-(1-(6-amino-5-((4-(trifluoromethoxy)phenyl)ethynyl)pyrimidin-4-ylamino)ethyl)-5-chloro-3-phenylquinazolin-4(3H)-one (Compound 27a); ¹H NMR (400 MHz, DMSO-d6) δ 8.04 (s, 1H), 7.89-7.80 (m, 1H), 7.80-7.64 (m, 1H), 7.64-7.26 (m, 13H), 4.88-4.64 (m, 1H), 1.38 (d, J=6.7 Hz, 3H). ES/MS m/z=577.2 (M+H⁺);

(S)-2-(1-(6-amino-5-(3-hydroxy-3-methylbut-1-ynyl)pyrimidin-4-ylamino)ethyl)-5-chloro-3-(3,5-difluorophenyl)quinazolin-4(3H)-one (Compound 28a); ¹H NMR (400 MHz, DMSO-d6) δ 8.04 (s, 1H), 7.84-7.75 (m, 2H), 7.67 (dd, J=8.2, 1.2 Hz, 1H), 7.60 (dd, J=7.8, 1.2 Hz, 1H), 7.54 (d, J=8.8 Hz, 1H), 7.42 (d, J=9.2 Hz, 1H), 7.35 (d, J=9.1 Hz, 1H), 7.10 (s, 2H), 4.85 (s, 1H), 1.52 (d, J=3.8 Hz, 6H), 1.38 (d, J=6.7 Hz, 3H). ES/MS m/z=511.9 (M+H⁺);

(S)-2-(1-(6-amino-5-(3-hydroxy-3-methylbut-1-ynyl)pyrimidin-4-ylamino)ethyl)-5-chloro-3-phenylquinazolin-4(3H)-one (Compound 29a); ¹H NMR (400 MHz, DMSO-d6) δ 8.08 (s, 1H), 7.79 (t, J=8.0 Hz, 1H), 7.71-7.63 (m, 1H), 7.60-7.46 (m, 8H), 7.30 (s, 2H), 4.89-4.61 (m, 1H), 1.54 (d, J=4.0 Hz, 6H), 1.32 (d, J=6.6 Hz, 3H). ES/MS m/z=475.9 (M+H⁺);

(S)-2-(1-(6-amino-5-(pyridin-2-ylethynyl)pyrimidin-4-ylamino)ethyl)-5-methyl-3-phenylquinazolin-4(3H)-one (Compound 30a); ¹H NMR (400 MHz, DMSO-d6) δ 8.71 (s, 1H), 8.33-8.20 (m, 1H), 8.04 (s, 1H), 7.94-7.83 (m, 1H), 7.80-7.64 (m, 2H), 7.46 (dd, J=64.5, 30.9 Hz, 10H), 4.79 (s, 1H), 2.79-2.53 (m, 3H), 1.29 (dd, J=24.6, 6.7 Hz, 5H). ES/MS m/z=474.5 (M+H⁺);

(S)-2-(1-(6-amino-5-((6-aminopyridin-2-yl)ethynyl)pyrimidin-4-ylamino)ethyl)-5-chloro-3-phenylquinazolin-4(3H)-one (Compound 31a); ¹H NMR (400 MHz, DMSO-d6) δ 8.01 (s, 1H), 7.88 (s, 1H), 7.76 (t, J=8.0 Hz, 1H), 7.55 (m, 9H), 7.23 (d, J=7.7 Hz, 2H), 6.88 (d, J=8.9 Hz, 1H), 4.84-4.53 (m, 1H), 1.42 (d, J=6.8 Hz, 3H). ES/MS m/z=509.3 (M+H⁺);

(S)-2-(1-(6-amino-5-((2-aminopyrimidin-5-yl)ethynyl)pyrimidin-4-ylamino)ethyl)-5-chloro-3-(3,5-difluorophenyl)quinazolin-4(3H)-one (Compound 32a); ¹H NMR (400 MHz, DMSO-d6) δ 8.56 (s, 2H), 8.16 (s, 1H), 7.81 (dd, J=22.0, 13.9 Hz, 1H), 7.72-7.47 (m, 7H), 7.39 (s, 1H), 7.32 (d, J=8.9 Hz, 1H), 7.21 (s, 1H), 4.95 (s, 1H), 1.48 (d, J=6.7 Hz, 3H). ES/MS m/z=546.5 (M+H⁺);

(S)-2-(1-(6-amino-5-((2-aminopyrimidin-5-yl)ethynyl)pyrimidin-4-ylamino)ethyl)-5-chloro-3-phenylquinazolin-4(3H)-one (Compound 33a); ¹H NMR (400 MHz, DMSO-d6) δ 8.68-8.47 (m, 2H), 8.16 (s, 1H), 7.91 (d, J=26.6 Hz, 1H), 7.77 (t, J=8.0 Hz, 2H), 7.62-7.39 (m, 8H), 7.24 (s, 2H), 4.92-4.73 (m, 1H), 1.43 (d, J=6.8 Hz, 3H). ES/MS m/z=510.1 (M+H⁺);

(S)-2-(1-(6-amino-5-((5-aminopyridin-2-yl)ethynyl)pyrimidin-4-ylamino)ethyl)-5-chloro-3-(3,5-difluorophenyl)quinazolin-4(3H)-one (Compound 34a); ¹H NMR (400 MHz, DMSO-d6) δ 8.31 (s, 1H), 8.06 (s, 1H), 8.03 (d, J=2.6 Hz, 1H), 7.88 (d, J=8.2 Hz, 1H), 7.83-7.77 (m, 1H), 7.71 (dd, J=14.0, 9.7 Hz, 3H), 7.62 (d, J=7.7 Hz, 2H), 7.55 (d, J=8.2 Hz, 2H), 7.46-7.37 (m, 2H), 7.33 (d, J=9.0 Hz, 2H), 7.27 (m, 1H), 4.95-4.89 (m, 1H), 1.45 (d, J=6.6 Hz, 3H). ES/MS m/z=545.9 (M+H⁺);

(S)-2-(1-(6-amino-5-((5-aminopyridin-2-yl)ethynyl)pyrimidin-4-ylamino)ethyl)-5-chloro-3-phenylquinazolin-4(3H)-one (Compound 35a); ¹H NMR (400 MHz, DMSO-d6) δ 8.09 (d, J=12.3 Hz, 2H), 7.84-7.67 (m, 4H), 7.67-7.47 (m, 6H), 7.25 (s, 1H), 4.93-4.62 (m, 1H), 1.35 (dd, J=42.9, 6.8 Hz, 3H). ES/MS m/z=508.3 (M+H⁺);

(S)-2-(1-(6-amino-5-(pyridin-2-ylethynyl)pyrimidin-4-yl)piperidin-2-yl)-5-chloro-3-phenylquinazolin-4(3H)-one (Compound 36a); ¹H NMR (400 MHz, DMSO-D₆) δ 8.61 (d, J=5.5 Hz, 1H), 8.08 (s, 1H), 7.88 (t, J=9.5 Hz, 1H), 7.78-7.38 (m, 10H), 5.15 (m, 1H), 4.72 (m, 1H), 4.09 (m, 1H), 2.16-1.41 (m, 8H); ES/MS m/z=534.1 (M+H)⁺;

(S)-2-(1-(6-amino-5-(pyridin-2-ylethynyl)pyrimidin-4-yl)pyrrolidin-2-yl)-5-chloro-3-phenylquinazolin-4(3H)-one (Compound 37a); ¹H NMR (400 MHz, DMSO-D6) δ 8.63 (m, 1H), 8.23 (d, J=14.2 Hz, 1H), 7.97-7.39 (m, 11H), 4.64 (m, 1H), 4.41 (m, 1H), 4.25 (m, 1H), 2.37-2.09 (m, 4H), 1.94 (m, 2H); ES/MS m/z=520.1 (M+H)⁺;

(S)-3-(2-(1-(6-amino-5-(pyridin-2-ylethynyl)pyrimidin-4-ylamino)ethyl)-5-chloro-4-oxoquinazolin-3(4H)-yl)benzamide (Compound 38a); ¹H NMR (400 MHz, DMSO-d6) δ 8.75 (d, J=4.9 Hz, 1H), 8.13 (d, J=11.7 Hz, 1H), 8.11-7.82 (m, 5H), 7.82-7.44 (m, 5H), 4.89-4.69 (m, 1H), 1.39 (dd, J=6.1, 3.7 Hz, 3H). ES/MS m/z=537.5 (M+H⁺);

(S)-3-(2-(1-(6-amino-5-(pyridin-2-ylethynyl)pyrimidin-4-ylamino)ethyl)-5-chloro-4-oxoquinazolin-3(4H)-yl)-N-ethylbenzenesulfonamide (Compound 39a); ¹H NMR (400 MHz, DMSO-d6) δ 8.74 (d, J=4.9 Hz, 1H), 8.44-7.72 (m, 9H), 7.69-7.55 (m, 1H), 7.55-7.42 (m, 1H), 4.80 (d, J=32.4 Hz, 2H), 3.26-3.02 (m, 1H), 3.00-2.68 (m, 2H), 1.40 (dd, J=6.6, 4.3 Hz, 3H), 1.00 (dt, J=23.1, 7.2 Hz, 3H). ES/MS m/z=601.1 (M+H⁺);

(S)-3-(2-(1-(6-amino-5-(pyridin-2-ylethynyl)pyrimidin-4-ylamino)ethyl)-5-chloro-4-oxoquinazolin-3(4H)-yl)benzenesulfonamide (Compound 40a); ¹H NMR (400 MHz, DMSO-d6) δ 8.81-8.68 (m, 1H), 8.21-8.02 (m, 2H), 8.04-7.72 (m, 7H), 7.65-7.42 (m, 4H), 4.84 (d, J=6.7 Hz, 1H), 4.71 (s, 1H), 1.40 (dd, J=17.0, 6.6 Hz, 3H). ES/MS m/z=573(M+H⁺);

(S)-2-(1-(6-amino-5-(pyrimidin-5-ylethyl)pyrimidin-4-ylaminoethyl)-5-chloro-3-(3,5-difluorophenyl)quinazolin-4(3H)-one (Compound 41a); ¹H NMR (400 MHz, DMSO-d6) δ 9.14 (m, 2H), 8.10 (s, 1H), 7.80 (t, J=8.1 Hz, 2H), 7.70-7.48 (m, 3H), 7.46-7.20 (m, 2H), 5.07-4.82 (m, 1H), 1.44 (t, J=34.5 Hz, 3H). ES/MS m/z=531.4 (M+H⁺);

(S)-2-(1-(6-amino-5-(pyrimidin-5-ylethynyl)pyrimidin-4-ylamino)ethyl)-5-chloro-3-phenylquinazolin-4(3H)-one (Compound 42a); ¹H NMR (400 MHz, DMSO-d6) δ 8.27-8.10 (m, 2H), 7.99 (s, 2H), 7.83-7.67 (m, 2H), 7.55 (m, 6H), 4.95-4.77 (m, 1H), 1.45 (d, J=6.8 Hz, 3H). ES/MS m/z=495.6 (M+H⁺);

(S)-2-(1-(6-amino-5-(pyridin-3-ylethynyl)pyrimidin-4-ylamino)ethyl)-5-chloro-3-(3,5-difluorophenyl)quinazolin-4(3H)-one (Compound 43a); ¹H NMR (400 MHz, DMSO-d6) δ 8.93 (s, 1H), 8.60 (s, 1H), 8.13 (d, J=12.6 Hz, 2H), 7.90-7.71 (m, 2H), 7.50 (ddd, J=91.6, 25.8, 8.8 Hz, 5H), 4.96 (s, 1H), 1.48 (d, J=6.6 Hz, 3H). ES/MS m/z=530.3 (M+H⁺);

(S)-2-(1-(6-amino-5-(pyridin-3-ylethynyl)pyrimidin-4-ylamino)ethyl)-5-chloro-3-phenylquinazolin-4(3H)-one (Compound 44a); ¹H NMR (400 MHz, DMSO-d6) δ 8.96 (d, J=1.3 Hz, 1H), 8.62 (dd, J=4.9, 1.7 Hz, 1H), 8.30-8.03 (m, 2H), 7.98 (s, 1H), 7.87-7.69 (m, 2H), 7.66-7.30 (m, 6H), 4.93-4.69 (m, 1H), 1.44 (d, J=6.7 Hz, 3H)). ES/MS m/z=494.1 (M+H⁺);

(S)-2-(1-(6-amino-5-(pyridin-2-ylethynyl)pyrimidin-4-ylamino)ethyl)-5-chloro-3-(3,5-difluorophenyl)quinazolin-4(3H)-one (Compound 45a); ¹H NMR (400 MHz, DMSO-d6) δ 8.71 (d, J=4.9 Hz, 1H), 8.09 (s, 1H), 7.94 (t, J=7.0 Hz, 1H), 7.89-7.78 (m, 3H), 7.73 (s, 1H), 7.62 (dd, J=6.9, 1.7 Hz, 1H), 7.46 (ddd, J=35.6, 32.4, 9.1 Hz, 6H), 5.03-4.84 (m, 1H), 1.43 (d, J=6.6 Hz, 3H). ES/MS m/z=529.3 (M+H⁺);

(S)-2-(1-(6-amino-5-((2-aminobenzo[d]thiazol-6-yl)ethynyl)pyrimidin-4-ylamino)ethyl)-5-chloro-3-phenylquinazolin-4(3H)-one (Compound 46a); ¹H NMR (400 MHz, DMSO-d6) δ 8.14 (s, 1H), 8.06 (s, 1H), 7.87 (s, 3H), 7.76 (t, J=7.6 Hz, 1H), 7.64-7.47 (m, 8H), 7.40 (d, J=8.2 Hz, 1H), 4.92-4.70 (m, 1H), 1.42 (d, J=6.6 Hz, 3H). ES/MS m/z=565.2 (M+H⁺);

(S)-2-(1-(6-amino-5-((3-fluoro-5-methoxyphenyl)ethynyl)pyrimidin-4-ylamino)ethyl)-5-chloro-3-phenylquinazolin-4(3H)-one (Compound 47a); ¹H NMR (400 MHz, DMSO-d6) δ 8.08 (s, 1H), 7.75 (t, J=8.0 Hz, 1H), 7.67 (s, 1H), 7.55 (dt, J=24.9, 7.1 Hz, 8H), 7.31-7.18 (m, 2H), 6.92 (d, J=11.1 Hz, 1H), 4.85-4.68 (m, 1H), 3.82 (d, J=1.0 Hz, 3H), 1.40 (d, J=6.7 Hz, 3H). ES/MS m/z=541.1 (M+H⁺);

(S)-2-(1-(6-amino-5-((5-fluoropyridin-2-yl)ethynyl)pyrimidin-4-ylamino)ethyl)-5-chloro-3-phenylquinazolin-4(3H)-one (Compound 48a); ¹H NMR (400 MHz, DMSO-d6) δ 8.66 (d, J=3.0 Hz, 1H), 7.88 (dd, J=8.0, 4.0 Hz, 1H), 7.85-

7.71 (m, 4H), 7.64-7.35 (m, 6H), 7.11 (d, J=6.9 Hz, 1H), 6.83 (s, 2H), 4.67 (p, J=6.5 Hz, 1H), 1.24 (d, J=6.6 Hz, 3H). ES/MS m/z=512.1 (M+H$^+$);

(S)-2-(1-(5-((1H-pyrazol-4-yl)ethynyl)-6-aminopyrimidin-4-ylamino)ethyl)-5-chloro-3-phenylquinazolin-4(3H)-one (Compound 49a); $^1$H NMR (400 MHz, DMSO-d6) δ 8.11 (s, 1H), 8.01 (s, 2H), 7.76 (t, J=7.6 Hz, 2H), 7.66-7.48 (m, 6H), 4.87-4.69 (m, 2H), 1.39 (d, J=6.5 Hz, 3H). ES/MS m/z=483.1 (M+H$^+$);

(S)-2-(1-(6-amino-5-(pyridin-2-ylethynyl)pyrimidin-4-ylamino)ethyl)-5-chloro-3-phenylquinazolin-4(3H)-one (Compound 50a); $^1$H NMR (400 MHz, dmso-d6) δ 8.75 (d, J=3.9 Hz, 1H), 8.32-8.10 (m, 1H), 8.12-7.70 (m, 5H), 7.73-7.31 (m, 6H), 4.85 (dd, J=13.0, 6.4 Hz, 1H), 1.40 (dd, J=19.9, 6.7 Hz, 3H). ES/MS m/z=494.1 (M+H$^+$);

(S)-2-(1-((6-amino-5-((5-fluoropyridin-2-yl)ethynyl)pyrimidin-4-yl)amino)ethyl)-5-hydroxy-3-phenylquinazolin-4(3H)-one (Compound 52a); $^1$H NMR (400 MHz, DMSO-d$_6$) δ 11.48 (s, 1H), 8.70 (d, J=2.9 Hz, 1H), 8.09 (s, 1H), 7.96-7.82 (m, 3H), 7.78 (t, J=8.2 Hz, 1H), 7.70-7.45 (m, 6H), 7.28 (dd, J=8.0, 1.0 Hz, 1H), 6.92 (dd, J=8.2, 1.0 Hz, 1H), 4.91-4.80 (m, 1H), 1.35 (d, J=6.5 Hz, 3H). ES/MS 494.2 (M+H$^+$);

(S)-2-(1-((6-amino-5-((5-fluoropyridin-2-yl)ethynyl)pyrimidin-4-yl)amino)ethyl)-5-chloro-8-methyl-3-phenylquinazolin-4(3H)-one (Compound 53a); $^1$H NMR (400 MHz, DMSO-d$_6$) δ 8.65-8.62 (m, 1H), 8.00 (s, 1H), 7.94-7.88 (m, 1H), 7.88-7.80 (m, 1H), 7.65-7.60 (m, 1H), 7.60-7.47 (m, 5H), 7.44 (d, J=8.1 Hz, 1H), 7.25 (d, J=7.7 Hz, 2H), 5.00-4.86 (m, 1H), 2.41 (s, 3H), 1.33 (d, J=6.5 Hz, 3H). ES/MS 526.1 (M+H$^+$);

(S)-2-(1-((6-amino-5-((5-fluoropyridin-2-yl)ethynyl)pyrimidin-4-yl)amino)ethyl)-5-methyl-3-phenylquinazolin-4(3H)-one (Compound 54a); $^1$H NMR (400 MHz, DMSO-d$_6$) δ 8.74-8.69 (m, 1H), 8.08 (s, 1H), 7.97-7.91 (m, 1H), 7.90-7.82 (m, 2H), 7.75 (dd, J=8.1, 7.3 Hz, 1H), 7.68 (dd, J=8.2, 1.3 Hz, 1H), 7.62-7.37 (m, 6H), 7.34-7.27 (m, 1H), 4.85-4.74 (m, 1H), 2.70 (s, 3H), 1.32 (d, J=6.6 Hz, 3H). ES/MS 492.2 (M+H$^+$);

(S)-2-(1-((6-amino-5-(pyrazin-2-ylethynyl)pyrimidin-4-yl)amino)ethyl)-4-oxo-3-phenyl-3,4-dihydroquinazoline-5-carbonitrile (Compound 55a); $^1$H NMR (400 MHz, DMSO-d$_6$) δ 9.03 (d, J=1.5 Hz, 1H), 8.78 (dd, J=2.6, 1.5 Hz, 1H), 8.63 (d, J=2.6 Hz, 1H), 8.14 (dd, J=7.6, 1.9 Hz, 1H), 8.11-8.00 (m, 3H), 7.72 (s, 1H), 7.64-7.41 (m, 6H), 4.90-4.74 (m, 1H), 1.36 (d, J=6.6 Hz, 3H). ES/MS 486.2 (M+H$^+$);

(S)-2-(1-((6-amino-5-((5-fluoropyridin-2-yl)ethynyl)pyrimidin-4-yl)amino)ethyl)-8-methyl-3-phenylquinazolin-4(3H)-one (Compound 56a); $^1$H NMR (400 MHz, DMSO-d$_6$) δ 8.64 (dt, J=2.9, 0.7 Hz, 1H), 8.06 (s, 1H), 7.98-7.93 (m, 1H), 7.92-7.89 (m, 1H), 7.85 (td, J=8.6, 2.9 Hz, 1H), 7.69 (ddd, J=7.4, 1.6, 0.9 Hz, 1H), 7.59-7.46 (m, 7H), 7.43 (t, J=7.6 Hz, 1H), 5.07-4.95 (m, 1H), 2.45 (s, 3H), 1.36 (d, J=6.5 Hz, 3H). ES/MS 492.2 (M+H$^+$);

(S)-2-(1-((6-amino-5-((5-fluoropyridin-2-yl)ethynyl)pyrimidin-4-yl)amino)ethyl)-3-(3-butylphenyl)-5-chloroquinazolin-4(3H)-one (Compound 57a); $^1$H NMR (400 MHz, DMSO) δ 8.77-8.67 (m, 1H), 8.11-7.97 (m, 1H), 7.97-7.74 (m, 3H), 7.62-7.54 (m, 1H), 7.48-7.37 (m, 2H), 7.37-7.24 (m, 3H), 4.90-4.75 (m, 1H), 2.62 (dt, J=26.3, 7.7 Hz, 2H), 1.55 (dq, J=24.3, 7.9 Hz, 2H), 1.38-1.22 (m, 5H), 0.87 (dtd, J=22.5, 7.4, 1.7 Hz, 3H). ES/MS 568.2 (M+H$^+$);

(S)-2-(1-((6-amino-5-((5-fluoropyridin-2-yl)ethynyl)pyrimidin-4-yl)amino)ethyl)-5-chloro-3-(3-(methylsulfonyl)phenyl)quinazolin-4(3H)-one (Compound 58a); $^1$H NMR (400 MHz, DMSO) δ 8.67 (dd, J=6.9, 2.7 Hz, 1H), 8.22 (dt, J=9.4, 2.0 Hz, 1H), 8.09-7.96 (m, 1H), 7.96-7.72 (m, 6H), 7.58 (ddd, J=7.7, 3.8, 1.6 Hz, 1H), 7.06 (dd, J=35.8, 7.1 Hz, 1H), 6.82 (s, 2H), 4.72 (q, J=6.8 Hz, 1H), 3.29 (s, 1.5H), 3.21 (s, 1.5H), 1.36-1.28 (m, 3H). ES/MS 590.1 (M+H$^+$);

(S)-2-(1-((6-amino-5-((5-fluoropyridin-2-yl)ethynyl)pyrimidin-4-yl)amino)ethyl)-3-(3-(tert-butyl)phenyl)-5-chloroquinazolin-4(3H)-one (Compound 59a); $^1$H NMR (400 MHz, DMSO) δ 8.77-8.68 (m, 1H), 8.11-7.98 (m, 1H), 7.99-7.74 (m, 3H), 7.66-7.55 (m, 2H), 7.55-7.40 (m, 3H), 7.41-7.29 (m, 1H), 4.95-4.70 (m, 1H), 1.37-1.20 (m, 12H). ES/MS 568.2 (M+H$^+$);

(S)-3-([1,1'-biphenyl]-3-yl)-2-(1-((6-amino-5-((5-fluoropyridin-2-yl)ethynyl)pyrimidin-4-yl)amino)ethyl)-5-chloroquinazolin-4(3H)-one (Compound 60a); $^1$H NMR (400 MHz, DMSO) δ 8.72 (dd, J=6.0, 2.8 Hz, 1H), 8.02 (d, J=2.1 Hz, 1H), 7.99-7.90 (m, 2H), 7.91-7.75 (m, 5H), 7.74-7.60 (m, 3H), 7.63-7.53 (m, 2H), 7.54-7.31 (m, 4H), 5.03-4.88 (m, 1H), 1.38 (dd, J=6.5, 2.9 Hz, 3H). ES/MS 588.2 (M+H$^+$);

(S)-2-(1-((6-amino-5-((5-fluoropyridin-2-yl)ethynyl)pyrimidin-4-yl)amino)ethyl)-5-chloro-3-(3-ethylphenyl)quinazolin-4(3H)-one (Compound 61a); $^1$H NMR (400 MHz, DMSO) δ 8.72 (dd, J=13.0, 2.7 Hz, 1H), 8.03 (d, J=19.3 Hz, 1H), 7.97-7.72 (m, 3H), 7.62-7.53 (m, 1H), 7.48-7.39 (m, 3H), 7.32 (q, J=10.6, 9.2 Hz, 3H), 4.93-4.74 (m, 1H), 2.73-2.56 (m, 2H), 1.38-1.29 (m, 3H), 1.26-1.11 (m, 3H). ES/MS 540.2 (M+H$^+$);

(S)-2-(1-((6-amino-5-((5-fluoropyridin-2-yl)ethynyl)pyrimidin-4-yl)amino)ethyl)-8-fluoro-5-methyl-3-phenylquinazolin-4(3H)-one (Compound 62a); $^1$H NMR (400 MHz, DMSO) δ 8.63 (dt, J=2.8, 0.8 Hz, 1H), 8.08 (s, 1H), 7.93-7.79 (m, 2H), 7.74 (br s, 1H), 7.66-7.41 (m, 8H), 7.29 (ddd, J=8.3, 5.0, 1.0 Hz, 1H), 4.92-4.84 (m, 1H), 2.65 (s, 3H), 1.39 (d, J=6.7 Hz, 3H). ES/MS 510.2 (M+H$^+$);

(S)-2-(1-((6-amino-5-((5-fluoropyridin-2-yl)ethynyl)pyrimidin-4-yl)amino)ethyl)-8-fluoro-5-methyl-3-phenylquinazolin-4(3H)-one (Compound 63a); $^1$H NMR (400 MHz, DMSO) δ 8.03 (s, 1H), 7.78 (td, J=9.6, 4.2 Hz, 1H), 7.65-7.41 (m, 7H), 7.34 (td, J=9.8, 3.7 Hz, 1H), 7.24-7.19 (m, 2H), 6.90 (dt, J=11.1, 2.4 Hz, 1H), 4.86-4.78 (m, 1H), 3.82 (s, 3H), 1.40 (d, J=6.7 Hz, 3H). ES/MS 543.2 (M+H$^+$);

(S)-2-(1-((6-amino-5-((3-fluoro-5-methoxyphenyl)ethynyl)pyrimidin-4-yl)amino)ethyl)-8-fluoro-3-phenylquinazolin-4(3H)-one (Compound 64a); $^1$H NMR (400 MHz, DMSO) δ 8.05 (s, 1H), 7.96-7.92 (m, 1H), 7.78-7.72 (m, 1H), 7.65-7.34 (m, 7H), 7.22-7.17 (m, 2H), 6.89 (dt, J=11.1, 2.4 Hz, 1H), 4.90-4.83 (m, 1H), 3.80 (s, 3H), 1.41 (d, J=6.7 Hz, 3H). ES/MS 525.2 (M+H$^+$);

(S)-2-(1-((6-amino-5-((3-fluoro-5-methoxyphenyl)ethynyl)pyrimidin-4-yl)amino)ethyl)-5-fluoro-3-phenylquinazolin-4(3H)-one (Compound 65a); $^1$H NMR (400 MHz, DMSO) δ 8.05 (s, 1H), 7.81 (td, J=8.2, 5.4 Hz, 1H), 7.66-7.44 (m, 7H), 7.35-7.18 (m, 3H), 6.91 (dt, J=11.1, 2.4 Hz, 1H), 4.80-4.71 (m, 1H), 3.81 (s, 3H), 1.39 (d, J=6.7 Hz, 3H). ES/MS 525.2 (M+H$^+$);

(S)-2-(1-((6-amino-5-(pyrazin-2-ylethynyl)pyrimidin-4-yl)amino)ethyl)-5-(difluoromethyl)-3-(3,5-difluorophenyl)quinazolin-4(3H)-one (Compound 66a); $^1$H NMR (400 MHz, DMSO) δ 8.99 (d, J=1.6 Hz, 1H), 8.72 (dd, J=2.6, 1.5 Hz, 1H), 8.60 (d, J=2.6 Hz, 1H), 8.07-7.71 (m, 6H), 7.59-7.50 (m, 2H), 7.45-7.25 (m, 3H), 5.01-4.92 (m, 1H), 1.42 (d, J=6.6 Hz, 3H). ES/MS 547.2 (M+H$^+$);

(S)-2-(1-((6-amino-5-((5-fluoropyridin-2-yl)ethynyl)pyrimidin-4-yl)amino)ethyl)-5-(difluoromethyl)-3-phenylquinazolin-4(3H)-one (Compound 67a); $^1$H NMR (400 MHz, DMSO) δ 8.74 (dd, J=3.0, 0.7 Hz, 1H), 8.11-7.73 (m, 9H), 7.65-7.47 (m, 6H), 4.90-4.82 (m, 1H), 1.36 (d, J=6.6 Hz, 3H). ES/MS 528.2 (M+H$^+$);

(S)-2-(1-((6-amino-5-((5-fluoropyridin-2-yl)ethynyl)pyrimidin-4-yl)amino)ethyl)-3-phenyl-5-(trifluoromethyl)

quinazolin-4(3H)-one (Compound 68a): $^1$H NMR (400 MHz, DMSO) δ 8.75 (dd, J=2.9, 0.8 Hz, 1H), 8.21-8.16 (m, 1H), 8.13-8.03 (m, 2H), 8.01-7.92 (m, 2H), 7.87 (td, J=8.7, 2.9 Hz, 1H), 7.62-7.49 (m, 6H), 4.87-4.78 (m, 1H), 1.35 (d, J=6.6 Hz, 3H). ES/MS 545.2 (M+H$^+$);

(S)-2-(1-((6-amino-5-((5-fluoropyridin-2-yl)ethynyl)pyrimidin-4-yl)amino)ethyl)-5-fluoro-8-methyl-3-phenylquinazolin-4(3H)-one (Compound 69a): $^1$H NMR (400 MHz, DMSO) δ 8.64 (dd, J=3.0, 0.7 Hz, 1H), 8.03 (s, 1H), 7.91 (ddd, J=8.7, 4.8, 0.7 Hz, 1H), 7.85 (td, J=8.6, 2.9 Hz, 1H), 7.67 (dd, J=8.4, 5.5 Hz, 1H), 7.58-7.30 (m, 8H), 7.20 (dd, J=11.0, 8.3 Hz, 1H), 5.01-4.92 (m, 1H), 2.39 (s, 3H), 1.34 (d, J=6.6 Hz, 3H). ES/MS 510.2 (M+H$^+$);

(S)-3-(2-(1-((6-amino-5-((5-fluoropyridin-2-yl)ethynyl)pyrimidin-4-yl)amino)ethyl)-5-(difluoromethyl)-4-oxoquinazolin-3(4H)-yl)benzonitrile (Compound 70a): $^1$H NMR (400 MHz, DMSO) δ 8.67 (dd, J=3.1, 2.4 Hz, 1H), 8.20 (t, J=1.8 Hz, 1H), 8.11-7.80 (m, 11H), 7.77-7.66 (m, 1H), 4.90-4.82 (s, 1H), 1.39 (d, J=6.6 Hz, 3H). ES/MS 553.2 (M+H$^+$);

(S)-3-(2-(1-((6-amino-5-(pyrazin-2-ylethynyl)pyrimidin-4-yl)amino)ethyl)-5-(difluoromethyl)-4-oxoquinazolin-3(4H)-yl)benzonitrile (Compound 71a): $^1$H NMR (400 MHz, DMSO) 69.00 (dd, J=1.6, 1.0 Hz, 1H), 8.72 (dt, J=2.6, 1.7 Hz, 1H), 8.59 (d, J=2.6, 0.8 Hz, 1H), 8.21-8.17 (m, 1H), 8.06-7.82 (m, 8H), 7.75-7.65 (m, 1H), 4.92-4.84 (m, 1H), 1.40 (d, J=6.6 Hz, 3H). ES/MS 536.2 (M+H$^+$);

(S)-3-(2-(1-((6-amino-5-((5-fluoropyridin-2-yl)ethynyl)pyrimidin-4-yl)amino)ethyl)-8-fluoro-5-methyl-4-oxoquinazolin-3(4H)-yl)benzonitrile (Compound 72a): $^1$H NMR (400 MHz, DMSO) δ 8.60 (d, J=2.8 Hz, 1H), 8.15 (dd, J=2.1, 1.5 Hz, 1H), 8.00-7.78 (m, 6H), 7.72-7.55 (m, 2H), 7.34-7.25 (m, 2H), 4.93-4.87 (m, 1H), 2.64 (s, 3H), 1.41 (d, J=6.6 Hz, 3H). ES/MS 535.2 (M+H$^+$);

(S)-3-(2-(1-((6-amino-5-(pyrazin-2-ylethynyl)pyrimidin-4-yl)amino)ethyl)-8-fluoro-5-methyl-4-oxoquinazolin-3(4H)-yl)benzonitrile (Compound 73a): $^1$H NMR (400 MHz, DMSO) δ 8.96 (dd, J=2.9, 1.5 Hz, 1H), 8.66 (dd, J=2.6, 1.5 Hz, 1H), 8.58 (d, J=2.6 Hz, 1H), 8.15 (t, J=1.8 Hz, 1H), 7.98-7.77 (m, 4H), 7.73-7.54 (m, 2H), 7.40-7.20 (m, 2H), 4.95-4.86 (m, 1H), 2.64 (s, 3H), 1.41 (d, J=6.6 Hz, 3H). ES/MS 518.2 (M+H$^+$);

(S)-2-(1-((6-amino-5-(pyrazin-2-ylethynyl)pyrimidin-4-yl)amino)propyl)-5-(difluoromethyl)-3-(3,5-difluorophenyl)quinazolin-4(3H)-one (Compound 74a): $^1$H NMR (400 MHz, DMSO) δ 9.00 (d, J=1.6 Hz, 1H), 8.73 (dd, J=2.6, 1.5 Hz, 1H), 8.61 (d, J=2.5 Hz, 1H), 8.04 (s, 1H), 8.03-7.70 (m, 4H), 7.65-7.50 (m, 3H), 7.43 (tt, J=9.4, 2.5 Hz, 1H), 7.37-7.29 (m, 1H), 4.92-4.83 (m, 1H), 2.01 (ddd, J=14.2, 7.4, 4.8 Hz, 1H), 1.79 (dq, J=15.2, 7.5 Hz, 1H), 0.79 (t, J=7.3 Hz, 3H). ES/MS 561.2 (M+H$^+$);

(S)-2-(1-((6-amino-5-(pyrazin-2-ylethynyl)pyrimidin-4-yl)amino)ethyl)-8-fluoro-5-methyl-3-phenylquinazolin-4(3H)-one (Compound 75a): $^1$H NMR (400 MHz, DMSO) δ 8.95 (d, J=1.5 Hz, 1H), 8.68 (dd, J=2.6, 1.5 Hz, 1H), 8.61 (d, J=2.6 Hz, 1H), 8.03 (s, 1H), 7.64 (s, 1H), 7.59-7.38 (m, 7H), 7.27 (ddd, J=8.4, 5.0, 1.0 Hz, 1H), 4.91-4.82 (m, 1H), 2.64 (s, 3H), 1.38 (d, J=6.7 Hz, 3H). ES/MS 493.2 (M+H$^+$);

(S)-2-(1-((6-amino-5-(pyrazin-2-ylethynyl)pyrimidin-4-yl)amino)ethyl)-5-(difluoromethyl)-3-phenylquinazolin-4(3H)-one (Compound 76a): $^1$H NMR (400 MHz, DMSO) δ 9.02 (d, J=1.5 Hz, 1H), 8.77 (dd, J=2.6, 1.5 Hz, 1H), 8.63 (d, J=2.6 Hz, 1H), 8.09-7.72 (m, 6H), 7.61-7.44 (m, 6H), 4.91-4.83 (m, 1H), 1.36 (d, J=6.7 Hz, 3H). ES/MS 511.2 (M+H$^+$);

(S)-2-(1-((6-amino-5-((5-fluoropyridin-2-yl)ethynyl)pyrimidin-4-yl)amino)ethyl)-5-(difluoromethyl)-3-(3,5-difluorophenyl)quinazolin-4(3H)-one (Compound 77a): $^1$H NMR (400 MHz, DMSO) δ 8.68 (dt, J=3.0, 0.7 Hz, 1H), 8.09-7.71 (m, 8H), 7.62-7.52 (m, 2H), 7.46-7.29 (m, 3H), 5.01-4.92 (m, 1H), 1.41 (d, J=6.6 Hz, 3H). ES/MS 564.2 (M+H$^+$);

(S)-5-chloro-2-(1-((2,6-diamino-5-((5-fluoropyridin-2-yl)ethynyl)pyrimidin-4-yl)amino)ethyl)-3-(3,5-difluorophenyl)quinazolin-4(3H)-one (Compound 78a): $^1$H NMR (400 MHz, DMSO) δ 8.6 (m, 1H), 7.9-7.4 (m, 8H), 6.7 (m, 1H), 6.26 (bs, 1H), 5.98 (bs, 2H), 4.7 (m, 1H), 1.33 (d, J=4 Hz, 3H). ES/MS 563.9 (M+H$^+$);

(S)-2-(1-((6-amino-5-((3-fluoropyridin-2-yl)ethynyl)pyrimidin-4-yl)amino)ethyl)-5-chloro-3-(3,5-difluorophenyl)quinazolin-4(3H)-one. (Compound 79a): $^1$H NMR (400 MHz, DMSO) δ 8.54 (dt, J=4.7, 1.5 Hz, 1H), 8.08 (s, 1H), 7.90 (ddd, J=9.3, 8.5, 1.3 Hz, 1H), 7.76 (t, J=8 Hz, 1H), 7.65-7.4 (m, 8H), 4.85 (m, 1H), 1.36 (d, J=6.4 Hz, 3H). ES/MS 548.9 (M+H$^+$);

(S)-2-(1-((6-amino-5-((3-methoxypyridin-2-yl)ethynyl)pyrimidin-4-yl)amino)ethyl)-5-chloro-3-(3,5-difluorophenyl)quinazolin-4(3H)-one. (Compound 80a): $^1$H NMR (400 MHz, DMSO) δ 8.24 (dd, J=4.7, 1.3 Hz, 1H), 8.11 (s, 1H), 7.75 (dd, J=8.5, 7.6 Hz, 1H), 7.65-7.4 (m, 8H), 4.88 (m, 1H), 1.38 (d, J=6.7 Hz, 3H). ES/MS 560.9 (M+H$^+$);

(S)-2-(1-((6-amino-5-((3-fluoropyridin-2-yl)ethynyl)pyrimidin-4-yl)amino)ethyl)-5-chloro-3-(3-methoxy-2-methylphenyl)quinazolin-4(3H)-one (Compound 81a-1): $^1$H NMR (400 MHz, DMSO-d6) δ 8.50 (dt, J=4.6, 1.5 Hz, 1H), 7.91-7.5 (m, 9H), 7.29 (t, J=8.2 Hz, 1H), 7.07 (d, J=7.8 Hz, 1H), 6.99 (d, J=8.4 Hz, 1H), 5.17 (m, 1H), 3.78 (s, 3H), 1.86 (s, 3H), 1.42 (d, J=6.6 Hz, 3H). ES/MS 557.0 (M+H$^+$);

(S)-2-(1-((6-amino-5-((3-fluoropyridin-2-yl)ethynyl)pyrimidin-4-yl)amino)ethyl)-5-chloro-3-(3-methoxy-2-methylphenyl)quinazolin-4(3H)-one (Compound 81a-2): $^1$H NMR (400 MHz, DMSO-d$_6$) δ 8.55 (dt, J=4.7, 1.5 Hz, 1H), 8.09 (s, 1H), 7.91 (ddd, J=9.3, 8.5, 1.3 Hz, 1H), 7.83-7.4 (m, 6H), 7.28 (t, J=8.1 Hz, 1H), 7.06 (d, J=8.1 Hz, 2H), 4.96 (m, 1H), 3.85 (s, 3H), 1.89 (s, 3H), 1.26 (d, J=6.7 Hz, 3H). ES/MS 557.0 (M+H$^+$);

(S)-2-(1-((6-amino-5-((3,5-difluoropyridin-2-yl)ethynyl)pyrimidin-4-yl)amino)ethyl)-5-chloro-3-phenylquinazolin-4(3H)-one. (Compound 82a): $^1$H NMR (400 MHz, DMSO-d6) δ 8.65 (d, J=2.3 Hz, 1H), 8.16 (td, J=9.0, 2.4 Hz, 1H), 8.10 (s, 1H), 7.81-7.4 (m, 8H), 4.86 (p, J=6.7 Hz, 1H), 1.36 (d, J=6.7 Hz, 3H). ES/MS 530.9 (M+H$^+$)

(S)-5-chloro-2-(1-((2,6-diamino-5-((5-fluoropyridin-2-yl)ethynyl)pyrimidin-4-yl)amino)ethyl)-3-phenylquinazolin-4(3H)-one. (Compound 83a): $^1$H NMR (400 MHz, DMSO-d$_6$) δ 8.64 (dt, J=2.9, 0.7 Hz, 1H), 7.93-7.71 (m, 4H), 7.65-7.51 (m, 5H), 6.82 (d, J=7.0 Hz, 1H), 6.28 (bs, 1H), 5.98 (s, 1H), 4.68 (q, J=6.6 Hz, 1H), 1.23 (d, J=6.4 Hz, 3H). ES/MS 527.9 (M+H$^+$);

(S)-2-(1-((6-amino-5-((5-fluoropyridin-2-yl)ethynyl)pyrimidin-4-yl)amino)ethyl)-5-chloro-3-(3,5-difluorophenyl)-8-fluoroquinazolin-4(3H)-one (Compound 84a). $^1$H NMR (400 MHz, DMSO-d$_6$) δ 8.61 (dd, J=2.8, 0.9 Hz, 1H), 8.08 (s, 1H), 7.92-7.66 (m, 3H), 7.70-7.48 (m, 4H), 7.45-7.06 (m, 2H), 5.01 (p, J=6.8 Hz, 1H), 1.45 (d, J=6.6 Hz, 3H). ES/MS 566.5 (M+H$^+$);

(S)-2-(1-((6-amino-5-(pyrazin-2-ylethynyl)pyrimidin-4-yl)amino)ethyl)-5-chloro-3-(3,5-difluorophenyl)quinazolin-4(3H)-one (Compound 85a). $^1$H NMR (400 MHz, DMSO-d$_6$) δ 9.00 (d, J=1.5 Hz, 1H), 8.84-8.54 (m, 2H), 8.06 (s, 1H), 7.89-7.70 (m, 2H), 7.68-7.41 (m, 3H), 7.52-7.29 (m, 2H), 4.92 (t, J=6.7 Hz, 1H), 1.41 (d, J=6.6 Hz, 3H). ES/MS 531.6 (M+H$^+$);

(S)-2-(1-((6-amino-5-(pyrazin-2-ylethynyl)pyrimidin-4-yl)amino)ethyl)-5-fluoro-3-phenylquinazolin-4(3H)-one (Compound 86a). $^1$H NMR (400 MHz, DMSO-d$_6$) δ 9.02 (d, J=1.7 Hz, 1H), 8.88-8.76 (m, 1H), 8.70-8.56 (m, 1H), 8.10 (d, J=2.1 Hz, 1H), 8.03-7.78 (m, 2H), 7.78-7.46 (m, 7H), 7.45-7.11 (m, 2H), 5.01-4.76 (m, 1H), 1.35 (dd, J=6.6, 2.2 Hz, 3H). ES/MS 479.3 (M+H+);

(S)-2-(1-(((6-amino-5-(pyrazin-2-ylethynyl)pyrimidin-4-yl)amino)ethyl)-3-(3,5-difluorophenyl)-5-fluoroquinazolin-4(3H)-one (Compound 87a). $^1$H NMR (400 MHz, DMSO-$d_6$) δ 9.00 (t, J=1.1 Hz, 1H), 8.74 (ddd, J=2.4, 1.5, 0.8 Hz, 1H), 8.62 (dd, J=2.6, 0.7 Hz, 1H), 8.07 (s, 1H), 7.99-7.80 (m, 1H), 7.75 (s, 1H), 7.70-7.46 (m, 3H), 7.48-7.13 (m, 3H), 4.94 (t, J=6.8 Hz, 2H), 1.42 (d, J=6.6 Hz, 3H). ES/MS 515.6 (M+H+);

(R)-2-(1-(((6-amino-5-((5-fluoropyridin-2-yl)ethynyl)pyrimidin-4-yl)amino)ethyl)-5-chloro-3-(3,5-difluorophenyl)quinazolin-4(3H)-one (Compound 9b). $^1$H NMR (400 MHz, DMSO-$d_6$) δ 8.70 (d, J=2.8 Hz, 1H), 8.11 (s, 1H), 7.98-7.68 (m, 4H), 7.70-7.50 (m, 3H), 7.50-7.06 (m, 3H), 4.92 (t, J=6.8 Hz, 1H), 1.40 (dd, J=6.4, 1.3 Hz, 3H). ES/MS 548.8 (M+H+);

(S)-2-(1-(((6-amino-5-(pyrazin-2-ylethynyl)pyrimidin-4-yl)amino)ethyl)-5-chloro-3-(3-chlorophenyl)quinazolin-4(3H)-one (Compound 89a). $^1$H NMR (400 MHz, DMSO-$d_6$) δ 9.01 (dd, J=3.9, 1.4 Hz, 1H), 8.84-8.69 (m, 1H), 8.62 (q, J=2.5 Hz, 1H), 8.05 (d, J=19.0 Hz, 1H), 7.91-7.73 (m, 3H), 7.71-7.43 (m, 5H), 4.87 (q, J=6.2 Hz, 1H), 1.38 (t, J=6.5 Hz, 3H). ES/MS 530.4 (M+H+);

(S)-2-(1-(((6-amino-5-((5-fluoropyridin-2-yl)ethynyl)pyrimidin-4-yl)amino)ethyl)-6-fluoro-3-phenylquinazolin-4(3H)-one (Compound 90a). $^1$H NMR (400 MHz, DMSO-$d_6$) δ 8.75 (dt, J=2.9, 0.7 Hz, 1H), 8.06 (s, 1H), 8.01-7.73 (m, 6H), 7.68-7.36 (m, 6H), 4.85 (q, J=6.6 Hz, 1H), 1.33 (d, J=6.6 Hz, 3H). ES/MS 496.5 (M+H+);

(S)-2-(1-(((6-amino-5-(pyrazin-2-ylethynyl)pyrimidin-4-yl)amino)ethyl)-6-fluoro-3-phenylquinazolin-4(3H)-one (Compound 91a). $^1$H NMR (400 MHz, DMSO-$d_6$) δ 9.02 (d, J=1.5 Hz, 1H), 8.78 (dd, J=2.6, 1.5 Hz, 1H), 8.63 (d, J=2.6 Hz, 1H), 8.06 (s, 1H), 8.01-7.70 (m, 4H), 7.71-7.20 (m, 7H), 4.85 (p, J=6.4 Hz, 1H), 1.35 (d, J=6.6 Hz, 3H). ES/MS 479.5 (M+H$^+$);

(S)-3-(2-(1-(((6-amino-5-((5-fluoropyridin-2-yl)ethynyl)pyrimidin-4-yl)amino)ethyl)-5-chloro-4-oxoquinazolin-3(4H)-yl)benzonitrile (Compound 92a). $^1$H NMR (400 MHz, DMSO-$d_6$) δ 8.69 (tt, J=2.9, 0.7 Hz, 1H), 8.12-7.68 (m, 10H), 7.61 (dd, J=7.7, 1.3 Hz, 2H), 4.92-4.62 (m, 1H), 1.37 (dd, J=6.6, 1.9 Hz, 3H). ES/MS 537.5 (M+H+);

(S)-3-(2-(1-(((6-amino-5-(pyrazin-2-ylethynyl)pyrimidin-4-yl)amino)ethyl)-5-chloro-4-oxoquinazolin-3(4H)-yl)benzonitrile (Compound 93a). $^1$H NMR (400 MHz, DMSO-$d_6$) δ 9.01 (t, J=1.5 Hz, 1H), 8.73 (ddd, J=2.6, 2.0, 1.5 Hz, 1H), 8.61 (dd, J=2.6, 0.8 Hz, 1H), 8.19 (ddd, J=2.1, 1.6, 0.5 Hz, 1H), 8.06-7.68 (m, 9H), 7.66-7.57 (m, 1H), 5.02-4.74 (m, 1H), 1.38 (dd, J=6.6, 2.0 Hz, 3H). ES/MS 521.1 (M+H$^+$);

(S)-3-(2-(1-(((6-amino-5-((5-fluoropyridin-2-yl)ethynyl)pyrimidin-4-yl)amino)ethyl)-6-fluoro-4-oxoquinazolin-3(4H)-yl)benzonitrile (Compound 94a). $^1$H NMR (400 MHz, DMSO-$d_6$) δ 8.70 (tt, J=2.9, 0.7 Hz, 1H), 8.21 (td, J=1.8, 0.5 Hz, 1H), 8.16-7.64 (m, 10H), 7.50 (s, 1H), 4.87 (d, J=6.5 Hz, 1H), 1.53-1.32 (m, 3H). ES/MS 521.6 (M+H$^+$);

(S)-3-(2-(1-(((6-amino-5-(pyrazin-2-ylethynyl)pyrimidin-4-yl)amino)ethyl)-6-fluoro-4-oxoquinazolin-3(4H)-yl)benzonitrile (Compound 95a). $^1$H NMR (400 MHz, DMSO-$d_6$) δ 9.08-8.90 (m, 1H), 8.74 (dt, J=2.6, 1.7 Hz, 1H), 8.67-8.45 (m, 1H), 8.20 (ddd, J=2.1, 1.6, 0.5 Hz, 1H), 8.06-7.64 (m, 10H), 7.46 (s, 2H), 4.90 (q, J=6.4 Hz, 1H), 1.40 (dd, J=6.7, 0.9 Hz, 3H). ES/MS 504.4 (M+H+);

(S)-2-(1-(((6-amino-5-((5-fluoropyridin-2-yl)ethynyl)pyrimidin-4-yl)amino)ethyl)-3-(3-chlorophenyl)-6-fluoroquinazolin-4(3H)-one (Compound 96a). $^1$H NMR (400 MHz, DMSO-$d_6$) δ 8.71 (ddt, J=5.4, 2.9, 0.7 Hz, 1H), 8.06 (d, J=16.9 Hz, 1H), 8.01-7.75 (m, 6H), 7.66-7.38 (m, 6H), 4.92 (dd, J=8.3, 5.1 Hz, 1H), 1.38 (t, J=6.4 Hz, 3H). ES/MS 530.8 (M+H+);

(S)-2-(1-(((6-amino-5-(pyrazin-2-ylethynyl)pyrimidin-4-yl)amino)ethyl)-3-(3-chlorophenyl)-6-fluoroquinazolin-4(3H)-one (Compound 97a). $^1$H NMR (400 MHz, DMSO-$d_6$) δ 9.01 (dd, J=4.4, 1.6 Hz, 1H), 8.76 (ddd, J=4.1, 2.6, 1.6 Hz, 1H), 8.63 (t, J=2.3 Hz, 1H), 8.06 (d, J=19.3 Hz, 1H), 7.99-7.71 (m, 5H), 7.70-7.38 (m, 5H), 5.01-4.88 (m, 1H), 1.40 (dd, J=6.7, 5.5 Hz, 3H). ES/MS 513.9 (M+H+);

(S)-2-(1-(((6-amino-5-(pyrazin-2-ylethynyl)pyrimidin-4-yl)amino)ethyl)-5-methyl-3-phenylquinazolin-4(3H)-one (Compound 98a). $^1$H NMR (400 MHz, DMSO-$d_6$) δ 9.03 (d, J=1.5 Hz, 1H), 8.86-8.69 (m, 1H), 8.63 (dd, J=2.7, 1.5 Hz, 1H), 8.03 (d, J=2.3 Hz, 1H), 7.89-7.59 (m, 4H), 7.53 (dt, J=9.8, 3.6 Hz, 6H), 7.31 (d, J=7.2 Hz, 1H), 4.79 (t, J=6.9 Hz, 1H), 2.71 (s, 3H), 1.49-1.21 (m, 3H). ES/MS 475.3 (M+H+).

(S)-2-(1-(((6-amino-5-((5-fluoropyridin-2-yl)ethynyl)pyrimidin-4-yl)amino)ethyl)-5-fluoro-3-(3-fluorophenyl)quinazolin-4(3H)-one (Compound 99a). $^1$H NMR (400 MHz, DMSO-$d_6$) δ 8.71 (dt, J=2.9, 0.7 Hz, 1H), 8.07 (d, J=3.8 Hz, 1H), 8.01-7.80 (m, 2H), 7.85-7.63 (m, 2H), 7.66-7.15 (m, 6H), 5.02-4.73 (m, 1H), 1.37 (d, J=6.6 Hz, 3H). ES/MS 514.5 (M+H+).

(S)-2-(1-(((6-amino-5-(pyrazin-2-ylethynyl)pyrimidin-4-yl)amino)ethyl)-3-(3,5-difluorophenyl)-8-fluoroquinazolin-4(3H)-one (Compound 100a). $^1$H NMR (400 MHz, DMSO-$d_6$) δ 8.95 (d, J=1.5 Hz, 1H), 8.68 (dd, J=2.6, 1.5 Hz, 1H), 8.60 (d, J=2.5 Hz, 1H), 8.07 (s, 1H), 8.05-7.85 (m, 1H), 7.85-7.68 (m, 2H), 7.55 (ddt, J=15.8, 7.9, 3.6 Hz, 3H), 7.46-7.32 (m, 1H), 7.32-7.17 (m, 1H), 5.05 (t, J=6.9 Hz, 1H), 1.47 (d, J=6.6 Hz, 3H). ES/MS 515.3 (M+H$^+$).

(S)-2-(1-(((6-amino-5-(pyrazin-2-ylethynyl)pyrimidin-4-yl)amino)ethyl)-5-fluoro-3-(3-fluorophenyl)quinazolin-4(3H)-one (Compound 101a). $^1$H NMR (400 MHz, DMSO-$d_6$) δ 9.01 (t, J=1.5 Hz, 1H), 8.76 (ddd, J=2.4, 1.4, 0.6 Hz, 1H), 8.63 (d, J=2.6 Hz, 1H), 8.08 (d, J=5.1 Hz, 1H), 7.96-7.73 (m, 2H), 7.75-7.55 (m, 3H), 7.53-7.22 (m, 4H), 4.86 (dq, J=13.6, 6.8 Hz, 1H), 1.38 (d, J=6.6 Hz, 3H). ES/MS 497.5 (M+H+);

(S)-2-(1-(((6-amino-5-(pyrimidin-2-ylethynyl)pyrimidin-4-yl)amino)ethyl)-5-chloro-3-phenylquinazolin-4(3H)-one (Compound 102a). $^1$H NMR (400 MHz, DMSO-$d_6$) δ 9.02-8.84 (m, 1H), 8.07 (s, 1H), 7.92-7.75 (m, 2H), 7.73-7.48 (m, 7H), 7.45 (d, J=19.5 Hz, 2H), 4.80 (t, J=6.7 Hz, 1H), 1.32 (d, J=6.6 Hz, 3H). ES/MS 495.7 (M+H+).

(S)-2-(1-(((6-amino-5-(pyrimidin-2-ylethynyl)pyrimidin-4-yl)amino)ethyl)-5-chloro-3-(3,5-difluorophenyl)quinazolin-4(3H)-one (Compound 103a). $^1$H NMR (400 MHz, DMSO-$d_6$) δ 9.06-8.78 (m, 2H), 8.10 (s, 1H), 7.97-7.72 (m, 3H), 7.75-7.51 (m, 3H), 7.51-7.31 (m, 3H), 4.93 (t, J=6.7 Hz, 1H), 1.41 (d, J=6.6 Hz, 3H). ES/MS 531.8 (M+H+);

(S)-2-(1-(((6-amino-5-(pyrimidin-2-ylethynyl)pyrimidin-4-yl)amino)ethyl)-5-methyl-3-phenylquinazolin-4(3H)-one (Compound 104a). $^1$H NMR (400 MHz, DMSO-$d_6$) δ 9.02-8.83 (m, 2H), 8.09 (s, 1H), 7.92 (s, 1H), 7.82-7.66 (m, 2H), 7.61-7.46 (m, 6H), 7.31 (ddd, J=7.3, 1.4, 0.9 Hz, 1H), 4.81 (p, J=6.6 Hz, 1H), 2.84-2.62 (m, 3H), 1.32 (d, J=6.6 Hz, 3H). ES/MS 475.6 (M+H+);

(S)-2-(1-(((6-amino-5-(pyrimidin-2-ylethynyl)pyrimidin-4-yl)amino)ethyl)-3-(3,5-difluorophenyl)-5-methylquinazolin-4(3H)-one (Compound 105a). $^1$H NMR (400 MHz, DMSO-$d_6$) δ 8.92 (d, J=4.9 Hz, 2H), 8.13 (s, 1H), 7.90 (s, 1H), 7.84-7.65 (m, 2H), 7.65-7.52 (m, 3H), 7.49-7.27 (m, 4H), 5.07-4.89 (m, 1H), 2.72 (d, J=5.9 Hz, 3H), 1.51-1.28 (m, 3H). ES/MS 511.3 (M+H$^+$);

(S)-2-(1-(((6-amino-5-(pyrazin-2-ylethynyl)pyrimidin-4-yl)amino)ethyl)-3-(3-fluorophenyl)-5-methylquinazolin-4

(3H)-one (Compound 106a). ¹H NMR (400 MHz, DMSO-d₆) δ 9.04 (t, J=1.4 Hz, 1H), 8.78 (ddd, J=2.5, 1.5, 0.8 Hz, 1H), 8.69-8.57 (m, 1H), 8.23-8.07 (m, 1H), 7.95 (s, 1H), 7.82-7.52 (m, 4H), 7.51-7.08 (m, 4H), 4.88 (tt, J=12.6, 6.6 Hz, 1H), 2.72 (d, J=6.2 Hz, 3H), 1.60-1.20 (m, 3H). ES/MS 493.5 (M+H+);

(S)-2-(1-((6-amino-5-(pyrazin-2-ylethynyl)pyrimidin-4-yl)amino)propyl)-3-(3,5-difluorophenyl)-5-fluoroquinazolin-4(3H)-one (Compound 107a). ¹H NMR (400 MHz, DMSO-d₆) δ 9.02 (d, J=1.5 Hz, 1H), 8.76 (dd, J=2.6, 1.5 Hz, 1H), 8.69-8.53 (m, 1H), 8.06 (d, J=5.8 Hz, 1H), 7.98-7.80 (m, 1H), 7.70-7.29 (m, 8H), 4.86 (q, J=7.2 Hz, 1H), 2.15-1.92 (m, 1H), 1.79 (dt, J=14.5, 7.5 Hz, 1H), 0.80 (t, J=7.3 Hz, 3H). ES/MS 529.6 (M+H⁺);

(S)-2-(1-((6-amino-5-(pyrazin-2-ylethynyl)pyrimidin-4-yl)amino)propyl)-3-(3,5-difluorophenyl)-5-methylquinazolin-4(3H)-one (Compound 108a). ¹H NMR (400 MHz, DMSO-d₆) δ 9.03 (d, J=1.4 Hz, 1H), 8.86-8.69 (m, 1H), 8.76-8.58 (m, 1H), 8.15 (d, J=6.2 Hz, 1H), 7.93-7.70 (m, 3H), 7.66-7.51 (m, 2H), 7.49-7.24 (m, 3H), 4.88 (d, J=5.5 Hz, 1H), 2.72 (d, J=5.2 Hz, 3H), 2.09-1.92 (m, 1H), 1.80 (dt, J=14.7, 7.4 Hz, 1H), 0.80 (t, J=7.4 Hz, 3H). ES/MS 525.5 (M+H+);

(S)-2-(1-((6-amino-5-(pyrimidin-2-ylethynyl)pyrimidin-4-yl)amino)propyl)-5-fluoro-3-phenylquinazolin-4(3H)-one (Compound 109a). ¹H NMR (400 MHz, DMSO-d₆) δ 9.04-8.86 (m, 2H), 8.01 (d, J=60.1 Hz, 1H), 7.98-7.72 (m, 2H), 7.77-7.63 (m, 1H), 7.66-7.49 (m, 4H), 7.43-7.22 (m, 3H), 4.83 (p, J=6.6 Hz, 1H), 1.35 (d, J=6.6 Hz, 3H). ES/MS 479.5 (M+H⁺);

(S)-3-(2-(1-((6-amino-5-(phenylethynyl)pyrimidin-4-yl)amino)ethyl)-5-fluoro-4-oxoquinazolin-3(4H)-yl)benzonitrile (Compound 110a). ¹H NMR (400 MHz, DMSO-d₆) δ 8.09 (d, J=13.2 Hz, 1H), 8.04-7.78 (m, 4H), 7.81-7.63 (m, 3H), 7.68-7.17 (m, 8H), 4.86 (dd, J=9.8, 5.0 Hz, 1H), 1.44 (d, J=6.6 Hz, 3H). ES/MS 502.4 (M+H+);

(S)-2-(1-((6-amino-5-(phenylethynyl)pyrimidin-4-yl)amino)ethyl)-5-fluoro-3-(3-fluorophenyl)quinazolin-4(3H)-one (Compound 111a). ¹H NMR (400 MHz, DMSO-d₆) δ 8.11 (dd, J=5.4, 2.0 Hz, 1H), 7.99-7.68 (m, 5H), 7.68-7.53 (m, 3H), 7.53-7.17 (m, 7H), 4.87 (q, J=7.6 Hz, 1H), 1.43 (dd, J=6.7, 2.0 Hz, 3H). ES/MS 435.6 (M+H+);

(S)-2-(1-((6-amino-5-(phenylethynyl)pyrimidin-4-yl)amino)ethyl)-5-(methylsulfonyl)-3-phenylquinazolin-4(3H)-one (Compound 112a). ¹H NMR (400 MHz, DMSO-d₆) δ 8.27 (dd, J=7.7, 1.3 Hz, 1H), 8.16-7.99 (m, 2H), 7.93 (dd, J=8.2, 1.3 Hz, 1H), 7.82-7.66 (m, 2H), 7.66-7.20 (m, 9H), 4.95-4.73 (m, 1H), 3.46 (s, 3H), 1.41 (d, J=6.8 Hz, 3H). ES/MS 536.3 (M+H+);

(S)-2-(1-((6-amino-5-(pyrazin-2-ylethynyl)pyrimidin-4-yl)amino)ethyl)-5-(methylsulfonyl)-3-phenylquinazolin-4(3H)-one (Compound 113a). ¹H NMR (400 MHz, DMSO-d₆) δ 9.11-8.91 (m, 1H), 8.76 (ddd, J=2.5, 1.6, 0.7 Hz, 1H), 8.72-8.52 (m, 1H), 8.42-8.21 (m, 1H), 8.24-7.96 (m, 3H), 7.75-7.22 (m, 7H), 4.83 (t, J=6.7 Hz, 1H), 3.63 (s, 3H), 1.35 (d, J=6.7 Hz, 3H). ES/MS 539.3 (M+H⁺).

(S)-2-(1-((6-amino-5-(phenylethynyl)pyrimidin-4-yl)amino)ethyl)-4-oxo-3-phenyl-3,4-dihydroquinazoline-5-carbonitrile (Compound 114a). ¹H NMR (400 MHz, DMSO-d₆) δ 8.16-8.01 (m, 1H), 8.01-7.80 (m, 3H), 7.82-7.64 (m, 3H), 7.68-7.29 (m, 10H), 4.94-4.71 (m, 1H), 1.39 (d, J=6.7 Hz, 3H). ES/MS 484.6 (M+H+);

(S)-2-(1-((6-amino-5-(pyrazin-2-ylethynyl)pyrimidin-4-yl)amino)ethyl)-5-fluoro-3-(pyridin-3-yl)quinazolin-4(3H)-one (Compound 115a). ¹H NMR (400 MHz, DMSO-d₆) δ 9.00 (d, J=1.5 Hz, 1H), 8.83-8.47 (m, 3H), 8.19-7.96 (m, 2H), 7.88 (td, J=8.2, 5.4 Hz, 2H), 7.70-7.39 (m, 3H), 7.46-7.22 (m, 2H), 4.76 (dt, J=20.3, 6.8 Hz, 1H), 1.36 (t, J=6.7 Hz, 3H). ES/MS 480.2 (M+H+);

(S)-2-(1-((6-amino-5-(phenylethynyl)pyrimidin-4-yl)amino)ethyl)-5-fluoro-3-(pyridin-3-yl)quinazolin-4(3H)-one (Compound 116a). ¹H NMR (400 MHz, DMSO-d₆) δ 8.88-8.74 (m, 1H), 8.76-8.49 (m, 2H), 8.17-7.99 (m, 2H), 8.06-7.78 (m, 2H), 7.84-7.48 (m, 4H), 7.50-7.18 (m, 4H), 4.80 (q, J=6.8 Hz, 1H), 1.58-1.37 (m, 3H). ES/MS 478.4 (M+H⁺).

(S)-2-(1-((6-amino-5-(pyrimidin-2-ylethynyl)pyrimidin-4-yl)amino)ethyl)-5-chloro-3-(pyridin-3-yl)quinazolin-4(3H)-one (Compound 117a). ¹H NMR (400 MHz, DMSO-d₆) δ 8.95-8.56 (m, 3H), 8.17-7.92 (m, 1H), 7.91-7.31 (m, 6H), 7.27-6.88 (m, 3H), 5.02-4.67 (m, 1H), 1.54-1.17 (m, 3H). ES/MS 497.1 (M+H+);

(S)-2-(1-((6-amino-5-(pyrazin-2-ylethynyl)pyrimidin-4-yl)amino)ethyl)-5-chloro-3-(pyridin-3-yl)quinazolin-4(3H)-one (Compound 118a). ¹H NMR (400 MHz, DMSO-d₆) δ 9.00 (d, J=1.5 Hz, 1H), 8.91-8.45 (m, 4H), 8.14-7.91 (m, 2H), 7.87-7.64 (m, 2H), 7.68-7.36 (m, 4H), 4.88-4.65 (m, 1H), 1.36 (t, J=7.1 Hz, 3H). ES/MS 496.8 (M+H+);

(S)-2-(1-((6-amino-5-(pyrazin-2-ylethynyl)pyrimidin-4-yl)amino)ethyl)-5-methyl-3-(pyridin-3-yl)quinazolin-4(3H)-one (Compound 119a). ¹H NMR (400 MHz, DMSO-d₆) δ 9.00 (q, J=1.5 Hz, 1H), 8.95-8.37 (m, 4H), 8.02 (dddt, J=25.3, 8.1, 2.7, 1.4 Hz, 1H), 7.94-7.80 (m, 1H), 7.78-7.39 (m, 3H), 7.45-7.15 (m, 2H), 6.94 (s, 2H), 4.81-4.51 (m, 1H), 2.69 (s, 3H), 1.31 (ddd, J=8.1, 6.4, 1.2 Hz, 3H). ES/MS 476.6 (M+H⁺);

(S)-2-(1-((6-amino-5-(pyrazin-2-ylethynyl)pyrimidin-4-yl)amino)ethyl)-3-(5-fluoropyridin-3-yl)-5-methylquinazolin-4(3H)-one (Compound 120a). ¹H NMR (400 MHz, DMSO-d₆) δ 9.16-8.83 (m, 1H), 8.83-8.44 (m, 4H), 8.28-7.89 (m, 1H), 7.82 (dd, J=4.7, 1.7 Hz, 1H), 7.80-7.46 (m, 2H), 7.31 (dt, J=7.5, 1.3 Hz, 1H), 7.20-7.04 (m, 1H), 6.90 (s, 2H), 4.83 (dddd, J=15.4, 13.3, 7.4, 5.6 Hz, 1H), 2.69 (d, J=1.8 Hz, 3H), 1.36 (dd, J=7.1, 5.4 Hz, 3H). ES/MS 494.5 (M+H+);

(S)-2-(1-((6-amino-5-((5-fluoropyridin-2-yl)ethynyl)pyrimidin-4-yl)amino)ethyl)-5-chloro-3-morpholinoquinazolin-4(3H)-one (Compound 121a): ¹H NMR (400 MHz, DMSO) δ 8.71 (d, J=2.9 Hz, 1H), 8.18 (s, 1H), 7.97-7.73 (m, 5H), 7.53 (dt, J=7.3, 1.3 Hz, 1H), 5.63 (p, J=6.7 Hz, 1H), 4.03 (td, J=11.4, 3.1 Hz, 1H), 3.94-3.79 (m, 3H), 3.56 (dd, J=12.4, 10.0 Hz, 1H), 3.49-3.38 (m, 1H), 3.09 (d, J=10.7 Hz, 1H), 2.99 (dd, J=10.7, 2.4 Hz, 1H), 1.53 (d, J=6.6 Hz, 3H). ES/MS 521.2 (M+H⁺);

(S)-2-(1-((6-amino-5-((3-fluoro-5-methoxyphenyl)ethynyl)pyrimidin-4-yl)amino)ethyl)-5-chloro-3-morpholinoquinazolin-4(3H)-one (Compound 122a): ¹H NMR (400 MHz, DMSO) δ 8.14 (s, 1H), 7.83 (s, 1H), 7.67 (t, J=8.2 Hz, 1H), 7.55-7.43 (m, 4H), 7.24-7.16 (m, 2H), 6.90 (dt, J=11.2, 2.5 Hz, 1H), 5.73 (p, J=6.8 Hz, 1H), 4.06-3.76 (m, 5H), 3.55 (t, J=10.8 Hz, 1H), 3.48-3.37 (m, 1H), 3.12 (d, J=10.5 Hz, 1H), 2.98 (d, J=10.9 Hz, 1H), 2.51 (s, 1H), 2.46 (s, 4H), 1.56 (d, J=6.7 Hz, 3H). ES/MS 550.2 (M+H+);

S)—N-(3-(2-(1-((6-amino-5-(pyrazin-2-ylethynyl)pyrimidin-4-yl)amino)ethyl)-5-chloro-4-oxoquinazolin-3(4H)-yl)benzyl)methanesulfonamide (Compound 123a): ¹H NMR (400 MHz, DMSO) δ 9.01 (dd, J=2.6, 1.5 Hz, 1H), 8.75 (ddt, J=9.9, 2.5, 1.1 Hz, 1H), 8.66-8.58 (m, 1H), 8.02 (d, J=5.5 Hz, 1H), 7.86-7.40 (m, 10H), 4.83-4.70 (m, 1H), 4.20 (dd, J=20.5, 6.4 Hz, 2H), 2.84 (d, J=30.7 Hz, 3H), 1.38-1.29 (m, 3H). ES/MS 602.2 (M+H⁺);

2-((S)-1-((6-amino-5-(pyrazin-2-ylethynyl)pyrimidin-4-yl)amino)ethyl)-5-chloro-3-((1R,5S)-8-methyl-8-azabicyclo[3.2.1]octan-3-yl)quinazolin-4(3H)-one (Compound 124a): ¹H NMR (400 MHz, DMSO) δ 9.67 (d, J=5.7 Hz, 1H), 9.05 (d, J=1.5 Hz, 1H), 8.81 (dd, J=2.6, 1.5 Hz, 1H), 8.61 (d, J=2.6 Hz, 1H), 8.08 (s, 1H), 7.90 (dd, J=8.2, 1.3 Hz, 1H), 7.82 (t, J=8.0 Hz, 2H), 7.56 (dd, J=7.7, 1.3 Hz, 1H), 7.28 (s, 2H), 5.34 (p, J=6.4 Hz, 1H), 4.78 (p, J=9.7 Hz, 1H), 3.98-3.89 (m, 2H), 2.74-2.60 (m, 4H), 2.47 (dt, J=3.7, 1.9 Hz, 12H), 2.42-2.29 (m, 4H), 2.28-2.08 (m, 3H), 1.52 (d, J=6.4 Hz, 3H). ES/MS 542.2 (M+H+);

2-((S)-1-((6-amino-5-(pyrazin-2-ylethynyl)pyrimidin-4-yl)amino)ethyl)-5-chloro-3-((1R,5S)-8-methyl-8-azabicyclo[3.2.1]octan-3-yl)quinazolin-4(3H)-one (Compound 125a): $^1$H NMR (400 MHz, DMSO) δ 9.77-9.54 (m, 1H), 9.05 (dd, J=4.6, 1.6 Hz, 1H), 8.88-8.75 (m, 1H), 8.62 (dd, J=4.6, 2.5 Hz, 1H), 8.08 (d, J=4.6 Hz, 1H), 7.91 (dd, J=7.7, 4.3 Hz, 1H), 7.82 (ddd, J=9.1, 6.8, 3.9 Hz, 2H), 7.63-7.45 (m, 1H), 7.26 (s, 2H), 5.35 (q, J=6.2 Hz, 1H), 4.86-4.65 (m, 2H), 3.93 (d, J=8.3 Hz, 3H), 2.77-2.57 (m, 4H), 2.34 (d, J=5.3 Hz, 1H), 2.14 (d, J=5.4 Hz, 1H), 1.52 (dd, J=6.5, 4.4 Hz, 3H), 1.21 (s, 1H). ES/MS 542.2 (M+H+);

(S)-2-(1-((6-amino-5-(pyrazin-2-ylethynyl)pyrimidin-4-yl)amino)ethyl)-3-(azepan-1-yl)-5-chloroquinazolin-4(3H)-one (Compound 126a): $^1$H NMR (400 MHz, DMSO) δ 9.03 (d, J=1.5 Hz, 1H), 8.77 (ddd, J=2.5, 1.6, 0.6 Hz, 1H), 8.62 (d, J=2.6 Hz, 1H), 8.17 (s, 1H), 7.83-7.66 (m, 3H), 7.57 (s, 3H), 7.54-7.44 (m, 1H), 5.79 (p, J=6.6 Hz, 1H), 3.77 (td, J=8.0, 4.4 Hz, 1H), 3.62 (ddd, J=12.2, 8.9, 2.8 Hz, 1H), 3.17 (ddd, J=40.9, 12.6, 5.9 Hz, 3H), 1.78-1.45 (m, 15H). ES/MS 516.2 (M+H+);

(S)-2-(1-((6-amino-5-((5-fluoropyridin-2-yl)ethynyl)pyrimidin-4-yl)amino)ethyl)-5-chloro-3-(piperazin-1-yl)quinazolin-4(3H)-one (Compound 127a): $^1$H NMR (400 MHz, DMSO) δ 8.84 (d, J=11.4 Hz, 1H), 8.61 (d, J=14.8 Hz, 1H), 8.13-8.04 (m, 1H), 7.97-7.73 (m, 3H), 7.64-7.48 (m, 2H), 7.37 (s, 2H), 7.28 (s, 1H), 5.64-5.56 (m, 1H), 4.17 (t, J=12.6 Hz, 1H), 4.04 (t, J=12.7 Hz, 1H), 3.46-3.25 (m, 4H), 3.14 (t, J=13.8 Hz, 1H), 2.97 (d, J=12.2 Hz, 1H), 2.47 (d, J=10.1 Hz, 1H), 2.38 (s, 1H), 1.55-1.43 (m, 3H). ES/MS 520.2 (M+H$^+$);

(S)—N-(3-(2-(1-((6-amino-5-((5-fluoropyridin-2-yl)ethynyl)pyrimidin-4-yl)amino)ethyl)-5-methyl-4-oxoquinazolin-3(4H)-yl)benzyl)-N-methylmethanesulfonamide (Compound 128a): $^1$H NMR (400 MHz, DMSO) δ 8.70 (dd, J=5.8, 2.9 Hz, 1H), 8.02 (d, J=9.6 Hz, 1H), 7.97-7.40 (m, 9H), 7.30 (dd, J=7.5, 4.1 Hz, 1H), 4.79 (td, J=7.0, 4.0 Hz, 1H), 4.35-4.19 (m, 2H), 2.94 (d, J=16.5 Hz, 3H), 2.73-2.62 (m, 6H), 1.31 (d, J=6.6 Hz, 3H). ES/MS 613.2 (M+H+);

(S)—N-(3-(2-(1-((6-amino-5-((5-fluoropyridin-2-yl)ethynyl)pyrimidin-4-yl)amino)ethyl)-5-chloro-4-oxoquinazolin-3(4H)-yl)benzyl)-N-methylmethanesulfonamide (Compound 129a): $^1$H NMR (400 MHz, DMSO) δ 8.74-8.67 (m, 1H), 8.01 (d, J=9.0 Hz, 1H), 7.97-7.69 (m, 5H), 7.61-7.40 (m, 6H), 4.79 (q, J=6.7, 6.2 Hz, 1H), 4.34-4.20 (m, 2H), 3.33 (s, 6H), 2.94 (d, J=17.3 Hz, 3H), 2.70 (s, 2H), 2.64 (s, 2H), 1.31 (dd, J=6.8, 2.2 Hz, 3H). ES/MS 633.2 (M+H$^+$);

(S)—N-(3-(2-(1-((6-amino-5-((5-fluoropyridin-2-yl)ethynyl)pyrimidin-4-yl)amino)ethyl)-5-chloro-4-oxoquinazolin-3(4H)-yl)benzyl)methanesulfonamide (Compound 130a): $^1$H NMR (400 MHz, DMSO) δ 8.71 (dd, J=11.2, 2.9 Hz, 1H), 8.05 (d, J=3.1 Hz, 1H), 7.97-7.61 (m, 7H), 7.61-7.39 (m, 7H), 7.33 (s, 3H), 4.84-4.72 (m, 1H), 4.21 (dd, J=19.7, 6.4 Hz, 2H), 2.84 (d, J=30.6 Hz, 3H), 1.33 (dd, J=8.5, 6.5 Hz, 3H), 1.20 (dt, J=12.5, 6.7 Hz, 1H). ES/MS 619.2 (M+H+);

(S)—N-(3-(2-(1-((6-amino-5-((5-fluoropyridin-2-yl)ethynyl)pyrimidin-4-yl)amino)ethyl)-5-chloro-4-oxoquinazolin-3(4H)-yl)benzyl)-2-methylpropane-1-sulfonamide (Compound 131a): $^1$H NMR (400 MHz, DMSO) δ 8.70 (dd, J=16.9, 2.9 Hz, 1H), 8.03 (d, J=10.0 Hz, 1H), 7.97-7.66 (m, 5H), 7.63-7.35 (m, 7H), 4.77 (dt, J=13.3, 6.7 Hz, 1H), 4.19 (dd, J=20.8, 6.4 Hz, 2H), 2.89-2.67 (m, 2H), 2.01 (dh, J=27.2, 6.8 Hz, 1H), 1.33 (dd, J=12.5, 6.7 Hz, 3H), 1.01-0.85 (m, 7H). ES/MS 661.2 (M+H+);

(S)-2-(1-((6-amino-5-((5-(trifluoromethyl)pyridin-2-yl)ethynyl)pyrimidin-4-yl)amino)ethyl)-5-chloro-3-phenylquinazolin-4(3H)-one (Compound 132a): $^1$H NMR (400 MHz, DMSO-d$_6$) δ 9.09-9.03 (m, 1H), 8.32 (dd, J=8.3, 2.4 Hz, 1H), 8.09 (d, J=8.4 Hz, 1H), 8.00 (s, 1H), 7.90-7.82 (m, 2H), 7.67-7.42 (m, 6H), 7.36 (s, 2H), 4.78 (t, J=6.7 Hz, 1H), 1.32 (d, J=6.6 Hz, 3H). ES/MS 562.1 (M+H$^+$);

(S)-2-(1-((6-amino-5-((5-methylpyridin-2-yl)ethynyl)pyrimidin-4-yl)amino)ethyl)-5-chloro-3-phenylquinazolin-4(3H)-one (Compound 133a): $^1$H NMR (400 MHz, DMSO-d$_6$) δ 8.54 (d, J=1.8 Hz, 1H), 7.91-7.79 (m, 3H), 7.76-7.64 (m, 2H), 7.63-7.49 (m, 5H), 7.16 (d, J=7.0 Hz, 1H), 6.82 (s, 2H), 4.72 (t, J=6.7 Hz, 1H), 2.35 (s, 3H), 1.29 (d, J=6.6 Hz, 3H).). ES/MS 508.1 (M+H$^+$);

(S)-2-(1-((6-amino-5-((5-(trifluoromethyl)pyridin-2-yl)ethynyl)pyrimidin-4-yl)amino)ethyl)-5-chloro-3-(3,5-difluorophenyl)quinazolin-4(3H)-one (Compound 134a): $^1$H NMR (400 MHz, DMSO-d$_6$) δ 9.03 (s, 1H), 8.33-8.25 (m, 1H), 8.11-8.04 (m, 1H), 7.99 (s, 1H), 7.91-7.76 (m, 2H), 7.60 (dt, J=7.7, 1.3 Hz, 1H), 7.57-7.23 (m, 4H), 4.96-4.80 (m, 1H), 4.23-3.43 (brs, 2H), 1.39 (dd, J=6.8, 1.2 Hz, 4H). ES/MS 598.1 (M+H$^+$).

(S)-6-((4-amino-6-((1-(5-chloro-4-oxo-3-phenyl-3,4-dihydroquinazolin-2-yl)ethyl)amino)pyrimidin-5-yl)ethynyl)nicotinamide (Compound 135a): $^1$H NMR (400 MHz, DMSO-d$_6$) δ 9.12-9.06 (m, 1H), 8.31-8.20 (m, 2H), 8.05 (s, 1H), 7.96-7.89 (m, 1H), 7.90-7.80 (m, 2H), 7.69 (s, 1H), 7.61 (ddd, J=5.7, 3.3, 0.7 Hz, 1H), 7.54 (d, J=8.9 Hz, 1H), 7.47-7.33 (m, 3H), 4.90 (t, J=6.8 Hz, 1H), 4.12 (brs, 5H), 1.40 (d, J=6.6 Hz, 3H). ES/MS 537.1 (M+H+);

(S)-6-((4-amino-6-((1-(5-chloro-3-(3,5-difluorophenyl)-4-oxo-3,4-dihydroquinazolin-2-yl)ethyl)amino)pyrimidin-5-yl)ethynyl)nicotinamide (Compound 136a): $^1$H NMR (400 MHz, DMSO-d$_6$) δ 9.12 (d, J=2.2 Hz, 1H), 8.33-8.21 (m, 2H), 8.03 (s, 1H), 7.99-7.79 (m, 3H), 7.70 (s, 1H), 7.63-7.49 (m, 6H), 4.86-4.69 (m, 1H), 4.37-3.20 (br m, 2H), 1.32 (dd, J=6.9, 1.3 Hz, 3H). ES/MS 573.1 (M+H$^+$).

(S)-isopropyl 6-((4-amino-6-((1-(5-chloro-4-oxo-3-phenyl-3,4-dihydroquinazolin-2-yl)ethyl)amino)pyrimidin-5-yl)ethynyl)nicotinate (Compound 137a): $^1$H NMR (400 MHz, DMSO-d$_6$) δ 9.13 (d, J=5.1 Hz, 1H), 8.33 (dd, J=7.9, 5.1 Hz, 1H), 8.00 (t, J=6.7 Hz, 2H), 7.83 (dd, J=13.8, 6.4 Hz, 2H), 7.67-7.05 (m, 6H), 5.25-5.08 (m, 1H), 4.78 (dd, J=13.5, 6.2 Hz, 1H), 4.13-3.35 (m, 4H), 2.35 (d, J=28.1 Hz, 6H), 1.42-1.21 (m, 3H). ES/MS 580.1 (M+H+).

(S)-6-((4-amino-6-((1-(5-chloro-4-oxo-3-phenyl-3,4-dihydroquinazolin-2-yl)ethyl)amino)pyrimidin-5-yl)ethynyl)nicotinic acid (Compound 138a): $^1$H NMR (400 MHz, DMSO-d$_6$) δ 9.19-9.04 (m, 1H), 8.32 (dd, J=8.2, 2.3 Hz, 1H), 7.98 (d, J=8.1 Hz, 2H), 7.89-7.73 (m, 2H), 7.61-7.45 (m, 7H), 4.77 (s, 1H), 3.55 (brs, 4H), 1.38-1.27 (m, 3H). ES/MS 538.1 (M+H$^+$);

(R)-2-(1-((6-amino-5-((5-fluoropyridin-2-yl)ethynyl)pyrimidin-4-yl)amino)-2-hydroxyethyl)-5-chloro-3-phenylquinazolin-4(3H)-one (Compound 139a): $^1$H NMR (400 MHz, DMSO-d$_6$) δ 8.75 (d, J=2.9 Hz, 1H), 8.03 (s, 1H), 8.01-7.93 (m, 1H), 7.93-7.80 (m, 3H), 7.68-7.25 (m, 12H), 4.87 (q, J=5.2 Hz, 1H), 4.02-3.43 (m, 2H). ES/MS 528.1 (M+H+);

(S)-2-(1-((6-amino-5-((5-fluoro-6-methylpyridin-2-yl)ethynyl)pyrimidin-4-yl)amino)ethyl)-5-chloro-3-phenylquinazolin-4(3H)-one (Compound 140a): $^1$H NMR (400 MHz, DMSO-d$_6$) δ 10.36 (d, J=2.7 Hz, 1H), 9.22 (s, 1H), 8.49 (s, 1H), 7.98 (d, J=2.8 Hz, 1H), 7.71-7.39 (m, 6H), 7.30 (m, 4H), 7.07 (td, J=7.3, 2.5 Hz, 1H), 4.38 (d, J=6.9 Hz, 1H), 1.56-1.05 (m, 6H). ES/MS 526.1 (M+H⁺);

(S)-2-(1-((6-amino-5-((6-methylpyridin-2-yl)ethynyl)pyrimidin-4-yl)amino)ethyl)-5-chloro-3-phenylquinazolin-4(3H)-one (Compound 141a): ¹H NMR (400 MHz, DMSO-d₆) δ 8.02 (s, 1H), 7.86-7.67 (m, 3H), 7.67-7.46 (m, 7H), 7.33 (d, J=7.6 Hz, 1H), 4.78 (m, 1H), 3.52 (s, 7H), 1.33 (dd, J=6.5, 1.9 Hz, 3H). ES/MS 508.1 (M+H+);

(S)-2-(1-((6-amino-5-((3-(trifluoromethyl)pyridin-2-yl)ethynyl)pyrimidin-4-yl)amino)ethyl)-5-chloro-3-phenylquinazolin-4(3H)-one (Compound 142a): ¹H NMR (400 MHz, DMSO-d₆) δ 8.94 (dt, J=5.2, 0.8 Hz, 1H), 8.33-8.24 (m, 1H), 8.01 (s, 1H), 7.77 (t, J=8.0 Hz, 1H), 7.69-7.40 (m, 9H), 7.12 (m, 1H), 4.84 (t, J=6.7 Hz, 1H), 4.31-3.56 (m, 2H), 1.33 (dd, J=6.7, 0.9 Hz, 3H). ES/MS 562.1 (M+H⁺);

(S)-2-(1-((6-amino-5-((3-methylpyridin-2-yl)ethynyl)pyrimidin-4-yl)amino)ethyl)-5-chloro-3-phenylquinazolin-4(3H)-one (Compound 143a) ¹H NMR (400 MHz, DMSO-d₆) δ 8.58-8.49 (m, 1H), 8.04 (s, 1H), 7.85-7.80 (m, 1H), 7.80-7.73 (m, 1H), 7.64 (dd, J=8.2, 1.2 Hz, 1H), 7.60-7.46 (m, 7H), 7.39 (dd, J=7.8, 4.9 Hz, 1H), 4.91-4.75 (m, 1H), 3.69 (s, 3H), 2.54-2.49 (m, 3H), 1.34 (d, J=6.6 Hz, 3H). ES/MS 508.1 (M+H+).

(S)-2-(1-((6-amino-5-(cyclopentylethynyl)pyrimidin-4-yl)amino)ethyl)-5-chloro-3-phenylquinazolin-4(3H)-one (Compound 144a): ¹H NMR (400 MHz, DMSO-d₆) δ 8.04 (d, J=3.3 Hz, 1H), 7.81 (dd, J=8.3, 7.7 Hz, 1H), 7.60 (p, J=1.2 Hz, 1H), 7.58-7.55 (m, 2H), 7.52 (td, J=3.3, 1.9 Hz, 3H), 7.24 (brs, 2H), 4.79 (t, J=6.7 Hz, 1H), 3.55 (d, J=41.9 Hz, 3H), 3.02 (p, J=7.7 Hz, 1H), 2.03 (t, J=8.4 Hz, 2H), 1.85-1.69 (m, 4H), 1.62 (m, 2H), 1.31 (d, J=6.6 Hz, 3H). ES/MS 485.2 (M+H⁺);

(S)-2-(1-((6-amino-5-(cyclohexylethynyl)pyrimidin-4-yl)amino)ethyl)-5-chloro-3-phenylquinazolin-4(3H)-one (Compound 145a): ¹H NMR (400 MHz, DMSO-d₆) δ 8.05 (d, J=3.6 Hz, 1H), 7.80 (dd, J=8.3, 7.7 Hz, 1H), 7.62-7.46 (m, 9H), 7.18 (brs, 2H), 4.87-4.72 (m, 1H), 2.75 (d, J=9.8 Hz, 1H), 1.93 (m, 2H), 1.72 (d, J=6.9 Hz, 2H), 1.57 (m, 4H), 1.44-1.27 (m, 5H). ES/MS 499.2 (M+H+);

(R)-2-(1-((6-amino-5-((5-fluoropyridin-2-yl)ethynyl)pyrimidin-4-yl)amino)-2-methoxyethyl)-5-chloro-3-(3,5-difluorophenyl)quinazolin-4(3H)-one (Compound 146a): ¹H NMR (400 MHz, DMSO-d₆) δ 8.03 (t, J=2.9 Hz, 1H), 7.52-7.48 (m, 1H), 7.41-7.15 (m, 5H), 7.09 (ddt, J=8.2, 2.6, 1.2 Hz, 1H), 6.96 (dd, J=7.8, 2.6, 1.2 Hz, 1H), 6.89-6.82 (m, 1H), 6.76 (ddd, J=11.7, 8.7, 2.6 Hz, 1H), 6.70-6.59 (m, 1H), 5.62-4.73 (brs, 2H), 4.54 (td, J=6.7, 5.4, 3.1 Hz, 1H), 3.17 (m, 1H), 3.11-3.01 (m, 1H), 1.83 (dt, J=3.7, 1.8 Hz, 3H). ES/MS 578.1 (M+H⁺);

(S)-2-(1-((6-amino-5-((4-methylpyridin-2-yl)ethynyl)pyrimidin-4-yl)amino)ethyl)-5-chloro-3-phenylquinazolin-4(3H)-one (Compound 147a);

(S)-2-(1-((6-amino-5-((4-(trifluoromethyl)pyridin-2-yl)ethynyl)pyrimidin-4-yl)amino)ethyl)-5-chloro-3-phenylquinazolin-4(3H)-one (Compound 148a): ¹H NMR (400 MHz, DMSO-d₆) δ 10.64 (s, 1H), 10.42 (d, J=6.9 Hz, 1H), 7.82 (td, J=8.0, 0.9 Hz, 1H), 7.74-7.51 (m, 8H), 6.55 (brs, 1H), 4.95-4.84 (m, 1H), 2.54-2.43 (m, 4H), 1.34 (dd, J=6.5, 1.0 Hz, 3H). ES/MS 562.1 (M+H⁺);

(S)-2-(1-((6-amino-5-((4-(difluoromethyl)pyridin-2-yl)ethynyl)pyrimidin-4-yl)amino)ethyl)-5-chloro-3-phenylquinazolin-4(3H)-one (Compound 149a);

(S)-2-(1-((6-amino-5-((4-ethylpyridin-2-yl)ethynyl)pyrimidin-4-yl)amino)ethyl)-5-chloro-3-phenylquinazolin-4(3H)-one (Compound 150a);

(S)-2-(1-((6-amino-5-((6-(trifluoromethyl)pyridin-2-yl)ethynyl)pyrimidin-4-yl)amino)ethyl)-5-chloro-3-phenylquinazolin-4(3H)-one (Compound 151a);

(S)-2-(1-((5-((3-acetylpyridin-2-yl)ethynyl)-6-aminopyrimidin-4-yl)amino)ethyl)-5-chloro-3-phenylquinazolin-4(3H)-one (Compound 152a);

(S)-2-(1-((5-((6-acetylpyridin-2-yl)ethynyl)-6-aminopyrimidin-4-yl)amino)ethyl)-5-chloro-3-phenylquinazolin-4(3H)-one (Compound 153a);

(S)-2-(1-((6-amino-5-((4-(hydroxymethyl)pyridin-2-yl)ethynyl)pyrimidin-4-yl)amino)ethyl)-5-chloro-3-phenylquinazolin-4(3H)-one (Compound 154a);

(S)-2-(1-((6-amino-5-((6-(hydroxymethyl)pyridin-2-yl)ethynyl)pyrimidin-4-yl)amino)ethyl)-5-chloro-3-phenylquinazolin-4(3H)-one (Compound 155a);

(S)-2-((4-amino-6-((1-(5-chloro-4-oxo-3-phenyl-3,4-dihydroquinazolin-2-yl)ethyl)amino)pyrimidin-5-yl)ethynyl)isonicotinamide (Compound 156a): ¹H NMR (400 MHz, DMSO-d₆) δ 8.87 (dt, J=5.1, 0.8 Hz, 1H), 8.34 (s, 1H), 8.28 (dt, J=1.8, 1.0 Hz, 1H), 8.13 (d, J=6.6 Hz, 1H), 8.01-7.77 (m, 5H), 7.74-7.45 (m, 7H), 4.90-4.75 (m, 1H), 1.36 (dd, J=6.6, 1.1 Hz, 3H), 1.24 (s, 2H). ES/MS 536.2 (M+H⁺);

2-((1S)-1-((6-amino-5-((6-(1-hydroxyethyl)pyridin-2-yl)ethynyl)pyrimidin-4-yl)amino)ethyl)-5-chloro-3-phenylquinazolin-4(3H)-one (Compound 157a): ¹H NMR (400 MHz, DMSO-d₆) δ 8.20 (s, 1H), 8.07 (t, J=8.6 Hz, 1H), 7.94 (t, J=7.8 Hz, 1H), 7.91-7.82 (m, 1H), 7.83-7.68 (m, 3H), 7.65-7.48 (m, 9H), 4.85 (m, 2H), 1.48-1.34 (m, 7H). ES/MS 538.1 (M+H⁺);

(S)-methyl 2-((4-amino-6-((1-(5-chloro-4-oxo-3-phenyl-3,4-dihydroquinazolin-2-yl)ethyl)amino)pyrimidin-5-yl)ethynyl)isonicotinate (Compound 158a): ¹H NMR (400 MHz, DMSO-d₆) δ 8.97 (dd, J=5.1, 1.0 Hz, 1H), 8.40 (dt, J=1.7, 0.9 Hz, 1H), 8.20 (s, 1H), 7.96 (ddd, J=8.2, 1.3, 0.5 Hz, 1H), 7.92-7.83 (m, 3H), 7.67-7.51 (m, 9H), 4.86 (t, J=7.2 Hz, 1H), 3.94 (s, 3H), 1.37 (dd, J=6.7, 1.9 Hz, 3H). ES/MS 552.1 (M+H⁺);

(S)-2-(1-((6-amino-5-((6-(aminomethyl)pyridin-2-yl)ethynyl)pyrimidin-4-yl)amino)ethyl)-5-chloro-3-phenylquinazolin-4(3H)-one (Compound 159a): ¹H NMR (400 MHz, DMSO-d₆) δ 8.33 (s, 3H), 8.02-7.92 (m, 2H), 7.87 (d, J=7.7 Hz, 1H), 7.77 (td, J=8.0, 0.8 Hz, 1H), 7.66-7.45 (m, 8H), 7.17 (s, 1H), 7.08 (s, 2H), 4.74 (p, J=6.6 Hz, 1H), 4.25 (q, J=5.8 Hz, 2H), 1.35 (d, J=6.6 Hz, 3H). ES/MS 522.2 (M+H⁺);

(S)-2-((4-amino-6-((1-(5-chloro-4-oxo-3-phenyl-3,4-dihydroquinazolin-2-yl)ethyl)amino)pyrimidin-5-yl)ethynyl)isonicotinic acid (Compound 160a): ¹H NMR (400 MHz, DMSO-d₆) δ 8.92 (dt, J=5.1, 0.9 Hz, 1H), 8.36 (dt, J=1.7, 0.8 Hz, 1H), 8.07 (s, 1H), 7.96 (dt, J=8.3, 1.0 Hz, 1H), 7.91-7.70 (m, 3H), 7.66-7.47 (m, 10H), 4.81 (t, J=6.6 Hz, 1H), 1.34 (d, J=6.6 Hz, 3H). ES/MS 538.2 (M+H⁺);

(S)-2-(1-((5-((3-acetylphenyl)ethynyl)-6-aminopyrimidin-4-yl)amino)ethyl)-5-chloro-3-phenylquinazolin-4(3H)-one (Compound 161a): ¹H NMR (400 MHz, DMSO-d₆) δ 8.10 (d, J=5.4 Hz, 1H), 7.82-7.69 (m, 4H), 7.68-7.46 (m, 9H), 7.46-7.31 (m, 2H), 4.87-4.77 (m, 1H), 4.55 (s, 3H), 1.38 (d, J=6.5 Hz, 3H). ES/MS 536.1 (M+H⁺);

(S)-2-(1-((6-amino-5-((3-(hydroxymethyl)phenyl)ethynyl)pyrimidin-4-yl)amino)ethyl)-5-chloro-3-phenylquinazolin-4(3H)-one (Compound 162a): ¹H NMR (400 MHz, DMSO-d₆) δ 8.35-8.29 (m, 1H), 8.10 (s, 1H), 8.02 (dt, J=8.1, 2.1 Hz, 2H), 7.77 (m, 3H), 7.67-7.48 (m, 10H), 4.80 (q, J=6.8 Hz, 1H), 2.63 (d, J=0.8 Hz, 2H), 1.41 (d, J=6.7 Hz, 3H). ES/MS 524.1 (M+H⁺);

(S)-2-(1-((6-amino-5-((3-(hydroxymethyl)pyridin-2-yl)ethynyl)pyrimidin-4-yl)amino)ethyl)-5-chloro-3-phenylquinazolin-4(3H)-one (Compound 163a): ¹H NMR (400 MHz, DMSO-d₆) δ 10.53 (s, 1H), 9.56 (s, 1H), 8.66 (d, J=5.0 Hz, 1H), 8.14 (s, 1H), 7.95 (d, J=7.7 Hz, 1H), 7.74 (d, J=8.2 Hz, 1H), 7.61 (d, J=8.1 Hz, 2H), 7.54-7.26 (m, 5H), 7.11 (m, 1H), 5.93 (d, J=0.9 Hz, 1H), 5.47 (s, 2H), 4.87 (m, 1H), 3.84 (brs, 2H), 1.39 (d, J=7.1 Hz, 3H). ES/MS 524.1 (M+H$^+$); and (S)-2-(1-((6-amino-5-((5-methylpyridin-2-yl)ethynyl)pyrimidin-4-yl)amino)ethyl)-5-chloro-3-(3,5-difluorophenyl)quinazolin-4(3H)-one (Compound 164a).

Biological Examples

Activity testing was conducted in the Examples below using methods described herein and those well known in the art.

Example B1

Enzymatic Activity of PI3K Isoforms

Enzymatic activity of the class I PI3K isoforms was measured using a time-resolved fluorescence resonance energy transfer (TR-FRET) assay that monitors formation of the product 3,4,5-inositol triphosphate molecule (PIP3), as it competes with fluorescently labeled PIP3 for binding to the GRP-1 pleckstrin homology domain protein. An increase in phosphatidylinositide 3-phosphate product results in a decrease in TR-FRET signal as the labeled fluorophore is displaced from the GRP-1 protein binding site.

Class I PI3K isoforms were expressed and purified as heterodimeric recombinant proteins. All assay reagents and buffers for the TR-FRET assay were purchased from Millipore. PI3K isoforms were assayed under initial rate conditions in the presence of 25 mM Hepes (pH 7.4), and 2× Km ATP (100-300 μM), 10 μM PIP2, 5% glycerol, 5 mM MgCl2, 50 mM NaCl, 0.05% (v/v) Chaps, 1 mM dithiothreitol, 1% (v/v) DMSO at the following concentrations for each isoform: PI3K α, β, δ, and γ at 50 picomolar (pM) and PI3Kγ at 2 nanomolar (nM). After an assay reaction time of 30 minutes at 25° C., reactions were terminated with a final concentration of 10 mM EDTA, 10 nM labeled-PIP3, and 35 nM Europium labeled GRP-1 detector protein before reading TR-FRET on an Envision plate reader (Ex: 340 nm; Em: 615/665 nm; 100 μs delay and 500 μs read window).

Data are normalized based on a positive (1 uM wortmanin) and negative (DMSO) controls PI3K α, β, δ, and γ IC$_{50}$ values were calculated from the fit of the dose-response curves to a four-parameter equation. IC$_{50}$ are reported in units of nM. These assays generally produced results within 3-fold of the reported mean. The data collected from these assays are summarized in Table 2 below.

TABLE 2

Summary of IC$_{50}$ data

| Compound No. | IC50-PIP-α | IC50-PIP-β | IC50-PIP-δ | IC50-PIP-γ |
|---|---|---|---|---|
| 1a | >1 uM | >1 uM | <100 nM | >1 uM |
| 2a | >1 uM | >1 uM | <100 nM | >1 uM |
| 3a | >1 uM | >1 uM | <100 nM | <1 uM and >100 nM |
| 4a | >1 uM | <1 uM and >100 nM | <100 nM | >1 uM |
| 5a | >1 uM | >1 uM | <100 nM | >1 uM |
| 6a | >1 uM | <1 uM and >100 nM | <100 nM | <1 uM and >100 nM |
| 7a | >1 uM | >1 uM | <100 nM | >1 uM |
| 8a | >1 uM | >1 uM | <100 nM | >1 uM |
| 9a | >1 uM | >1 uM | <100 nM | >1 uM |
| 10a | >1 uM | <1 uM and >100 nM | <100 nM | <1 uM and >100 nM |
| 11a | >1 uM | <1 uM and >100 nM | <100 nM | >1 uM |
| 12a | >1 uM | <1 uM and >100 nM | <100 nM | <1 uM and >100 nM |
| 13a | >1 uM | <1 uM and >100 nM | <100 nM | >1 uM |
| 14a | >1 uM | >1 uM | <1 uM and >100 nM | >1 uM |
| 15a | <1 uM and >100 nM | <100 nM | <100 nM | <1 uM and >100 nM |
| 16a | >1 uM | <100 nM | <100 nM | <1 uM and >100 nM |
| 17a | <1 uM and >100 nM | <1 uM and >100 nM | <100 nM | <100 nM |
| 18a | <100 nM | <100 nM | <100 nM | <100 nM |
| 19a | >1 uM | >1 uM | <100 nM | >1 uM |
| 19b | >1 uM | >1 uM | <100 nM | >1 uM |
| 20a | >1 uM | >1 uM | <100 nM | >1 uM |
| 20b | >1 uM | >1 uM | <100 nM | >1 uM |
| 23a | >1 uM | >1 uM | <100 nM | >1 uM |
| 24a | >1 uM | >1 uM | <100 nM | >1 uM |
| 25a | <1 uM and >100 nM | <1 uM and >100 nM | <100 nM | <100 nM |
| 26a | >1 uM | >1 uM | <1 uM and >100 nM | >1 uM |
| 27a | >1 uM | >1 uM | <100 nM | <1 uM and >100 nM |
| 28a | >1 uM | >1 uM | <100 nM | >1 uM |
| 29a | >1 uM | >1 uM | <100 nM | >1 uM |
| 30a | <1 uM and >100 nM | <100 nM | <100 nM | <1 uM and >100 nM |
| 31a | <100 nM | <100 nM | <100 nM | <100 nM |
| 32a | <1 uM and >100 nM | <1 uM and >100 nM | <100 nM | <1 uM and >100 nM |
| 33a | <100 nM | <100 nM | <100 nM | <100 nM |
| 34a | >1 uM | <1 uM and >100 nM | <100 nM | <1 uM and >100 nM |
| 35a | <100 nM | <100 nM | <100 nM | <100 nM |
| 36a | >1 uM | >1 uM | <1 uM and >100 nM | >1 uM |
| 37a | >1 uM | <1 uM and >100 nM | <100 nM | <1 uM and >100 nM |
| 38a | <1 uM and >100 nM | <100 nM | <100 nM | >1 uM |
| 39a | <1 uM and >100 nM | <1 uM and >100 nM | <100 nM | <1 uM and >100 nM |
| 40a | <1 uM and >100 nM | <1 uM and >100 nM | <100 nM | <1 uM and >100 nM |
| 41a | >1 uM | >1 uM | <100 nM | >1 uM |
| 42a | >1 uM | >1 uM | <100 nM | <1 uM and >100 nM |
| 43a | >1 uM | >1 uM | <100 nM | <1 uM and >100 nM |
| 44a | <1 uM and >100 nM | <1 uM and >100 nM | <100 nM | <100 nM |
| 45a | >1 uM | >1 uM | <100 nM | >1 uM |

TABLE 2-continued

Summary of IC$_{50}$ data

| Compound No. | IC50-PIP-α | IC50-PIP-β | IC50-PIP-δ | IC50-PIP-γ |
|---|---|---|---|---|
| 46a | <1 uM and >100 nM | <100 nM | <100 nM | <100 nM |
| 47a | >1 uM | <1 uM and >100 nM | <100 nM | <1 uM and >100 nM |
| 48a | >1 uM | <1 uM and >100 nM | <100 nM | <1 uM and >100 nM |
| 49a | <1 uM and >100 nM | <100 nM | <100 nM | <100 nM |
| 50a | <1 uM and >100 nM | <100 nM | <100 nM | <1 uM and >100 nM |
| 51a | <1 uM and >100 nM | <100 nM | <100 nM | <100 nM |
| 52a | >1 uM | >1 uM | <100 nM | >1 uM |
| 53a | >1 uM | >1 uM | <100 nM | >1 uM |
| 54a | >1 uM | <1 uM and >100 nM | <100 nM | <1 uM and >100 nM |
| 55a | >1 uM | >1 uM | <100 nM | >1 uM |
| 56a | >1 uM | >1 uM | <100 nM | >1 uM |
| 57a | >1 uM | >1 uM | <100 nM | >1 uM |
| 58a | >1 uM | >1 uM | <1 uM and >100 nM | >1 uM |
| 59a | >1 uM | >1 uM | <1 uM and >100 nM | >1 uM |
| 60a | >1 uM | >1 uM | <100 nM | >1 uM |
| 61a | >1 uM | >1 uM | <100 nM | >1 uM |
| 62a | >1 uM | <1 uM and >100 nM | <100 nM | <1 uM and >100 nM |
| 63a | >1 uM | >1 uM | <100 nM | >1 uM |
| 64a | >1 uM | >1 uM | <100 nM | >1 uM |
| 65a | >1 uM | >1 uM | <100 nM | >1 uM |
| 66a | >1 uM | >1 uM | <100 nM | >1 uM |
| 67a | >1 uM | >1 uM | <100 nM | <1 uM and >100 nM |
| 68a | >1 uM | >1 uM | <100 nM | >1 uM |
| 69a | >1 uM | <1 uM and >100 nM | <100 nM | >1 uM |
| 70a | >1 uM | >1 uM | <100 nM | >1 uM |
| 71a | >1 uM | >1 uM | <100 nM | >1 uM |
| 72a | >1 uM | >1 uM | <100 nM | >1 uM |
| 73a | >1 uM | <1 uM and >100 nM | <100 nM | >1 uM |
| 74a | >1 uM | >1 uM | <100 nM | >1 uM |
| 75a | <1 uM and >100 nM | <100 nM | <100 nM | <1 uM and >100 nM |
| 76a | >1 uM | <1 uM and >100 nM | <100 nM | <1 uM and >100 nM |
| 77a | >1 uM | >1 uM | <100 nM | >1 uM |
| 78a | >1 uM | >1 uM | <100 nM | <1 uM and >100 nM |
| 79a | >1 uM | <100 nM | <100 nM | <1 uM and >100 nM |
| 80a | <100 nM | <100 nM | <100 nM | <100 nM |
| 81-1a | >1 uM | >1 uM | <100 nM | >1 uM |
| 81-2a | >1 uM | >1 uM | <100 nM | >1 uM |
| 82a | >1 uM | >1 uM | <100 nM | >1 uM |
| 83a | >1 uM | >1 uM | <100 nM | <1 uM and >100 nM |
| 84a | >1 uM | >1 uM | <100 nM | <1 uM and >100 nM |
| 85a | >1 uM | >1 uM | <100 nM | >1 uM |
| 86a | >1 uM | <1 uM and >100 nM | <100 nM | >1 uM |
| 87a | >1 uM | >1 uM | <100 nM | >1 uM |
| 9b | >1 uM | >1 uM | <100 nM | >1 uM |
| 89a | >1 uM | <1 uM and >100 nM | <100 nM | <1 uM and >100 nM |
| 90a | >1 uM | >1 uM | <100 nM | >1 uM |
| 91a | >1 uM | <1 uM and >100 nM | <100 nM | >1 uM |
| 92a | >1 uM | >1 uM | <100 nM | >1 uM |
| 93a | >1 uM | >1 uM | <100 nM | >1 uM |
| 94a | >1 uM | >1 uM | <100 nM | >1 uM |
| 95a | >1 uM | >1 uM | <100 nM | >1 uM |
| 96a | >1 uM | >1 uM | <100 nM | >1 uM |
| 97a | >1 uM | >1 uM | <100 nM | >1 uM |
| 98a | <1 uM and >100 nM | <100 nM | <100 nM | <1 uM and >100 nM |
| 99a | >1 uM | >1 uM | <100 nM | >1 uM |
| 100a | >1 uM | >1 uM | <100 nM | >1 uM |
| 101a | >1 uM | >1 uM | <100 nM | >1 uM |
| 102a | >1 uM | <1 uM and >100 nM | <100 nM | <1 uM and >100 nM |
| 103a | >1 uM | >1 uM | <100 nM | >1 uM |
| 104a | >1 uM | <1 uM and >100 nM | <100 nM | <1 uM and >100 nM |
| 105a | >1 uM | >1 uM | <100 nM | >1 uM |
| 106a | >1 uM | <1 uM and >100 nM | <100 nM | >1 uM |
| 107a | >1 uM | >1 uM | <100 nM | >1 uM |
| 108a | >1 uM | >1 uM | <100 nM | >1 uM |
| 109a | >1 uM | <1 uM and >100 nM | <100 nM | >1 uM |
| 110a | >1 uM | >1 uM | <100 nM | >1 uM |
| 111a | >1 uM | <1 uM and >100 nM | <100 nM | <1 uM and >100 nM |
| 112a | <1 uM and >100 nM | >1 uM | <100 nM | <1 uM and >100 nM |
| 113a | >1 uM | >1 uM | <100 nM | >1 uM |
| 114a | >1 uM | <1 uM and >100 nM | <100 nM | <1 uM and >100 nM |
| 115a | >1 uM | <1 uM and >100 nM | <100 nM | >1 uM |
| 116a | <1 uM and >100 nM | <1 uM and >100 nM | <100 nM | >1 uM |
| 117a | >1 uM | >1 uM | <100 nM | >1 uM |
| 118a | >1 uM | <1 uM and >100 nM | <100 nM | >1 uM |
| 119a | >1 uM | <1 uM and >100 nM | <100 nM | >1 uM |

TABLE 2-continued

Summary of IC$_{50}$ data

| Compound No. | IC50-PIP-α | IC50-PIP-β | IC50-PIP-δ | IC50-PIP-γ |
|---|---|---|---|---|
| 120a | >1 uM | >1 uM | <100 nM | >1 uM |
| 121a | >1 uM | <1 uM and >100 nM | <100 nM | >1 uM |
| 122a | >1 uM | <1 uM and >100 nM | <100 nM | >1 uM |
| 123a | >1 uM | <1 uM and >100 nM | <100 nM | <1 uM and >100 nM |
| 124a | >1 uM | >1 uM | <100 nM | >1 uM |
| 125a | >1 uM | >1 uM | <100 nM | >1 uM |
| 126a | >1 uM | >1 uM | <100 nM | >1 uM |
| 127a | >1 uM | <100 nM | <100 nM | >1 uM |
| 128a | >1 uM | >1 uM | <100 nM | >1 uM |
| 129a | >1 uM | >1 uM | <100 nM | >1 uM |
| 130a | >1 uM | >1 uM | <100 nM | >1 uM |
| 131a | >1 uM | >1 uM | <100 nM | >1 uM |
| 132a | >1 uM | >1 uM | <100 nM | <100 nM |
| 133a | >1 uM | <1 uM and >100 nM | <100 nM | <100 nM |
| 134a | >1 uM | >1 uM | <1 uM and >100 nM | <1 uM and >100 nM |
| 135a | >1 uM | <1 uM and >100 nM | <100 nM | <100 nM |
| 136a | >1 uM | >1 uM | <100 nM | <1 uM and >100 nM |
| 137a | >1 uM | >1 uM | <1 uM and >100 nM | >1 uM |
| 138a | >1 uM | >1 uM | <100 nM | >1 uM |
| 139b | >1 uM | <1 uM and >100 nM | <100 nM | >1 uM |
| 140a | >1 uM | <1 uM and >100 nM | <100 nM | >1 uM |
| 141a | >1 uM | <100 nM | <100 nM | <1 uM and >100 nM |
| 142a | >1 uM | <100 nM | <100 nM | <1 uM and >100 nM |
| 143a | >1 uM | <100 nM | <100 nM | <1 uM and >100 nM |
| 144a | >1 uM | <1 uM and >100 nM | <100 nM | >1 uM |
| 145a | >1 uM | >1 uM | <100 nM | >1 uM |
| 146b | >1 uM | >1 uM | <100 nM | >1 uM |
| 147a | <1 uM and >100 nM | <100 nM | <100 nM | <1 uM and >100 nM |
| 148a | >1 uM | <1 uM and >100 nM | <100 nM | <1 uM and >100 nM |
| 149a | >1 uM | <100 nM | <100 nM | <100 nM |
| 150a | >1 uM | <1 uM and >100 nM | <100 nM | <100 nM |
| 151a | >1 uM | <1 uM and >100 nM | <100 nM | <1 uM and >100 nM |
| 152a | >1 uM | <1 uM and >100 nM | <100 nM | >1 uM |
| 153a | >1 uM | <1 uM and >100 nM | <100 nM | <1 uM and >100 nM |
| 154a | <1 uM and >100 nM | <100 nM | <100 nM | <100 nM |
| 155a | <1 uM and >100 nM | <100 nM | <100 nM | <100 nM |
| 156a | <1 uM and >100 nM | <100 nM | <100 nM | <1 uM and >100 nM |
| 157a | >1 uM | <100 nM | <100 nM | <1 uM and >100 nM |
| 158a | >1 uM | <1 uM and >100 nM | <100 nM | >1 uM |
| 159a | >1 uM | >1 uM | <100 nM | >1 uM |
| 160a | <1 uM and >100 nM | <100 nM | <100 nM | >1 uM |
| 161a | <100 nM | <100 nM | <100 nM | <100 nM |
| 162a | >1 uM | <1 uM and >100 nM | <100 nM | >1 uM |
| 163a | >1 uM | >1 uM | >1 uM | >1 uM |
| 164a | >1 uM | >1 uM | <100 nM | <1 uM and >100 nM |

The invention claimed is:

1. A compound having the structure of formula (I):

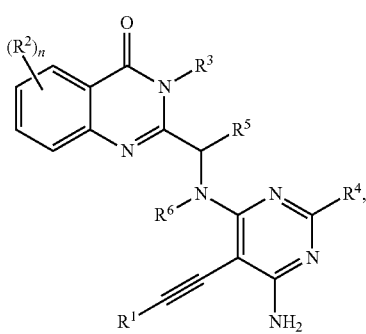

(I)

or a pharmaceutically acceptable salt thereof, wherein:

$R^1$ is unsubstituted or substituted $C_{6-12}$ aryl, unsubstituted or substituted $C_{3-12}$ heteroaryl with 1 or 2 heteroatoms independently selected from the group consisting of nitrogen and sulfur, unsubstituted or substituted $C_{3-12}$ cycloalkyl, unsubstituted or substituted $C_{3-12}$ heterocycloalkyl with 1 or 2 heteroatoms independently selected from the group consisting of nitrogen and sulfur, unsubstituted $C_{1-6}$ alkyl, or $C_{1-6}$ alkyl substituted with OH; wherein $C_{6-12}$ aryl, $C_{3-12}$ heteroaryl, $C_{3-12}$ heterocycloalkyl, or $C_{3-12}$ cycloalkyl is independently substituted with 1 or 2 substituents independently selected from the group consisting of halo, —OR$^{1a}$, —C(O)OR$^{1a}$, —C(O)R$^{1a}$, NH$_2$, $C_{1-6}$ alkyl, and haloalkyl, wherein R$^{1a}$ is $C_{1-6}$ alkyl or haloalkyl;

n is 0, 1, 2, or 3;

each $R^2$ is independently halo, unsubstituted C1-6 alkyl, or $C_{1-6}$ alkyl substituted with cyano or haloalkyl;

$R^3$ is unsubstituted $C_{6-12}$ aryl; or $C_{6-12}$ aryl substituted with 1 or 2 substituents independently selected from the group consisting of halo, alkyl, haloalkyl, cyano, —C(O)NR$^{3a}$R$^{3b}$ and —SO$_2$NR$^{3a}$R$^{3b}$, wherein R$^{3a}$ and R$^{3b}$ are independently hydrogen or $C_{1-6}$ alkyl;

$R^4$ is hydrogen, $C_{1-6}$ alkyl, or NH$_2$;

$R^5$ is $C_{1-6}$ alkyl; and $R^6$ is hydrogen, or $R^5$ together with the carbon to which it is attached and $R^6$ together with the nitrogen to which it is attached are taken together to form a, four-, five- or six-membered heterocycle.

2. The compound of claim 1, or a pharmaceutically acceptable salt thereof, wherein $R^1$ is:

unsubstituted $C_{6-12}$ aryl;

unsubstituted $C_{3-12}$ heteroaryl with 1 or 2 heteroatoms independently selected from the group consisting of nitrogen and sulfur;

unsubstituted $C_{3-12}$ cycloalkyl;

$C_{6-12}$ aryl substituted with 1 or 2 substituents independently selected from the group consisting of halo and —$OR^{1b}$, wherein $R^{1b}$ is $C_{1-6}$ alkyl or $C_{1-6}$ haloalkyl, $C_{3-12}$ heteroaryl or $C_{3-12}$ cycloalkyl independently substituted with 1 or 2 substituents independently selected from the group consisting of halo, —$OR^{1a}$, —$C(O)OR^{1a}$, —$C(O)R^{1a}$, $N_2$, $C_{1-6}$ alkyl, and haloalkyl, wherein $R^{1a}$ is $C_{1-6}$ alkyl or haloalkyl;

unsubstituted $C_{1-6}$ alkyl; or $C_{1-6}$ alkyl substituted with OH.

3. The compound of claim 1, or a pharmaceutically acceptable salt thereof, wherein $R^1$ is:

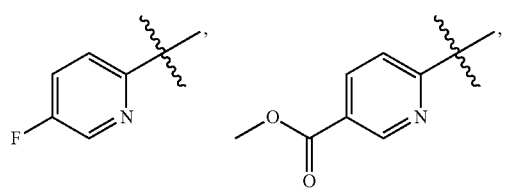

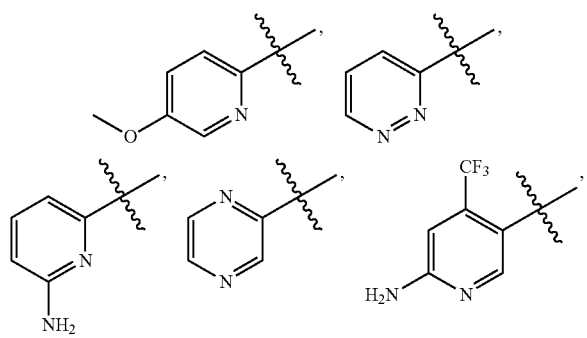

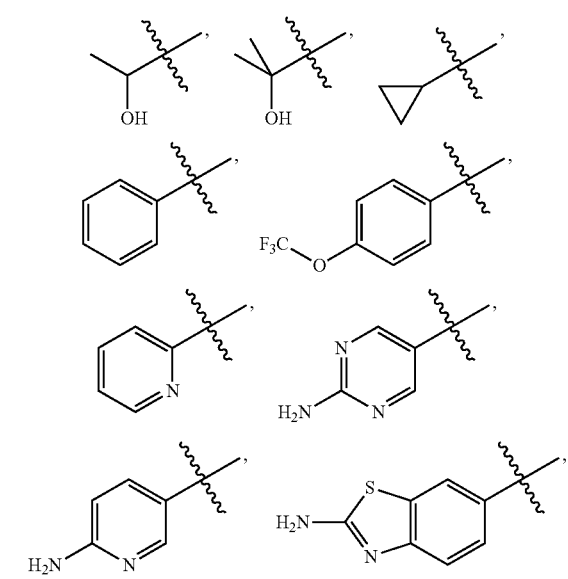

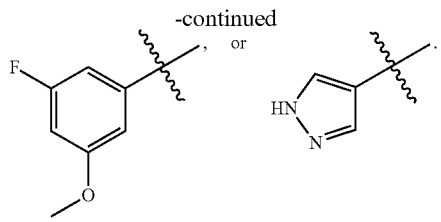

4. The compound of claim 1, or a pharmaceutically acceptable salt thereof, wherein $R^3$ is:

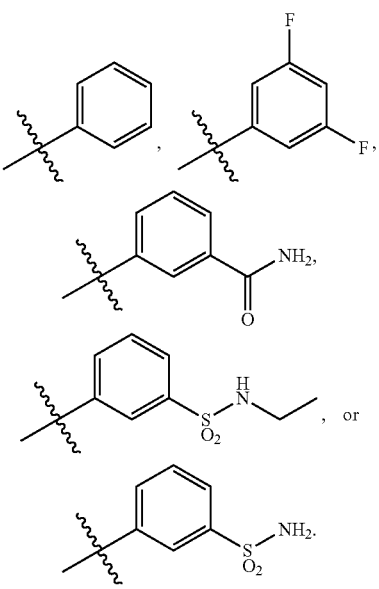

5. The compound of claim 1, or a pharmaceutically acceptable salt thereof, wherein $R^6$ is hydrogen.

6. The compound of claim 1, or a pharmaceutically acceptable salt thereof, wherein $R^5$ together with the carbon to which it is attached and $R^6$ together with the nitrogen to which it is attached are taken together to form a five- or six-membered heterocycloalkyl.

7. The compound of claim 1, wherein the compound is the (S)-enantiomer.

8. The compound of claim 1, wherein the compound has the structure of formula (IA):

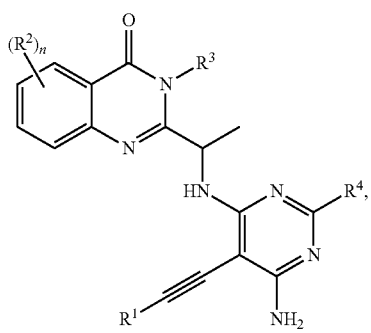

(IA)

or a pharmaceutically acceptable salt thereof, wherein:
$R^1$ is unsubstituted or substituted $C_{6-12}$ aryl, unsubstituted or substituted $C_{3-12}$ heteroaryl with 1 or 2 heteroatoms independently selected from the group consisting of nitrogen and sulfur, unsubstituted or substituted $C_{3-12}$ cycloalkyl, unsubstituted or substituted $C_{3-12}$ heterocycloalkyl with 1 or 2 heteroatoms independently selected from the group consisting of nitrogen and sulfur, unsubstituted $C_{1-6}$ alkyl, or $C_{1-6}$ alkyl substituted with OH; wherein $C_{6-12}$ aryl, $C_{3-12}$ heteroaryl, $C_{3-12}$ heterocycloalkyl, or $C_{3-12}$ cycloalkyl is independently substituted with 1 or 2 substituents independently selected from the group consisting of halo, —$OR^{1a}$, —$C(O)OR^{1a}$, —$C(O)R^{1a}$, $NH_2$, $C_{1-6}$ alkyl, and haloalkyl, wherein $R^{1a}$ is $C_{1-6}$ alkyl or haloalkyl;

n is 0, 1, 2, or 3;

each $R^2$ is independently halo or $C_{1-6}$ alkyl;

$R^3$ is unsubstituted or substituted $C_{1-6}$ aryl; and $R^4$ is hydrogen or $NH_2$.

9. The compound of claim 1, wherein the compound has the structure of formula (IB):

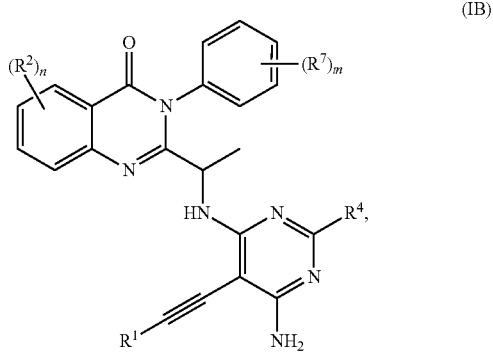

(IB)

or a pharmaceutically acceptable salt thereof, wherein:

$R^1$ is unsubstituted or substituted $C_{6-12}$ aryl, unsubstituted or substituted $C_{3-12}$ heteroaryl with 1 or 2 heteroatoms independently selected from the group consisting of nitrogen and sulfur; unsubstituted or substituted $C_{3-12}$ cycloalkyl, unsubstituted or substituted $C_{3-12}$ heterocycloalkyl with 1 or 2 heteroatoms independently selected from the group consisting of nitrogen and sulfur, unsubstituted $C_{1-6}$ alkyl, or $C_{1-6}$ alkyl substituted with OH; wherein $C_{6-12}$ aryl, $C_{3-12}$ heteroaryl, $C_{3-12}$ heterocycloalkyl, or $C_{3-12}$ cycloakyl is independently substituted with 1 or 2 substituents independently selected from the group consisting of halo, —$OR^{1a}$, —$C(O)OR^{1a}$, —$C(O)R^{1a}$, $NH_2$, $C_{1-6}$ alkyl, and haloalkyl, wherein $R^{1a}$ is $C_{1-6}$ alkyl or haloalkyl;

n is 0, 1, 2, or 3;

each $R^2$ is independently halo, unsubstituted $C_{1-6}$ alkyl, or $C_{1-6}$ alkyl; substituted with cyano or haloalkyl;

$R^4$ is hydrogen or $NH_2$;

m is 0, 1 or 2; and each $R^7$ is independently halo, —$C(O)NR^{3a}R^{3b}$ and —$S(O)_2NR^{3a}R^{3b}$, wherein $R^{3a}$ and $R^{3b}$ are independently hydrogen or $C_{1-6}$ alkyl.

10. The compound of claim 1, wherein the compound has the structure of formula (IC):

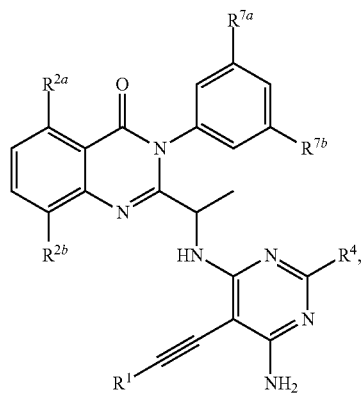

(IC)

or a pharmaceutically acceptable salt thereof, wherein:

$R^1$ is unsubstituted or substituted $C_{6-12}$ aryl, unsubstituted or substituted $C_{3-12}$ heteroaryl with 1 or 2 heteroatoms independently selected from the group consisting of nitrogen and sulfur, unsubstituted or substituted $C_{3-12}$ cycloalkyl, unsubstituted or substituted $C_{3-12}$ heterocycloalkyl with 1 or 2 heteroatoms independently selected from the group consisting of nitrogen and sulfur, unsubstituted $C_{1-6}$ alkyl, or $C_{1-6}$ alkyl substituted with OH; wherein $C_{6-12}$ aryl, $C_{3-12}$ heteroaryl, $C_{3-12}$ heterocycloalkyl, or $C_{3-12}$ cycloakyl is independently substituted with 1 or 2 substituents independently selected from the group consisting of halo, —$OR^{1a}$, —$C(O)OR^{1a}$, —$C(O)R^{1a}$, $NH_2$, $C_{1-6}$ alkyl, and haloalkyl, wherein $R^{1a}$ is $C_{1-6}$ alkyl or haloalkyl;

$R^{2a}$ and $R^{2b}$ are independently hydrogen, halo or unsubstituted or substituted $C_{1-6}$ alkyl;

$R^4$ is hydrogen, $C_{1-6}$ alkyl, or $NH_2$; and $R^{7a}$ and $R^{7b}$ are independently hydrogen, halo, —$C(O)NR^{3a}R^{3b}$ and —$S(O)_2NR^{3a}R^{3b}$, wherein $R^{3a}$ and $R^{3b}$ are independently hydrogen or $C_{1-6}$ alkyl.

11. The compound of claim 1, or a pharmaceutically acceptable salt thereof, wherein the compound is selected from the group consisting of:

(S)-2-(1-((6-amino-5-((5-fluoropyridin-2-yl)ethynyl)pyrimidin-4-yl)amino)ethyl)-3-(3,5-difluorophenyl)-5,8-difluoroquinazolin-4(3 H)-one;

(S)-2-(1-((6-amino-5-((5-fluoropyridin-2-yl)ethynyl)pyrimidin-4-yl)amino)ethyl)3-(3,5-difluorophenyl)-8-fluoroquinazolin-4(3H)-one;

(S)-methyl 6-((4-amino-6-(1-(5-chloro-4-oxo-3-phenyl-3,4-dihydroquinazolin-2-yl)ethyl)amino)pyrimidin-5-yl) ethynyl)nicotinate;

(S)-2-(1-((6-amino-5-((5-fluoropyridin-2-yl)ethynyl)pyrimidin-4-yl)amino)ethyl)5,8 difluoro-3-phenylquinazolin-4(3H)-one;

(S)-2-(1-((6-amino-5-((5-fluoropyridin-2-yl)ethynyl)pyrimidin-4-yl)amino)ethyl)-8-chloro-3-phenylquinazolin-4(3H)-one;

(S)-2-(1-((6-amino-5-((5-fluoropyridin-2-yl)ethynyl)pyrimidin-4-yl)amino)ethyl)-5-cloro 8-fluoro-3-phenylquinazolin-4(3H)-one;

(S)-2-(1-((6-amino-5-((5-fluoropyridin-2-yl)ethynyl)pyrimidin-4-yl)amino)ethyl)-3-(3,5-difluorophenyl)-5-fluoroquinazolin-4(3H)-one;

(S)-2-(1-((6-amino-5-((5-fluoropyridin-2-yl)ethynyl)pyrimidin-4-yl)amino)ethyl)-5-fluoro-3-phenylquinazolin-4(3H)-one;

(S)-2-(1-((6-amino-5 ((5-fluoropyridin-2-yl)ethynyl)pyrimidin-4-ylamino)ethyl)-5-chloro-3-(3,5-difluorophenyl)quinazolin-4(3H)-one;

(S)-2-1-((6-amino-5-((5-methoxypyridin-2-yl)ethynyl)pyrimidin-4-yl)amino)ethyl)-5,8-dichloro-3-phenylquinazolin-4(3H)-one;

(S)-2(1-((6-amino-5-((5-fluoropyridin-2-yl)ethynyl)pyrimidin-4-yl)amino)ethyl)-5,8-dichloro-3-phenylquinazolin-4(3H)-one;

(S)-2-(1-((6-amino-5-(5-methoxypyridin-2-yl)ethynyl)pyrimidin-4-yl)amino)ethyl)-8-fluoro-3-phenylquinazolin-4(3H)-one;

(S)-2-(1-((6-amino-5-((5-fluoropyridin-2-yl)ethynyl)pyrimidin-4-yl)amino)ethyl)-8-fluoro-3-phenylquinazolin-4(3H)-one;

(S)-2-(1-((6-amino-5-(pyridazin-3-ylethynyl)pyrimidin-4-yl)amino)ethyl)-5-chloro-3-phenylquinazolin-4(3H)-one;

(S)-2-(1-((6-amino-5-((6-aminopyridin-2-yl)ethynyl)pyrimidin-4-yl)amino)ethyl)-5-chloro 3-(3,5-difluorophenyl)quinazolin-4(3H)-one;

(S)2-(1-((6-amino-5-pyrazin-2-ylethynyl)pyrimidin-4-yl)amino)ethyl)-5-chloro-3-phenylquinazolin-4(3H)-one;

(S)-2-(1-((6-amino-5-((6-amino-4-(trifluoromethyl)pyridin-3-yl)ethynyl)pyrimidin-4-yl)amino)ethyl)-5-chloro-3-(3,5-difluorophenyl)quinazolin-4(3H)-one;

(S)-2-(1-((6-amino-((6-amino-4-(trifluoromethyl)pyridin-3 yl)ethynyl)pyrimidin-4-yl)amino)ethyl)-5-chloro-3-phenylquinazolin-4(3H)-one;

2-((S)-1-((6-amino-5-((R)-3-hydroxybut-1-yn-1-yl)pyrimidin-4-yl)amino)ethyl)-5-chloro-3-phenylquinazolin-4(3H)-one;

2-((S)-1-((6-amino-5-((S)-3-hydroxybut-1-yn-1-yl)pyrimidin-4-yl)amino)ethyl)-5-chloro-3-phenylquinazolin-4(3H)-one;

2-((S)-1-((6-amino-5-((R)-3-hydroxybut-1-yn-1-yl)pyrimidin-4-yl)amino)ethyl)-5-chloro-3-(3,5-difluorophenyl)quinazolin-4(3-H)-one;

2-((S)-1-((6-amino-5-((S)-3-hydroxybut-1-yn-1-yl)pyrimidin-4-yl)amino)ethyl)-5-chloro-3-(3,5-difluorophenyl)quinazolin-4(3H)-one;

(S)-2-(1-((6-amino-5-(cyclopropylethynyl)pyrimidin-4-yl)amino)ethyl)-5-chloro-3-(3,5-difluorophenyl)quinazolin-4(3H)-one;

(S)-2-(1-((6-amino-5-(cyclopropylethynyl)pyrimidin-4-yl)amino)ethyl)-5-chloro-3-phenylquinazolin-4(3H)-one;

(S)-5-chloro-2-(1-((2,6-diamino-5-(phenylethynyl)pyrimidin-4-yl)amino)ethyl)-3-phenylquinazolin-4(3H)-one;

(S)-2-(1-((6-amino-5-((4-(trifluoromethoxy)phenyl)ethynyl)pyrimidin-4-yl)amino)ethyl)-5-chloro-3-(3,5-difluorophenyl)quinazolin-4(3H)-one;

(S)-2-(1-((6-amino-5-((4-(trifluoromethoxy)phenyl)ethynyl)pyrimidin-4-yl)amino)ethyl)-5-chloro-3-phenylquinazolin-4(3H i)-one;

(S)-2-(1-((6-amino-5-(3-hydroxy-3-methylbut-1-yn-1-yl)pyrimidin-4-yl)amino)ethyl)-5-chloro-3-(3,5-difluorophenyl)quinazolin-4(3H)-one;

(S)-2-(1-((6-amino-5-(3-hydroxy-3-methylbut-1-yn-1-yl)pyrimidin-4-yl)amino)ethyl)-5-chloro-3-phenylquinazolin-4(3H)-one;

(S)-2-(1-((6-amino-5-(pyridin-2-ylethynyl)pyrimidin-4-yl)amino)ethyl)-5-methyl-3-phenylquinazolin-4(3H)-one;

(S)-2-(1-((6-amino-5-((6-aminopyridin-2-yl)ethynyl)pyrimidin-4-yl)amino)ethyl)-5-chloro-3-phenylquinazolin-4(3H)-one;

(S)-2-(1-((6-amino-5-((2-aminopyrimidin-5-yl)ethynyl)pyrimidin-4-yl)amino)ethyl)-5-chloro-3-(3,5-difluorophenyl)quinazolin-4(3H)-one;

(S)-2-(1-((6-amino-5-((2-aminopyrimidin-5-yl)ethynyl)pyrimidin-4-yl)amino)ethyl)-5-chloro-3-phenylquinazolin-4(3H)-one;

(S)-2-(1-((6-amino-5-((5-aminopyridin-2-yl)ethynyl)pyrimidin-4-yl)amino)ethyl)-5-chloro-3-(3,5-difluorophenyl)quinazolin-4(3H)-one;

(S)-2-(1-((6-amino-5-((5-aminopyridin-2-yl)ethynyl)pyrimidin-4-yl)amino)ethyl)-5-chloro-3-phenylquinazolin-4(3H)-one;

(S)-2-(1-(6-amino-5-(pyridin-2-ylethynyl)pyrimidin-4-yl)piperidin-2-yl)-5-chloro-3-phenylquinazolin-4(3H)-one;

(S)-2-(1-(6-amino-5(pyridin-2-ylethynyl)pyrimidin-4-yl)pyrrolidin-2-yl)-5-chloro-3-phenylquinazolin-4(3H)-one;

(S)-3-(2-(1-((6-amino-5-(pyridin-2-ylethynyl)pyrimidin-4-yl)amino)ethyl)-5-chloro-4-oxoquinazolin-3(4H)-yl)benzamide;

(S)-3-(2-(1-((6-amino-5-(pyridin-2-ylethynyl)pyrimidin-4-yl)amino)ethyl)-5-chloro-4-oxoquinazolin-3(4H-1)-yl)-N-ethylbenzenesulfonamide;

(S)-3-(2-(1-((6-amino-5-(pyridin-2-ylethynyl)pyrimidin-4-yl)amino)ethyl)-5-chloro-4-oxoquinazolin-3 (4H)-yl)benzenesulfonamide;

(S)-2-(1-((6-amino-5-(pyrimidin-5-ylethynyl)pyrimidin-4-yl)amino)ethyl)-5-chloro-3-(3,5-difluorophenyl)quinazolin-4(3H)-one;

(S)-2-(1-((6-amino-5-(pyrimidin-5-ylethynyl)pyrimidin-4-yl)amino)ethyl)-5-chloro-3-phenylquinazolin-4(3H)-one;

(S)-2-(1-((6-amino-5-(pyridin-3-ylethynyl)pyrimidin-4-yl)amino)ethyl)-5-chloro-3-(3,5-difluorophenyl)quinazolin-4(3H)-one;

(S)-2-(1-((6-amino-5-(pyridin-3-ylethynyl)pyrimidin-4-yl)amino)ethyl)-5-chloro-3-phenylquinazolin-4(3H)-one;

(S)-2-(1-((6-amino-5-(pyridin-2-ylethynyl)pyrimidin-4-yl)amino)ethyl-5-chloro-3-(3,5-difluorophenyl)quinazolin-4(3H)-one:

(S)-2-(1-(6-amino-5-((2-aminobenzo[d]thiazol-6-yl)ethynyl)pyrimidin-4-yl)amino)ethyl)-5-chloro-3-phenylquinazolin-4(3H)-one;

(S)-2-(1-((6-amino-5-((3-fluoro-5-methoxyphenyl)ethynyl)pyrimidin-4-yl)amino)ethyl)-5-chloro-3-phenylquinazolin-4(3H)-one:

(S)-2-(1-((6-amino-5((5-fluoropyridin-2-yl)ethynyl)pyrimidin-4-yl)amino)ethyl)5-chloro-3-phenylquinazolin-4(3H)-one;

(S)-2-(1-((5l-(1H-pyrazol-4-yl)ethynyl)-6-aminopyrimidin-4-yl)amino)ethyl)-5-chloro-3-phenylquinazolin-4(3H)-one;

(S)-2-((6-amino-5-(pyridin-2-ylethynyl)pyrimidin-4-yl)amino)ethyl)-5-chloro-3-phenylquinazolin-4(3H)-one; and (S)-2-(1-((6-amino-5-(phenylethynyl)pyrimidin-4-yl)amino)ethyl)-5-chloro-3-phenylquinazolin-4(3H)-one, or a pharmaceutically acceptable salt thereof.

12. A pharmaceutical composition comprising:
a compound of claim 1, or a pharmaceutically acceptable salt thereof; and
at least one pharmaceutically acceptable vehicle.

13. A pharmaceutical composition comprising:
a compound of claim 11, or a pharmaceutically acceptable salt thereof; and
at least one pharmaceutically acceptable vehicle.

* * * * *